US010875914B2

(12) United States Patent
van der Woning et al.

(10) Patent No.: US 10,875,914 B2
(45) Date of Patent: *Dec. 29, 2020

(54) NUCLEIC ACIDS ENCODING GARP-TGF-BETA 1 ANTIBODIES

(71) Applicants: argenx BVBA, Zwijnaarde (BE); Université Catholique de Louvain, Louvain-la-Neuve (BE)

(72) Inventors: Sebastian van der Woning, Bachte-Maria-Leerne (BE); Filip Borgions, Herk-de-Stad (BE); Torsten Dreier, Sint-Martens-Latem (BE); Lore Mariën, Ghent (BE); Gitte De Boeck, Malderen (BE); Stëphanie Liénart, Wezembeek-Oppem (BE); Sophie Lucas, Duisburg (BE); Pierre Coulie, Kraainem (BE)

(73) Assignees: argenx BVBA, Zwijnaarde (BE); Université Catholique de Louvain, Louvain-la-Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/409,679

(22) Filed: May 10, 2019

(65) Prior Publication Data
US 2019/0375832 A1 Dec. 12, 2019

Related U.S. Application Data

(63) Continuation of application No. 15/977,449, filed on May 11, 2018, now Pat. No. 10,479,829.

(51) Int. Cl.
*C07K 16/22* (2006.01)
*C07K 16/28* (2006.01)
*A61K 39/00* (2006.01)

(52) U.S. Cl.
CPC .............. *C07K 16/22* (2013.01); *C07K 16/28* (2013.01); *A61K 2039/505* (2013.01); *C07K 2317/22* (2013.01); *C07K 2317/32* (2013.01); *C07K 2317/33* (2013.01); *C07K 2317/526* (2013.01); *C07K 2317/55* (2013.01); *C07K 2317/56* (2013.01); *C07K 2317/565* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,816,567 A | 3/1989 | Cabilly |
| 5,591,828 A | 1/1997 | Bosslet |
| 5,892,019 A | 4/1999 | Schlom |
| 6,162,963 A | 12/2000 | Kucherlapati |
| 9,399,676 B2 | 7/2016 | Schurpf |
| 9,573,995 B2 | 2/2017 | Schurpf |
| 2008/0279834 A1 | 11/2008 | Garaczi |
| 2011/0300119 A1 | 12/2011 | Tran |

FOREIGN PATENT DOCUMENTS

| CA | 2999819 A1 | 3/2017 |
| EP | 0404097 A2 | 12/1990 |
| EP | 0799836 A1 | 10/1997 |
| EP | 2832747 A1 | 2/2015 |
| WO | 1993011161 A1 | 6/1993 |
| WO | 2005102387 A2 | 11/2005 |
| WO | 2006085938 A2 | 8/2006 |
| WO | 2007113301 A1 | 10/2007 |
| WO | 2009073163 A1 | 6/2009 |
| WO | 2010001251 A2 | 1/2010 |
| WO | 2014033252 A1 | 3/2014 |
| WO | 2014182676 A2 | 11/2014 |
| WO | 2015015003 A1 | 2/2015 |
| WO | 2016125017 A1 | 8/2016 |
| WO | 2018013939 A1 | 1/2018 |

OTHER PUBLICATIONS

Caron et al., 1992 "Engineered humanized dimeric forms of IgG are more effective antibodies," J Exp Med 176(4):1191-1195.
Chothia and Lesk, 1987 "Canonical structures for the hypervariable regions of immunoglobulins," J Mol Biol 196(4):901-917.
Genbank Database [Online] (Jan. 28, 2019) "transforming growth factor beta activator LRRC32 precursor [Homo sapiens]," Accession No. NP_001122394.1. National Center for Biotechnology Information. Accessible on the Internet at URL: https://www.ncbi.nlm.nih.gov/protein/np_001122394.
Hinton et al., 2006 "An Engineered Human IgG1 Antibody with Longer Serum Half-Life," J Immunol 176(1):346-356.
Hollinger and Hudson, 2005 "Engineered antibody fragments and the rise of single domains," Nat Biotechnol 23(9)1126-1136.
MacCallum et al., 1996 "Antibody-antigen interactions: contact analysis and binding site topography," J Mol Biol 262(5):732-745.
Mather, 1980 "Establishment and Characterization of Two Distinct Mouse Testicular Epithelial Cell Lines," Biol Reprod 23: 243-252.
Mather et al., 1982 "Culture of testicular cells in hormone-supplemented serum-free medium," Ann N Y Acad Sci 383:44-68.
Morea et al., 2000 "Antibody Modeling: Implications for Engineering and Design," Methods 20:267-279.

(Continued)

Primary Examiner — Elly-Gerald Stoica
(74) Attorney, Agent, or Firm — Dechert LLP

(57) ABSTRACT

The present invention relates to antibodies and antigen binding fragments thereof, which bind to a complex of GARP and TGF-β1, particularly a complex of human GARP and human TGF-β1. These antibodies and antigen binding fragments exhibit a combination of advantageous properties including high affinity antigen binding and the ability to inhibit the release of active TGF-β from regulatory T cells. The antibodies and antigen binding fragments of the present invention are relatively resistant to deamidation, isomerization and oxidation, such that they display improved stability.

18 Claims, 22 Drawing Sheets

Specification includes a Sequence Listing.

(56) References Cited

OTHER PUBLICATIONS

Natsume et al., 2009 "Improving effector functions of antibodies for cancer treatment: Enhancing ADCC and CDC," Drug Des Devel Ther 3:7-16.
Presta, 2008 "Molecular engineering and design of therapeutic antibodies," Curr Opin Immunol 20:460-470.
Rudikoff et al., 1982 "Single amino acid substitution altering antigen-binding specificity," Proc Natl Acd Sci USA 79(6):1979-1983.
Stemmer et al., 1995 "Single-step assembly of a gene and entire plasmid from large numbers of oligodeoxyribonucleotides," Gene 164(1):49-53.
Tatusova and Madden, 1999 "Blast 2 sequences—a new tool for comparing protein and nucleotide sequences", FEMS Microbiol Lett 174(2):247-250.
Tramontano et al., 1990 "Framework residue 71 is a major determinant of the position and conformation of the second hypervariable region in the VH domains of immunoglobulins," J Mol Biol 215(1):175-182.
Urlaub and Chasin, 1980 "Isolation of Chinese hamster cell mutants deficient in dihydrofolate reductase activity," Proc Natl Acad Sci U S A (7):4216-4220.
Vaccaro et al., 2005 "Engineering the Fc region of immunoglobulin G to modulate in vivo antibody levels," Nat Biotechnol 23(10):1283-1288.
Yeung et al., 2009 "Engineering Human IgG1 Affinity to Human Neonatal Fc Receptor: Impact of Affinity Improvement on Pharmacokinetics in Primates," J Immunol 182(12):7663-7671.
Zalevsky et al., 2010 "Enhanced antibody half-life improves in vivo activity," Nat Biotechnol 28(2):157-159.
Anonymous (2016) "Dissociation constant." Wikipedia, the free encyclopedia, Jun. 27, 2016 (Jun. 27, 2016) 6 pages.
Drescher 2011 "Characterization of biological interactions with Biacore." Internet Citation, pp. 1-26.
Pauthner et al., 2015 "Antibody engineering & therapeutics, the annual meeting of the antibody society Dec. 7-10, 2015. San Diego, CA. USA." Mabs, vol. 8, No. 3, pp. 617-652.
International Search Report and Written Opinion of PCT/EP2018/062251 dated Jul. 6, 2018, 14 pages.
Wang et al., 2007 "Antibody Structure, Instability, and Formulation," Journal of Pharmaceutical Sciences 96:1-26.
Klimka et al., 2000 "Human anti-CD30 recombinant antibodies by guided phage antibody selection using cell panning," Br J Cancer 83(2):252-260.
Miyara et al., 2009 "Functional delineation and differentiation dynamics of human CD4+ T cells expressing the FoxP3 transcription factor," Immunity 30(6):899-911.
Padlan et al., 1989 "Structure of an antibody-antigen complex: crystal structure of the HyHEL-10 Fab-lysozyme complex," Proc Natl Acad Sci USA 86(15): 5938-5959.
Plato 1 specification, http://www.enzolifesciences.com/ALX-804-867/lrrc32-monoclonal-antibody-plato-1/, Accessed Feb. 1, 2019 (Year: 2019) 2 pages.
Akhurst et al., 2012 "Targeting the TGFβ signalling pathway in disease," Nat Rev Drug Discovery 11(10):790-811.
Boon et al., 2006 "Human T cell responses against melanoma," Annu Rev Immunol 24:175-208.
Chan et al., 2010 "Therapeutic antibodies for autoimmunity and inflammation," Nat Rev Immunol 10(5):301-316.
Colombo et al., 2007 "Regulatory-T-cell inhibition versus depletion: the right choice in cancer immunotherapy," Nat Rev Cancer 7(11):880-887.
Cuende, 2015 "Monoclonal antibodies against GARP1TGF-b1 complexes inhibit the immunosuppressive activity of human regulatory T cells in vivo," Human Immunology 7(284):284ra56, pp. 1-12.
De Vries et al., 2010 "Frequency of circulating Tregs with demethylated FOXP3 intron 1 in melanoma patients receiving tumor vaccines and potentially Treg-depleting agents," Clin Cancer Res 17:841-848.
Edwards et al., 2013 "Regulation of the expression of GARP/latent TGF-I31 complexes on mouse T cells and their role in regulatory T cell and Th17 differentiation," J Immunol 190(11):5506-5515.
Gauthy et al., 2013 "GARP is regulated by miRNAs and controls latent TGF-β1 production by human regulatory T cells," PloS One 8(9):e76186, pp. 1-13.
Genbank Database [Online] (2003) "Immunoglobulin heavy chain variable region, partial [Mus musculus]," Accession No. AA019657.1. National Center for Biotechnology Information. Accessible on the Internet at URL: http://www.ncbi.nlm.nih.gov/protein/27752388.
Genbank Database [Online] (Apr. 30, 2011) "Mus musculus clone YC15 anti-KSHV gH immunoglobulin light chain variable region mRNA, partial cds," Accession No. JF330319.1. National Center for Biotechnology Information. Accessible on the Internet at URL: http://www.ncbi.nlm.nih.gov/nuccore/JF330319.1.
Genbank Database [Online] (Oct. 17, 2015) "*Homo sapiens* transforming growth factor, beta 1 (TGFB1), mRNA," Accession No. NM_000660. National Center for Biotechnology Information. Accessible on the Internet at URL: http://www.ncbi.nlm.nih.gov/nuccore/NM_000660.
Genbank Database [Online] (Mar. 15, 2015) "*Homo sapiens* leucine rich repeat containing 32 (LRRC32), transcript variant 2, mRNA," Accession No. NM_001128922. National Center for Biotechnology Information. Accessible on the Internet at URL: http://www.ncbi.nlm.nih.gov/nuccore/NM_001128922.
Genbank Database [Online] (Nov. 7, 2015) "*Homo sapiens* transforming growth factor beta 2 (TGFB2), transcript variant 1, mRNA," Accession No. NM_001135599. National Center for Biotechnology Information. Accessible on the Internet at URL: http://www.ncbi.nlm.nih.gov/nuccore/NM_00113559.
Genbank Database [Online] (Nov. 7, 2015) "*Homo sapiens* transforming growth factor beta 2 (TGFB2), transcript variant 2, mRNA," Accession No. NM_003238. National Center for Biotechnology Information. Accessible on the Internet at URL: http://www.ncbi.nlm.nih.gov/nuccore/NM_003238.
Genbank Database [Online] (Mar. 12, 2015) "PREDICTED: *Homo sapiens* transforming growth factor, beta 3 (TGFB3), transcript variant X1, mRNA," Accession No. XM_005268028. National Center for Biotechnology Information. Accessible on the Internet at URL: http://www.ncbi.nlm.nih.gov/nuccore/XM_005268028.
Genbank Database [Online] (Jan. 25, 2016) "Predicted: Macaca fascicularis leucine rich repeat containing 32 LRRC32), transcript variant X1, mRNA," Accession No. XM_005579140. National Center for Biotechnology Information. Accessible on the Internet at URL: http://www.ncbi.nlm.nih.gov/nuccore/XM_005579140.
Genbank Database [Online] (Jan. 25, 2016) "Predicted: Macaca fascicularis transforming growth factor beta 1 (TGFB1), transcript variant X1, mRNA," Accession No. XM_005589338. National Center for Biotechnology Information. Accessible on the Internet at URL: http://www.ncbi.nlm.nih.gov/nuccore/XM_005589338.
Graham et al. (1977) "Characteristics of a human cell line transformed by DNA from human adenovirus type 5," J Gen Viral 36:59-72.
Hannon et al., 2013 "Infusion of clinical-grade enriched regulatory T cells delays experimental xenogeneic graft-versus-host disease," Transfusion 54(2):353-363.
Jakobovitz et al., 1993 "Germ-line transmission and expression of a human-derived yeast artificial chromosome," Nat 362:255-258.
LeFranc et al., 1999 "IMGT, the international ImMunoGeneTics database," Nucl Acids Res 27:209-212.
LeMaire et al., 2011 "Induction of autoantibodies against mouse soluble proteins after immunization with living cells presenting the autoantigen at the cell surface in fusion with a human type 2 transmembrane protein," J Immunol Methods 367(1-2):56-62.
Lonning et al., 2011 "Antibody targeting of TGF-13 in cancer patients," Curr Pharm Biotechnol 12:2176-2189.
Roux et al., 1998 "Comparisons of the ability of human IgG3 hinge mutants, IgM, IgE, and IgA2, to form small immune complexes: a role for flexibility and geometry," J Immunol 161:4083-4090.
Shopes, 1992 "A genetically engineered human IgG mutant with enhanced cytolytic activity," J Immunol 148:2918-2922.

(56) References Cited

OTHER PUBLICATIONS

Stockis et al., 2009 "Comparison of stable human Treg and Th clones by transcriptional profiling," Eur J Immunol 39:869-882.
Stockis et al., 2009 "Membrane protein GARP is a receptor for latent TGF-beta on the surface of activated human Treg," Eur J Immunol 39(12):3315-3332.
Tran et al., 2009 "GARP (LRRC32) is essential for the surface expression of latent TGF-beta on platelets and activated FOXP3+ regulatory T cells," Proc Natl Acd Sci USA. 106(32):13445-13450.
Wang et al., 2012 "GARP regulates the bioavailability and activation of TGFl3," Mol Biol Cell 1129-1139.
Williams et al., 1996 "Sequence and evolution of the human germline V lambda repertoire," J Mol Biol 264:220-232.
Yamane-Ohnuki and Satoh, 2009 "Production of therapeutic antibodies with controlled fucosylation," mAbs 1 (3):230-236.
Zhou et al., 2013 "GARP-TGF-β complexes negatively regulate regulatory T cell development and maintenance of peripheral CD4+ T cells in vivo," J Immunol 190(10):5057-5064.
International Search Report with Written Opinion corresponding to International Patent Application No. PCT/EP2014/066650, dated Oct. 30, 2014.
Liewen et al., 2005 "Characterization of the human GARP (Golgi associated retrograde protein) complex," Exp Cell Res 306(1):24-34.
Miller et al., 2014 "CD4+CD25+ T regulatory cells activated during feline immunodeficiency virus infection convert T helper cells into functional suppressors through a membrane-bound TGFβ/ GARP-mediated mechanism," Viral. J. 11(1):7. pp. 1-14.
International Search Report with Written Opinion corresponding to International Patent Application No. PCT/IB2016/000182, dated May 10, 2016, 15 pages.
Engelman and Settleman, 2008 "Acquired resistance to tyrosine kinase inhibitors during cancer therapy," Current Opinion in Genetics & Development 18(1):73-79.
Kovacs et al., 2015 "Cardiac Safety of TGF-β Receptor I Kinase Inhibitor LY2157299 Monohydrate in Cancer Patients in a First-in Human Dose Study," Cardiovasc Toxicol 15(4):309-323.
Lacouture et al., 2015 "Cutaneous keratoacanthomas/squamous cell carcinomas associated with neutralization of transforming growth factor beta by the monoclonal antibody fresolimumab (GC1008)," Cancer Immunol Immunother 34(4):437-446.
Li et al., 2006 "Transforming growth factor-beta regulation of immune responses," Annu Rev Immunol 24:99-146.
Lucas et al., 2012 "Demethylation of the FOXP3 gene in human melanoma cells precludes the use of this epigenetic mark for quantification of Tregs in unseparated melanoma samples," Int J Cancer 130(8):1960-1966.
Shull et al., 1992 "Targeted disruption of the mouse transforming growth factor-beta 1 gene results in multifocal inflammatory disease," Nature 359(6397):693-699.
Silence et al., 2014 "ARGX-110, a highly potent antibody targeting CD70, eliminates tumors via both enhanced ADCC and immune checkpoint blockade," MAbs 6(2):523-532.
Tan et al., 2013 "Cellular re- and de-programming by microenvironmental memory: why short TGF-betal pulses can have long effects," Fibrogenesis Tissue Repair 6(1):1-12.
Zheng and Rudensky, 2007 "Foxp3 in control of the regulatory T cell lineage," Nat Immunol 8(5):457-462.
Zheng et al., 2007 "Genome-wide analysis of Foxp3 target genes in developing and mature regulatory T cells," Nature 445(7130):936-940.
Third Party Observation corresponding to European Patent Application No. 14748185.7, dated Jan. 13, 2017 (8 pages).
U.S. Appl. No. 61/819,840, corresponding to European Publication No. WO 2014/182676, dated May 6, 2013 (183 pages).
Non-Final Rejection corresponding to U.S. Appl. No. 15/013,706, dated Nov. 1, 2017 (14 pages).
Shevach, 2017 "Garp as a therapeutic target for modulation of T regulatory cell function," Expert Opin Ther Targets, 21(2):191-200.

|  | 10 freeze-thaw cycles | | | |
|---|---|---|---|---|
|  | Non-reducing conditions | | Reducing conditions | |
|  | Ref | 10x FT | Ref | 10x FT |
| 39B6-AVE | 1 | 2 | 5 | 6 |
| 39B6-AYE | 3 | 4 | 7 | 8 |

|  | 96 hours of rotation | | | |
|---|---|---|---|---|
|  | Non-reducing conditions | | Reducing conditions | |
|  | Ref | 96h | Ref | 96h |
| 39B6-AVE | 1 | 2 | 5 | 6 |
| 39B6-AYE | 3 | 4 | 7 | 8 |

FIG. 21

| | | | (°C/s) |
|---|---|---|---|
| Step 1 | 54,6 – 71,4 °C | 60 min | 4 °C |
| Step 2 | 25 °C | 120 min | 0.1 °C |
| Step 3 | 4 °C | pause | |

Lid temperature  80 °C

NUCLEIC ACIDS ENCODING GARP-TGF-BETA 1 ANTIBODIES

RELATED APPLICATION

This application is a continuation of U.S. application Ser. No. 15/977,449, filed May 11, 2018, which claims benefit of priority to Great Britain Provisional Application No. 1707561.5, filed on May 11, 2017, the entire contents of each of which are incorporated herein in their entireties by reference thereto.

SEQUENCE LISTING

The instant application contains a Sequence Listing which has been submitted electronically in ASCII format and is hereby incorporated by reference in its entirety. Said ASCII copy, created on Nov. 12, 2020. Is named 466C1_SL_ST25.txt and is 43,847 bytes in size.

FIELD OF THE INVENTION

The present invention relates to antibodies and antigen binding fragments thereof, which bind to a complex of GARP and TGF-β1, particularly a complex of human GARP and human TGF-β1. These antibodies and antigen binding fragments exhibit a combination of advantageous properties including high affinity antigen binding and the ability to inhibit the release of active TGF-β from regulatory T cells. The antibodies and antigen binding fragments of the present invention are improved as compared with prior art antibodies binding to the complex of GARP and TGF-β1. In particular, the antibodies and antigen binding fragments of the present invention are relatively resistant to deamidation, isomerization and oxidation, such that they display improved stability as compared with GARP-TGF-β1 antibodies described in the prior art.

BACKGROUND TO THE INVENTION

Regulatory T cells (otherwise known as "Tregs" or Foxp3+ T regulatory cells) are an important component of the immune system. In particular, Tregs play a critical role in immune homeostasis by suppressing various aspects of the immune response. As a consequence of their role in coordinating the immune response, dysregulated Treg activity can lead to the development of various diseases and conditions. In particular, insufficient Treg function can result in autoimmune pathology, whereas excessive Treg activity has been linked to the inhibition of anti-tumour responses in cancer patients.

The protein GARP (Glycoprotein A Repetitions Predominant) has been identified as a highly expressed marker on the surface of Tregs, particularly activated Tregs. GARP is an 80 kDa transmembrane protein with an extracellular region comprising 20 leucine-rich repeats. It is also known as LRRC32. GARP serves as the receptor for TGF-β, particularly the latent form of TGF-13, and is required for the expression of latent TGF-β on Treg cells (E M Shevach. Expert Opin Ther Targets (2016) 21(2), 191-200).

TGF-β is a cytokine known to play a role in multiple processes including cell proliferation and differentiation, tissue morphogenesis, inflammation and apoptosis. It has also been identified as an important growth factor implicated in cancer development, and rather unusually, has been identified as a cytokine with tumour promoting and tumour suppressive properties.

The production and activation of TGF-β is a multi-step process, which is regulated at different levels. TGF-β is synthesised as a pro-TGF-β dimeric precursor, each polypeptide chain consisting of a latency-associated peptide (LAP) and a mature TGF-β region. Pro-TGF-β undergoes cleavage by the enzyme furin to form "latent TGF-β," an inactive form in which the LAP remains non-covalently associated with the mature TGF-β region of each polypeptide chain (see FIG. 1). Membrane-localised GARP serves to transport and anchor latent TGF-β to the cell surface of Tregs, and it is from this membrane-bound GARP-latent TGF-β complex that the active form of TGF-β is released. A variety of mechanisms have been proposed to explain how active TGF-β is released from the GARP-latent TGF-β complex on the surface of Tregs. However, integrins, particularly αvβ6 and αvβ8, are now thought to play an important role in driving the shear forces needed for release of the mature TGF-β dimer.

Once released, the active TGF-β dimer can act as an autocrine or paracrine mediator of downstream signalling pathways. In the context of the immune system, TGF-β release from Treg cells is thought to influence the activity of various T effector cells and also Tregs themselves (see FIG. 1). Since Tregs play an important role in suppressing immunity, it is thought that TGF-β released from Tregs and acting in an autocrine fashion may be involved in mediating Treg suppression. In particular, Treg-derived TGF-β1 is thought to play a significant role in Treg-mediated suppression of tumour immunity.

Given the role of Treg-derived TGF-β in suppressing the immune response in the tumour microenvironment, there has been interest in targeting this pathway as an alternative approach to cancer immunotherapy. For example, therapeutic agents capable of dampening this pathway may serve as useful tools to improve the efficacy of cancer vaccines or other cancer immunotherapy strategies designed to harness the power of the body's immune system to treat cancer.

Cuende et al. (Sci Transl Med. 2015 Apr. 22; 7(284): 284ra56) describes the production and characterisation of two monoclonal antibodies (MHG-8 and LHG10), which bind to the GARP-TGF-β complex on Tregs and inhibit TGF-β production. These two antibodies are also described and characterised in International patent applications WO2015/015003 and WO2016/125017. These antibodies were shown to be capable of inhibiting the immunosuppressive activity of human Treg in a xenogeneic graft-versus-host disease mouse model. This work serves to validate the GARP-TGF-β complex as a therapeutic target of interest for the purposes of modulating Treg function and consequently treating diseases such as cancer and autoimmune disease where the level of Treg activity plays an important role. There remains a need however, for improved GARP-TGF-β antibodies capable of inhibiting TGF-β release and thereby modifying Treg activity. The present invention addresses this problem as described herein.

SUMMARY OF INVENTION

The present invention improves upon the state of the art by providing new antibodies and antigen binding fragments thereof, which bind to the human GARP-TGF-β1 complex. The antibodies and antigen binding fragments of the present invention are derived from the GARP-TGF-β1 antibody "LHG-10", described in International patent applications WO2015/015003 and WO2016/125017. The heavy chain and light chain variable domain sequences of LHG-10 are shown in SEQ ID NOs: 1 and 2, respectively, and the light chain variable domain of a chain-shuffled variant, LHG-10.6 (also described in WO2015/015003 and WO2016/125017), is shown in SEQ ID NO: 3. The antibodies of the present invention differ particularly with respect to certain CDR sequences as compared with LHG-10 and LHG-10.6, specifically with respect to the CDR2 and CDR3 sequences of the heavy chain variable domain. The LHG-10 and LHG-10.6 GARP-TGF-β antibodies possess the heavy chain CDR2 sequence: RIDPEDGGTKYAQKFQG (SEQ ID NO: 5); and the heavy chain CDR3 sequence: NEWETVVVGDLMYEYEY (SEQ ID NO: 6), whereas the antibodies of the present invention comprise the heavy chain CDR2 sequence: RIDPEDAGTKYAQKFQG (SEQ ID NO: 12); and the heavy chain CDR3 sequence: YEWETVVVGDLMYEYEY (SEQ ID NO: 13).

The differences in the heavy chain CDR2 and CDR3 sequences reported herein result in antibodies that are improved as compared with the prior art antibodies by virtue of their improved stability. More specifically, the antibodies of the present invention are relatively resistant to deamidation, isomerization and oxidation, such that they exhibit enhanced stability. Surprisingly, these specific substitutions in the heavy chain CDR2 and CDR3 regions that lead to improved stability do not significantly decrease the binding affinity of the antibodies for the GARP-TGF-β1 complex. The improved stability combined with high affinity target binding renders the antibodies of the present invention particularly suitable for clinical development as therapeutic agents, for example as cancer therapeutic agents.

In a first aspect, the present invention provides an antibody or antigen binding fragment thereof, which binds to a complex of human GARP-TGF-β1, wherein the antibody or antigen binding fragment thereof comprises a heavy chain variable domain (VH) wherein:
the VH CDR3 comprises the amino acid sequence YEWETVVVGDLMYEYEY (SEQ ID NO: 13),
the VH CDR2 comprises the amino acid sequence RIDPEDAGTKYAQKFQG (SEQ ID NO: 12), and
the VH CDR1 comprises the amino acid sequence SYYID (SEQ ID NO: 4).

In certain embodiments, the present invention provides an antibody or antigen binding fragment thereof, which binds to a complex of human GARP-TGF-β1, wherein the antibody or antigen binding fragment thereof comprises a heavy chain variable domain (VH) wherein:
the VH CDR3 consists of the amino acid sequence YEWETVVVGDLMYEYEY (SEQ ID NO: 13),
the VH CDR2 consists of the amino acid sequence RIDPEDAGTKYAQKFQG (SEQ ID NO: 12), and
the VH CDR1 consists of the amino acid sequence SYYID (SEQ ID NO: 4).

The antibody or antigen binding fragment may additionally comprise a light chain variable domain (VL) wherein:
the VL CDR3 comprises the amino acid sequence QQYASVPVT (SEQ ID NO: 11),
the VL CDR2 comprises the amino acid sequence GASRLKT (SEQ ID NO: 10), and
the VL CDR1 comprises the amino acid sequence QASQSISSYLA (SEQ ID NO: 9).

In certain embodiments, the antibody or antigen binding fragment may additionally comprise a light chain variable domain (VL) wherein:
the VL CDR3 consists of the amino acid sequence QQYASVPVT (SEQ ID NO: 11),
the VL CDR2 consists of the amino acid sequence GASRLKT (SEQ ID NO: 10), and
the VL CDR1 consists of the amino acid sequence QASQSISSYLA (SEQ ID NO: 9).

In certain embodiments, the antibody or antigen binding fragment thereof comprises a heavy chain variable domain (VH), wherein:
the VH CDR3 comprises the amino acid sequence YEWETVVVGDLMYEYEY (SEQ ID NO: 13),
the VH CDR2 comprises the amino acid sequence RIDPEDAGTKYAQKFQG (SEQ ID NO: 12), and
the VH CDR1 comprises the amino acid sequence SYYID (SEQ ID NO: 4); and
a light chain variable domain (VL), wherein:
the VL CDR3 comprises the amino acid sequence QQYASVPVT (SEQ ID NO: 11),
the VL CDR2 comprises the amino acid sequence GASRLKT (SEQ ID NO: 10), and
the VL CDR1 comprises the amino acid sequence QASQSISSYLA (SEQ ID NO: 9).

In certain embodiments, the antibody or antigen binding fragment thereof comprises
a heavy chain variable domain (VH), wherein:
the VH CDR3 consists of the amino acid sequence YEWETVVVGDLMYEYEY (SEQ ID NO: 13),
the VH CDR2 consists of the amino acid sequence RIDPEDAGTKYAQKFQG (SEQ ID NO: 12), and
the VH CDR1 consists of the amino acid sequence SYYID (SEQ ID NO: 4); and
a light chain variable domain (VL), wherein:
the VL CDR3 consists of the amino acid sequence QQYASVPVT (SEQ ID NO: 11),
the VL CDR2 consists of the amino acid sequence GASRLKT (SEQ ID NO: 10), and
the VL CDR1 consists of the amino acid sequence QASQSISSYLA (SEQ ID NO: 9).

In certain embodiments, the antibodies or antigen binding fragments include at least one heavy chain variable domain (VH) and/or at least one light chain variable domain (VL) that is a humanised, germlined or affinity variant of a camelid-derived VH or VL domain.

In certain embodiments, provided herein are antibodies or antigen binding fragments thereof, which bind to the complex of human GARP and human TGF-β1, wherein the antibodies or antigen binding fragments comprise a heavy chain variable domain selected from the following:
  (i) a VH comprising or consisting of the amino acid sequence of SEQ ID NO: 14; or
  (ii) a VH comprising or consisting of an amino acid sequence having at least 90%, at least 95%, at least 97%, at least 98%, or at least 99% identity to SEQ ID NO:14.

Alternatively or in addition, the antibodies or antigen binding fragments may comprise a light chain variable domain (VL) selected from the following:
  (i) a VL comprising or consisting of the amino acid sequence of SEQ ID NO: 15; or
  (ii) a VL comprising or consisting of an amino acid sequence having at least 90%, at least 95%, at least 97%, at least 98%, or at least 99% identity to SEQ ID NO: 15.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

In a particular embodiment, provided herein are antibodies or antigen binding fragments thereof, wherein the heavy chain variable domain (VH) comprises or consists of the amino acid sequence of SEQ ID NO: 14 and the light chain variable domain (VL) comprises or consists of the amino acid sequence of SEQ ID NO: 15.

In certain embodiments, the antibodies of the invention include the CH1 domain, hinge region, CH2 domain and CH3 domain of a human antibody, in particular human IgG1, IgG2, IgG3 or IgG4. In certain embodiments, the antibody includes the CH3 region of a human IgG4 and includes the substitution S228P in the CH3 domain.

The antibodies which bind the GARP-TGF-β1 complex may comprise at least one full-length immunoglobulin heavy chain and/or at least one full-length lambda or kappa light chain. In certain embodiments, the antibodies comprise a heavy chain comprising the amino acid sequence of SEQ ID NO: 16 and a light chain comprising the amino acid sequence of SEQ ID NO: 17. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 16. In certain embodiments, provided herein are monoclonal antibodies comprising a light chain with at least 90%, at least 95%, at least 97%, at least 98%, or at least 99% sequence identity to the amino acid sequence shown as SEQ ID NO: 17. In certain embodiments, provided herein are monoclonal antibodies comprising a heavy chain with at least 90%, at least 95%, at least 97%, at least 98%, or at least 99% sequence identity to the amino acid sequence shown as SEQ ID NO: 16, and a light chain with at least 90%, at least 95%, at least 97%, at least 98%, or at least 99% sequence identity to the amino acid sequence shown as SEQ ID NO: 17.

For embodiments wherein the heavy and/or light chains of the antibodies are defined by a particular percentage sequence identity to a reference sequence, the heavy chain and/or light chain may retain identical CDR sequences to those present in the reference sequence such that the variation is present only outside the CDR regions.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

The GARP-TGF-β1 antibodies or antigen binding fragments thereof provided herein may each exhibit one or more of the following properties/features:

the antibody or antigen binding fragment may cross-react with the GARP-TGF-β complex of *Cynomolgus* origin;

the antibody or antigen binding fragment may bind to human GARP-TGF-β1 with high affinity;

the antibody or antigen binding fragment may include a VH domain and VL domain that when tested as a Fab fragment exhibit an off-rate ($K_{off}$) for the complex of human GARP and TGF-β1 of less than $5 \times 10^{-4}$ s$^{-1}$;

the antibody or antigen binding fragment may include a VH domain and VL domain that when tested as a Fab fragment exhibit an off-rate ($K_{off}$) for the complex of human GARP and TGF-β1 in the range $1 \times 10^{-6}$ s$^{-1}$ to $5 \times 10^{-4}$ s$^{-1}$;

the antibody or antigen binding fragment may include a VH domain and VL domain that when tested as a mAb exhibit a $K_D$ of less than $1.7 \times 10^{-9}$ M;

the antibody or antigen binding fragment may block release of active TGF-β1 from regulatory T cells.

In further aspects, the invention also provides polynucleotide molecules which encode the above-listed antibodies and antigen binding fragments, in addition to expression vectors comprising the polynucleotides, host cells containing the vectors, and methods of recombinant expression/production of the antibodies described herein.

In a still further aspect, the invention provides a pharmaceutical composition comprising any one of the GARP-TGF-β1 antibodies or antigen binding fragments thereof described herein, and a pharmaceutically acceptable carrier or excipient.

A still further aspect of the invention concerns methods of medical treatment using the above-listed GARP-TGF-β1 antibodies or antigen binding fragments thereof, particularly in the prophylaxis and/or treatment of TGF-β-related disorders. In certain embodiments, the invention relates to methods of treatment using the GARP-TGF-β1 antibodies or antigen binding fragments thereof, wherein the disease or condition to be treated is selected from the group consisting of inflammatory diseases, chronic infection, cancer, fibrosis, cardiovascular disease, cerebrovascular disease and neurodegenerative disease. In certain embodiments, the GARP-TGF-β1 antibodies or antigen binding fragments thereof are administered in combination with another treatment as part of a combination therapy. For example, the GARP-TGF-β1 antibodies or antigen binding fragments thereof may be administered in combination with an immunotherapeutic agent, optionally an immunostimulatory antibody or a tumour vaccine.

These and other embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

FIG. 3A: Western blots showing decreases in SMAD2 phosphorylation in the presence of different concentrations of the GARP-TGFβ antibodies 39B6-A, 39B6-AVE, 39B6-AEE, 39B6-AYE, 39B6-ANR and 39B6-ANK. FIG. 3B: Graphical representation of the data in (A) showing the percentage inhibition of SMAD2 phosphorylation at different antibody concentrations.

FIG. 8A: 39B6-AVE. FIG. 8B: 39B6-AYE. FIG. 8C: 39B6-ANK. FIG. 8D: 39B6-ANR. Markers appear at the centre of each gel. To the left of the markers, the 3 samples are (i) Ref; (ii) 5° C.; and (iii) 37° C. samples tested under non-reducing conditions and to the right of the markers, the 3 samples are (i) Ref; (ii) 5° C.; and (iii) 37° C. samples tested under reducing conditions.

FIG. 21 shows a gradient PCR device program for the thermal stability study.

DETAILED DESCRIPTION

A. Definitions

Figure 1:
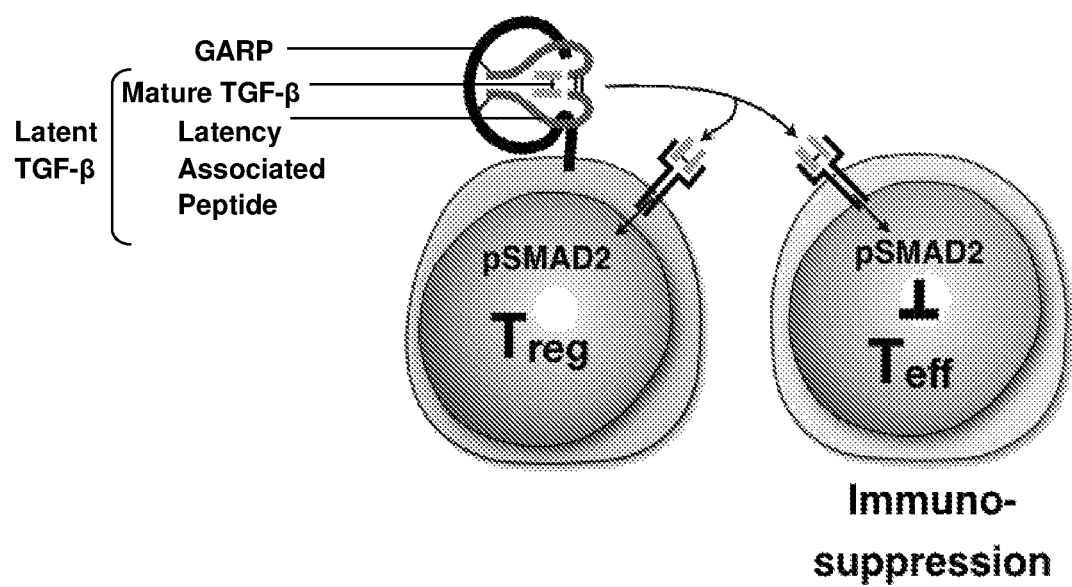
FIG. 1 is a schematic showing the binding of latent TGF-β to GARP on the surface of regulatory T cells. TGF-β is produced as a precursor, "pro-TGF-β" and undergoes cleavage to produce "latent-TGF-β", a form in which the mature TGF-β dimer remains non-covalently associated with the latency associated peptide (LAP) region of each polypeptide. It is this latent form that binds to GARP on the surface of Treg cells. Integrins αvβ6 and αvβ8 are thought to be responsible for mediating the release of mature or "active TGF-β" from the cell surface. This active form can act in a paracrine fashion to bring about effects in a variety of target cells, or can act as an autocrine mediator by binding to the TGF-β receptor on Treg cells.

"GARP"—GARP (Glycoprotein A Repetitions Predominant) is a member of the leucine-rich repeat family of proteins. It is also called Leucine Rich Repeat Containing 32 (LRRC32). GARP is an 80 kDa transmembrane protein with an extracellular region composed primarily of 20 leucine-rich repeats. The complete amino acid sequence of the human GARP protein transcript variant 2 (GenBank Accession No. NP_001122394) is:

```
                                           (SEQ ID NO: 33)
MRPQILLLLALLTLGLAAQHQDKVPCKMVDKKVSCQVLGLLQVPSVLPPD

TETLDLSGNQLRSILASPLGFYTALRHLDLSTNEISFLQPGAFQALTHLE

HLSLAHNRLAMATALSAGGLGPLPRVTSLDLSGNSLYSGLLERLLGEAPS

LHTLSLAENSLTRLTRHTFRDMPALEQLDLHSNVLMDIEDGAFEGLPRLT

HLNLSRNSLTCISDFSLQQLRVLDLSCNSIEAFQTASQPQAEFQLTWLDL

RENKLLHFPDLAALPRLIYLNLSNNLIRLPTGPPQDSKGIHAPSEGWSAL

PLSAPSGNASGRPLSQLLNLDLSYNEIELIPDSFLEHLTSLCFLNLSRNC

LRTFEARRLGSLPCLMLLDLSHNALETLELGARALGSLRTLLLQGNALRD

LPPYTFANLASLQRLNLQGNRVSPCGGPDEPGPSGCVAFSGITSLRSLSL

VDNEIELLRAGAFLHTPLTELDLSSNPGLEVATGALGGLEASLEVLALQG

NGLMVLQVDLPCFICLKRLNLAENRLSHLPAWTQAVSLEVLDLRNNSFSL

LPGSAMGGLETSLRRLYLQGNPLSCCGNGWLAAQLHQGRVDVDATQDLIC

RFSSQEEVSLSHVRPEDCEKGGLKNINLIIILTFILVSAILLTTLAACCC

VRRQKFNQQYKA.
```

"TGF-β"-TGF-β is a cytokine belonging to a superfamily of growth factors. There are three distinct isoforms of TGF-β (TGF-β1, TGF-β2 and TGF-β3) encoded by three distinct genes, but the overall structures of the TGF-β isoforms are highly similar, with homologies in the order of 70-80%. The term TGF-β, as used herein, is typically used to encompass all three different isoforms of the TGF-β cytokine, unless the context indicates otherwise.

All three TGF-β isoforms are encoded as large protein precursors; TGF-β1 (GenBank Accession No: NM_000660) contains 390 amino acids, and TGF-β2 (GenBank Accession Nos: NM_001135599 and NM_003238) and TGF-β3 (GenBank Accession No: XM_005268028) each contain 412 amino acids. They each have an N-terminal signal peptide of 20-30 amino acids that is required for secretion from a cell, a pro-region (named latency associated peptide or LAP), and a 112-114 amino acid C-terminal region that becomes the mature TGF-β molecule following its release from the pro-region by proteolytic cleavage. After proteolytic cleavage, LAP and mature TGF-β remain non-covalently associated and form the "latent TGF-β" molecule. In this latent form, mature TGF-β is prevented from binding to the TGF-β receptor by LAP. To exert a signal, mature TGF-β must be released from LAP. Mature TGF-β that is not associated to LAP is called active TGF-β, as it can bind to the TGF-β receptor and transduce a signal.

Full length TGF-β1 has the following amino acid sequence:

```
                                           (SEQ ID NO: 34)
MPPSGLRLLPLLLPLLWLLVLTPGRPAAGLSTCKTIDMELVKRKRIEAIR

GQILSKLRLASPPSQGEVPPGPLPEAVLALYNSTRDRVAGESAEPEPEPE

ADYYAKEVTRVLMVETHNEIYDKFKQSTHSIYMFFNTSELREAVPEPVLL

SRAELRLLRLKLKVEQHVELYQKYSNNSWRYLSNRLLAPSDSPEWLSFDV

TGVVRQWLSRGGEIEGFRLSAHCSCDSRDNTLQVDINGFTTGRRGDLATI

HGMNRPFLLLMATPLERAQHLQSSRHRRALDTNYCFSSTEKNCCVRQLYI

DFRKDLGWKWIHEPKGYHANFCLGPCPYIWSLDTQYSKVLALYNQHNPGA

SAAPCCVPQALEPLPIVYYVGRKPKVEQLSNMIVRSCKCS.
```

LAP has the following amino acid sequence:

```
                                           (SEQ ID NO: 35)
LSTCKTIDMELVKRKRIEAIRGQILSKLRLASPPSQGEVPPGPLPEAVLA

LYNSTRDRVAGESAEPEPEPEADYYAKEVTRVLMVETHNEIYDKFKQSTH

SIYMFFNTSELREAVPEPVLLSRAELRLLRLKLKVEQHVELYQKYSNNSW

RYLSNRLLAPSDSPEWLSFDVTGVVRQWLSRGGEIEGFRLSAHCSCDSRD

NTLQVDINGFTTGRRGDLATIHGMNRPFLLLMATPLERAQHLQSSRHRR.
```

Mature TGF-β1 has the following amino acid sequence:

```
                                           (SEQ ID NO: 36)
ALDTNYCFSSTEKNCCVRQLYIDFRKDLGWKWIHEPKGYHANFCLGPCPY

IWSLDTQYSKVLALYNQHNPGASAAPCCVPQALEPLPIVYYVGRKPKVEQ

LSNMIVRSCKCS.
```

"GARP-TGF-β complex"—As used herein, the GARP-TGF-β complex means the native complex that forms when latent TGF-β binds to GARP, particularly GARP located on the surface of Treg cells. Although not specified throughout, the "GARP-TGF-β complex," or simply "GARP-TGF-β," as used herein, is intended to mean the complex between GARP and latent TGF-β. The binding of GARP to TGF-β, more specifically latent TGF-β, has been characterised at the molecular level, for example as reported in Wang et al. Mol Biol Cell. 2012 March; 23(6):1129-39. GARP forms a disulphide linkage to the Cys4 of latent TGF-β and also associates with latent TGF-3 through non-covalent interactions. There are 15 Cys residues in the extracellular domain of GARP, and GARP uses Cys-192 and Cys-331 to form disulphide linkages to the two Cys4 residues of latent TGF-β. It follows that one GARP protein associates with one latent TGF-β dimer.

"Antibody" or "Immunoglobulin"—As used herein, the term "immunoglobulin" includes a polypeptide having a combination of two heavy and two light chains whether or not it possesses any relevant specific immunoreactivity. "Antibodies" refer to such assemblies which have significant specific immunoreactive activity to an antigen of interest (e.g. the complex of GARP and TGF-β). The term "GARP-TGF-β antibodies" is used herein to refer to antibodies which exhibit immunological specificity for the complex of GARP and TGF-β1, particularly the human GARP-TGF-β1 complex and in some cases species homologues thereof. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody (IgG, IgM, IgA, IgD or IgE) that can be distinguished biochemically. All five classes of antibodies are within the scope of the present invention. The following discussion will generally be directed to the IgG class of immunoglobulin molecules. With regard to IgG, immunoglobulins typically comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

"Binding Site"—As used herein, the term "binding site" comprises a region of a polypeptide which is responsible for selectively binding to a target antigen of interest. Binding domains comprise at least one binding site. Exemplary binding domains include an antibody variable domain. The antibody molecules of the invention may comprise a single binding site or multiple (e.g., two, three or four) binding sites.

"Variable region" or "variable domain"—The terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Constant region"—As used herein, the term "constant region" refers to the portion of the antibody molecule outside of the variable domains or variable regions. Immunoglobulin light chains have a single domain "constant region", typically referred to as the "CL or CL1 domain".

This domain lies C terminal to the VL domain. Immunoglobulin heavy chains differ in their constant region depending on the class of immunoglobulin (γ, μ, α, δ, ε). Heavy chains γ, α and δ have a constant region consisting of three immunoglobulin domains (referred to as CH1, CH2 and CH3) with a flexible hinge region separating the CH1 and CH2 domains. Heavy chains μ and ε have a constant region consisting of four domains (CH1-CH4). The constant domains of the heavy chain are positioned C terminal to the VH domain. The numbering of the amino acids in the heavy and light immunoglobulin chains run from the N-terminus at the forked ends of the Y configuration to the C-terminus at the bottom of each chain. Different numbering schemes are used to define the constant domains of the immunoglobulin heavy and light chains. In accordance with the EU numbering scheme, the heavy chain constant domains of an IgG molecule are identified as follows: CH1—amino acid residues 118-215; CH2—amino acid residues 231-340; CH3—amino acid residues 341-446. In accordance with the Kabat numbering scheme, the heavy chain constant domains of an IgG molecule are identified as follows: CH1—amino acid residues 114-223; CH2—amino acid residues 244-360; CH3—amino acid residues 361-477. The "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 2 below.

TABLE 2

| Human hinge sequences | | | |
|---|---|---|---|
| IgG | Upper hinge | Middle hinge | Lower hinge |
| IgG1 | EPKSCDKTHT (SEQ ID NO: 37) | CPPCP (SEQ ID NO: 38) | APELLGGP (SEQ ID NO: 39) |
| IgG3 | ELKTPLGDTTHT (SEQ ID NO: 40) | CPRCP (EPKSCDTPPPCPRCP)$_3$ (SEQ ID NO: 41) | APELLGGP (SEQ ID NO: 42) |

TABLE 2-continued

Human hinge sequences

| IgG | Upper hinge | Middle hinge | Lower hinge |
|---|---|---|---|
| IgG4 | ESKYGPP (SEQ ID NO: 43) | CPSCP (SEQ ID NO: 44) | APEFLGGP (SEQ ID NO: 45) |
| IgG2 | ERK (SEQ ID NO: 46) | CCVECPPPCP (SEQ ID NO: 47) | APPVAGP (SEQ ID NO: 48) |

"Fragment"—The term "fragment", as used in the context of antibodies of the invention, refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to the GARP-TGF-β complex). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a one-armed (monovalent) antibody, diabodies, triabodies, tetrabodies or any antigen-binding molecule formed by combination, assembly or conjugation of such antigen binding fragments. The term "antigen binding fragment" as used herein is further intended to encompass antibody fragments selected from the group consisting of unibodies, domain antibodies and nanobodies. Fragments can be obtained, e.g., via chemical or enzymatic treatment of an intact or complete antibody or antibody chain or by recombinant means.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family. In another embodiment, a string of amino acids can be replaced with a structurally similar string that differs in order and/or composition of side chain family members.

"Chimeric"—A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric antibodies of the invention include fusion proteins comprising camelid-derived VH and VL domains, or humanised variants thereof, fused to the constant domains of a human antibody, e.g. human IgG1, IgG2, IgG3 or IgG4.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

"Specificity"—The term "specificity" refers to the ability to bind (e.g., immunoreact with) a given target, e.g., a complex of GARP-TGF-β. A polypeptide may be monospecific and contain one or more binding sites which specifically bind a target or a polypeptide may be multispecific and contain two or more binding sites which specifically bind the same or different targets.

"Synthetic"—As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Humanising substitutions"—As used herein, the term "humanising substitutions" refers to amino acid substitutions in which the amino acid residue present at a particular position in the VH or VL domain of an antibody (for example a camelid-derived GARP-TGF-β1 antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" is used herein to refer specifically to "humanised variants" in which the "humanising substitutions" result in replacement of one or more amino acid residues present at a particular position (s) in the VH or VL domain of an antibody (for example a camelid-derived GARP-TGF-β1 antibody) with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably herein. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for GARP-TGF-β, as compared to the reference GARP-TGF-β antibody. Preferably the affinity variant will exhibit improved affinity for the target antigen, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

B. GARP-TGF-β1 Antibodies

The present invention relates to antibodies and antigen binding fragments thereof, which specifically bind to the complex of GARP and TGF-β1, particularly the complex of human GARP and human TGF-β1. The antibodies and antigen binding fragments of the present invention may be defined with respect to structural and functional characteristics as described herein.

Importantly, the GARP-TGF-β1 antibodies of the invention are improved as compared with the GARP-TGF-β1 antibodies described previously, for the reason that they display improved stability. In particular, the stability of the GARP-TGF-β1 antibodies described herein is improved as compared with antibodies having the heavy chain and light chain CDR sequences of the GARP-TGF-β1 reference antibodies LHG-10 and LHG-10.6, described in WO2015/015003 and WO2016/125017. This improvement in stability is achieved without a significant decrease in the binding affinity of the antibodies for the GARP-TGF-β1 complex, as compared with the reference LHG10 and LHG10.6 antibodies.

The antibodies of the present invention differ from the LHG-10 and LHG-10.6 GARP-TGF-β1 reference antibodies described previously particularly with respect to the sequences of the heavy chain CDR2 and CDR3 sequences. More specifically, the LHG-10 and LHG-10.6 GARP-TGF-β1 antibodies possess the heavy chain CDR2 sequence: RIDPEDGGTKYAQKFQG (SEQ ID NO: 5) and the heavy chain CDR3 sequence: NEWETVVVGDLMYEYEY (SEQ ID NO: 6), whereas the antibodies of the present invention comprise the heavy chain CDR2 sequence: RIDPEDAGTKYAQKFQG (SEQ ID NO: 12) and the heavy chain CDR3 sequence: YEWETVVVGDLMYEYEY (SEQ ID NO:13).

As described and exemplified herein, the G55A and N95Y amino acid substitutions in the heavy chain CDR2 and CDR3 sequences, respectively, were found to improve antibody stability by reducing deamidation, isomerization and oxidation, whilst achieving a binding affinity for the GARP-TGF-β1 complex approximately equivalent to that of the reference antibodies.

In a first aspect, the present invention provides antibodies or antigen binding fragments thereof, which bind to a complex of GARP and TGF-β1, and comprise a heavy chain variable domain (VH) wherein:
the VH CDR3 comprises or consists of the amino acid sequence YEWETVVVGDLMYEYEY (SEQ ID NO: 13),
the VH CDR2 comprises or consists of the amino acid sequence RIDPEDAGTKYAQKFQG (SEQ ID NO: 12), and
the VH CDR1 comprises or consists of the amino acid sequence SYYID (SEQ ID NO: 4).

In certain embodiments, the antibodies or antigen binding fragments thereof additionally comprise a light chain variable domain (VL), wherein:
the VL CDR3 comprises or consists of the amino acid sequence QQYASVPVT (SEQ ID NO: 11),
the VL CDR2 comprises or consists of the amino acid sequence GASRLKT (SEQ ID NO: 10), and
the VL CDR1 comprises or consists of the amino acid sequence QASQSISSYLA (SEQ ID NO: 9).

In certain embodiments, provided herein are antibodies or antigen binding fragments thereof, which specifically bind the GARP-TGF-β1 complex, wherein the antibodies or antigen binding fragments thereof comprise at least one heavy chain variable domain (VH) and at least one light chain variable domain (VL), wherein:
the VH CDR3 comprises or consists of the amino acid sequence YEWETVVVGDLMYEYEY (SEQ ID NO: 13),
the VH CDR2 comprises or consists of the amino acid sequence RIDPEDAGTKYAQKFQG (SEQ ID NO: 12),
the VH CDR1 comprises or consists of the amino acid sequence SYYID (SEQ ID NO: 4),
the VL CDR3 comprises or consists of the amino acid sequence QQYASVPVT (SEQ ID NO: 11),
the VL CDR2 comprises or consists of the amino acid sequence GASRLKT (SEQ ID NO: 10), and
the VL CDR1 comprises or consists of the amino acid sequence QASQSISSYLA (SEQ ID NO: 9).

In certain embodiments, provided herein are antibodies or antigen binding fragments thereof, which specifically bind the GARP-TGF-β1 complex, wherein the antibodies or antigen binding fragments thereof comprise at least one heavy chain variable domain (VH) and at least one light chain variable domain (VL), wherein:
the VH CDR3 consists of the amino acid sequence YEWETVVVGDLMYEYEY (SEQ ID NO: 13),
the VH CDR2 consists of the amino acid sequence RIDPEDAGTKYAQKFQG (SEQ ID NO: 12),
the VH CDR1 consists of the amino acid sequence SYYID (SEQ ID NO: 4),
the VL CDR3 consists of the amino acid sequence QQYASVPVT (SEQ ID NO: 11),
the VL CDR2 consists of the amino acid sequence GASRLKT (SEQ ID NO: 10), and
the VL CDR1 consists of the amino acid sequence QASQSISSYLA (SEQ ID NO: 9).

In certain embodiments, the antibodies and antigen binding fragments are recombinant. In certain embodiments, the antibodies and antigen binding fragments are monoclonal.

The term "antibody" herein is used in the broadest sense and encompasses, but is not limited to, monoclonal antibodies (including full length monoclonal antibodies), polyclonal antibodies, and multispecific antibodies (e.g., bispecific antibodies), so long as they exhibit the appropriate immunological specificity for the GARP-TGF-β1 complex. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

The present invention also encompasses "antigen binding fragments" of antibodies, and such fragments are defined elsewhere herein. Antibody fragments typically comprise a portion of a full length antibody, generally the antigen binding or variable domain thereof. Examples of antibody fragments include Fab, Fab', F(ab')2, bi-specific Fab's, and Fv fragments, linear antibodies, single-chain antibody molecules, a single chain variable fragment (scFv) and multispecific antibodies formed from antibody fragments (see Holliger and Hudson, Nature Biotechnol. 23:1126-36 (2005)).

The antibodies and antigen binding fragments of the present invention may exhibit high human homology. The level of homology with human sequence may be assessed across the length of the heavy chain variable domain (VH) and/or across the length of the light chain variable domain (VL). In the context of the present invention, an antibody comprising a heavy chain variable domain (VH) and a light chain variable domain (VL) may be considered as having high human homology if the VH domains and the VL domains, taken together, exhibit at least 90%, at least 92%, at least 94%, or at least 96% amino acid sequence identity to the closest matching human germline VH and VL sequences. In one embodiment the VH domain of the antibody with high human homology may exhibit an amino acid sequence identity or sequence homology of at least 90%, at least 92%, at least 94%, or at least 96% with one or more human VH domains across the framework regions FR1, FR2, FR3 and FR4. In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence.

In another embodiment the VL domain of the antibody with high human homology may exhibit a sequence identity or sequence homology of at least 90%, at least 92%, at least 94%, or at least 96% with one or more human VL domains across the framework regions FR1, FR2, FR3 and FR4. In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

Antibodies and antigen binding fragments of the present having high human homology may include antibodies comprising VH and VL domains of native non-human antibodies which exhibit sufficiently high % sequence identity to human germline sequences. In certain embodiments, the antibodies and antigen binding fragments of the invention are humanised or germlined variants of non-human antibodies, for example antibodies comprising VH and VL domains of camelid conventional antibodies engineered so as to be humanised, or germlined variants of the original antibodies.

The antibodies or antigen binding fragments thereof may comprise a heavy chain variable domain (VH) comprising or consisting of the amino acid sequence of SEQ ID NO: 14 and optionally a light chain variable domain (VL) comprising or consisting of the amino acid sequence of SEQ ID NO: 15.

In certain embodiments, the antibodies or antigen binding fragments thereof may comprise a heavy chain variable domain (VH) comprising the amino acid sequence of SEQ ID NO: 14. In certain embodiments, the antibodies or antigen binding fragments thereof may comprise a light chain variable domain (VL) comprising the amino acid sequence of SEQ ID NO: 15.

In certain embodiments, the antibodies or antigen binding fragments thereof may comprise a heavy chain variable domain (VH) consisting of the amino acid sequence of SEQ ID NO: 14. In certain embodiments, the antibodies or antigen binding fragments thereof may comprise a light chain variable domain (VL) consisting of the amino acid sequence of SEQ ID NO: 15.

In certain embodiments, the antibodies or antigen binding fragments thereof may comprise a heavy chain variable domain (VH) comprising the amino acid sequence of SEQ ID NO: 14 and a light chain variable domain (VL) comprising the amino acid sequence of SEQ ID NO: 15.

In certain embodiments, the antibodies or antigen binding fragments thereof may comprise a heavy chain variable domain (VH) consisting of the amino acid sequence of SEQ ID NO: 14 and a light chain variable domain (VL) consisting of the amino acid sequence of SEQ ID NO: 15.

In certain embodiments, provided herein are monoclonal antibodies or antigen binding fragments thereof, comprising a heavy chain variable domain and a light chain variable domain, the heavy chain variable domain comprising a VH sequence with at least 90%, at least 95%, at least 97%, at least 98%, or at least 99% sequence identity to the amino acid sequence shown as SEQ ID NO: 14 and/or the light chain variable domain comprising a VL with at least 90%, at least 95%, at least 97%, at least 98%, or at least 99% sequence identity to the amino acid sequence shown as SEQ ID NO: 15.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions. In certain embodiments, the antibodies or antigen binding fragments comprising heavy chain variable domains and/or light chain variable domains defined as having a particular percentage identity to SEQ ID NOs: 14 and 15, respectively, will have the following CDR sequences:
a VH CDR3 comprising or consisting of the amino acid sequence YEWETVVVGDLMYEYEY (SEQ ID NO: 13),
a VH CDR2 comprising or consisting of the amino acid sequence RIDPEDAGTKYAQKFQG (SEQ ID NO: 12),
a VH CDR1 comprising or consisting of the amino acid sequence SYYID (SEQ ID NO: 4),
a VL CDR3 comprising or consisting of the amino acid sequence QQYASVPVT (SEQ ID NO: 11),
a VL CDR2 comprising or consisting of the amino acid sequence GASRLKT (SEQ ID NO: 10), and a VL CDR1 comprising or consisting of the amino acid sequence QASQSISSYLA (SEQ ID NO: 9).

In non-limiting embodiments, the antibodies of the present invention may comprise CH1 domains and/or CL domains (from the heavy chain and light chain, respectively), the amino acid sequence of which is fully or substantially human. Where the antibody or antigen binding fragment of the invention is an antibody intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the GARP-TGF-431 antibodies of the invention may be beneficial both to minimise immunogenicity and to optimise stability of the antibody.

As discussed elsewhere herein, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites).

The GARP-TGF-β1 antibodies may be modified within the Fc region to increase binding affinity for the neonatal receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to the unmodified Fc region. Typically the unmodified Fc region will possess the wild-type amino acid sequence of human IgG1, IgG2, IgG3 or IgG4. In such embodiments, the increased FcRn binding affinity of the antibody molecule having the modified Fc region will be measured relative to the binding affinity of wild-type IgG1, IgG2, IgG3 or IgG4 for FcRn.

In certain embodiments, one or more amino acid residues within the Fc region may be substituted with a different amino acid so as to increase binding to FcRn. Several Fc substitutions have been reported that increase FcRn binding and thereby improve antibody pharmacokinetics. Such substitutions are reported in, for example, Zalevsky et al. (2010) *Nat. Biotechnol.* 28(2):157-9; Hinton et al. (2006) *J Immunol.* 176:346-356; Yeung et al. (2009) *J Immunol.* 182:7663-7671; Presta L G. (2008) *Curr. Op. Immunol.* 20:460-470; and Vaccaro et al. (2005) *Nat. Biotechnol.* 23(10):1283-88, the contents of which are incorporated herein in their entirety.

In certain embodiments, the GARP-TGF-β1 antibodies comprise a modified human IgG Fc domain comprising or consisting of the amino acid substitutions H433K and N434F, wherein the Fc domain numbering is in accordance with EU numbering. In a further embodiment, the GARP-TGF-β1 antibodies described herein comprise a modified human IgG Fc domain comprising or consisting of the amino acid substitutions M252Y, S254T, T256E, H433K and N434F, wherein the Fc domain numbering is in accordance with EU numbering.

In certain embodiments, the GARP-TGF-β1 antibodies comprise a modified human IgG Fc domain consisting of up to 2, up to 3, up to 4, up to 5, up to 6, up to 7, up to 8, up to 9, up to 10, up to 12, up to 15, up to 20 substitutions relative to the corresponding wild-type IgG sequence.

Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148: 2918-2922 (1992). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, Nature Reviews: Immunology, Vol. 10, pp 301-316, 2010, incorporated herein by reference.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids.

In particular embodiments, the Fc region may be engineered such that there is no effector function. A GARP-TGF-β1 antibody having no Fc effector function may be particularly useful as a receptor blocking agent. In certain embodiments, the antibodies of the invention may have an Fc region derived from naturally-occurring IgG isotypes having reduced effector function, for example IgG4. Fc regions derived from IgG4 may be further modified to increase therapeutic utility, for example by the introduction of modifications that minimise the exchange of arms between IgG4 molecules in vivo. Fc regions derived from IgG4 may be modified to include the S228P substitution.

In still another embodiment, the glycosylation of an antibody is modified. For example, an aglycosylated antibody can be made (i.e., the antibody lacks glycosylation). Glycosylation can be altered to, for example, increase the affinity of the antibody for the target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Also envisaged are variant GARP-TGF-β1 antibodies having an altered type of glycosylation, such as a hypofucosylated antibody having reduced amounts of fucosyl residues or a fully or partially de-fucosylated antibody (as described by Natsume et al., Drug Design Development and Therapy, Vol. 3, pp 7-16, 2009) or an antibody having increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, mAbs 1:3, 230-236, 2009). Examples of non-fucosylated antibodies with enhanced ADCC function are those produced using the Potelligent® technology of BioWa Inc.

Antibodies intended for human therapeutic use will typically be of the IgG, IgM, IgA, IgD, or IgE type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

In certain embodiments, the antibodies which specifically bind GARP-TGF-β1 comprise at least one full-length immunoglobulin heavy chain and/or at least one full-length lambda or kappa light chain, wherein the heavy chain comprises or consists of the amino acid sequence of SEQ ID NO:16 and the light chain comprises or consists of the amino acid sequence of SEQ ID NO:17.

In certain embodiments, the antibodies which specifically bind GARP-TGF-β1 comprise at least one full-length immunoglobulin heavy chain and/or at least one full-length lambda or kappa light chain, wherein the heavy chain comprises the amino acid sequence of SEQ ID NO:16 and the light chain comprises the amino acid sequence of SEQ ID NO:17.

In certain embodiments, the antibodies which specifically bind GARP-TGF-β1 comprise at least one full-length immunoglobulin heavy chain and/or at least one full-length lambda or kappa light chain, wherein the heavy chain consists of the amino acid sequence of SEQ ID NO:16 and the light chain consists of the amino acid sequence of SEQ ID NO:17.

In certain embodiments, provided herein are monoclonal antibodies comprising a heavy chain with at least 90%, at least 95%, at least 97%, at least 98%, or at least 99% sequence identity to the amino acid sequence shown as SEQ ID NO:16, and/or a light chain with at least 90%, at least 95%, at least 97%, at least 98%, or at least 99% sequence identity to the amino acid sequence shown as SEQ ID NO:17.

In certain embodiments, provided herein are monoclonal antibodies comprising a heavy chain with at least 90%, at least 95%, at least 97%, at least 98%, or at least 99% sequence identity to the amino acid sequence shown as SEQ ID NO:16. In certain embodiments, provided herein are monoclonal antibodies comprising a light chain with at least 90%, at least 95%, at least 97%, at least 98%, or at least 99% sequence identity to the amino acid sequence shown as SEQ ID NO:17. In certain embodiments, provided herein are monoclonal antibodies comprising a heavy chain with at least 90%, at least 95%, at least 97%, at least 98%, or at least 99% sequence identity to the amino acid sequence shown as SEQ ID NO:16, and a light chain with at least 90%, at least 95%, at least 97%, at least 98%, or at least 99% sequence identity to the amino acid sequence shown as SEQ ID NO:17.

For embodiments wherein the chains of the antibodies are defined by a particular percentage sequence identity to a reference sequence, the heavy chain and/or light chain may retain identical CDR sequences to those present in the reference sequence such that the variation is present only outside the CDR regions. In particular, the antibodies or antigen binding fragments comprising heavy chains and/or light chains defined as having a particular percentage identity to SEQ ID NOs: 16 and 17, respectively, may have the following CDR sequences:
a VH CDR3 comprising or consisting of the amino acid sequence YEWETVVVGDLMYEYEY (SEQ ID NO: 13),
a VH CDR2 comprising or consisting of the amino acid sequence RIDPEDAGTKYAQKFQG (SEQ ID NO: 12),
a VH CDR1 comprising or consisting of the amino acid sequence SYYID (SEQ ID NO: 4),
a VL CDR3 comprising or consisting of the amino acid sequence QQYASVPVT (SEQ ID NO: 11), and
a VL CDR2 sequence comprising or consisting of SEQ ID NO: 10 [GASRLKT] and
a VL CDR1 comprising or consisting of the amino acid sequence QASQSISSYLA (SEQ ID NO: 9).

Binding to GARP-TGF-β1

The antibodies and antigen binding fragments of the present invention bind to a complex of GARP and TGF-β1, particularly a complex of human GARP and human TGF-β1. As explained elsewhere herein, GARP is a transmembrane protein expressed on the surface of regulatory T cells and acts as the receptor for the latent form of TGF-β. FIG. 1 includes a schematic representation of the complex that forms between GARP and latent TGF-β at the cell surface of regulatory T cells.

The GARP-TGF-β1 complex to which the antibodies and antigen binding fragments of the present invention bind is the native GARP-TGF-β1 complex that forms at the cell surface between GARP and TGF-β1.

The antibodies and antigen binding fragments of the present invention are characterised in that they bind to the complex of GARP-TGF-β1 but do not bind to GARP in the absence of TGF-β1 or latent TGF-β. The antibodies and antigen binding fragments bind to GARP only in the presence of TGF-β1. In particular, the antibodies and antigen binding fragments bind to GARP only in the presence of latent TGF-β1.

Since the target antigen for the antibodies and antigen binding fragments thereof of the present invention is a complex comprising two separate proteins, the epitope to which the antibodies and antigen binding fragments bind is a conformational, as opposed to a linear, epitope. The conformational epitope comprises at least one residue from GARP and at least one residue from latent TGF-β1. In preferred embodiments, the conformational epitope comprises at least one residue from GARP, at least one residue from the latency associated peptide (LAP) of latent TGF-β1 and at least one residue from mature TGF-β1.

The antibodies and antigen binding fragments of the present invention may bind to an epitope of a complex formed by human GARP and human TGF-β1 wherein the epitope comprises at least one residue from GARP selected from Y137, S138, G139, T162 and R163 (with reference to SEQ ID NO: 33), and at least one residue from TGF-β1. In preferred embodiments, the epitope comprises at least residues Y137, S138, G139, T162 and R163 of GARP (with reference to SEQ ID NO:33).

The epitope may comprise at least one residue from the TGF-β1 polypeptide (SEQ ID NO: 34), optionally wherein the at least one residue is K338. The epitope may comprise at least one residue from the latency associated peptide (LAP) of TGF-β1 and at least one residue from mature TGF-β1. The epitope may comprise R58 of LAP and K338 of mature TGF-β1 (with reference to SEQ ID NO: 34).

The antibodies and antigen binding fragments of the present invention bind to a complex of GARP and TGF-β1. The antibodies and antigen binding fragments of the present invention may additionally bind to a complex of human GARP and human TGF-β2 and/or a complex of human GARP and human TGF-β3.

In certain embodiments, antibodies and antigen binding fragments of the invention bind to the complex of GARP and TGF-β1 with high affinity. As used herein, the term "affinity" or "binding affinity" should be understood based on the usual meaning in the art in the context of antibody binding, and reflects the strength and/or stability of binding between an antigen and a binding site on an antibody or antigen binding fragment thereof.

The binding affinity of an antibody or antigen binding fragment thereof for its respective antigen can be determined experimentally using techniques known in the art. For example, SPR instruments such as Biacore™ measure affinity based on the immobilization of a target protein or antigen on a biosensor chip while the antibody or antibody fragment is passed over the immobilized target under specific flow conditions. These experiments yield $k_{on}$ and $k_{off}$ measurements, which can be translated into $K_D$ values, wherein $K_D$ is the equilibrium constant for the dissociation of an antigen with an antibody or fragment thereof. The smaller the $K_D$ value, the stronger the binding interaction between an antibody and its target antigen.

As noted above, the affinity of an antibody may be determined by SPR, for example using the protocol described elsewhere herein. The affinity of the antibody or antigen binding fragment for the GARP-TGF-β1 complex, as measured by SPR, may be determined using recombinantly expressed GARP-TGF-β1 complex, as described for example, in Example 2.

The GARP-TGF-β1 antibodies or antigen binding fragments thereof of the invention may exhibit an off-rate ($k_{off}$) for the GARP-TGF-431 complex of less than $7 \times 10^{-4}$ s$^{-1}$, less than $5 \times 10^{-4}$ s$^{-1}$, less than $3 \times 10^{-4}$ s$^{-1}$, less than $1.5 \times 10^{-4}$ s$^{-1}$ when tested as a Fab. The GARP-TGF-β antibodies or antigen binding fragments thereof of the invention may exhibit an off-rate ($k_{off}$) for the complex of GARP-TGF-β1 in the range from $1 \times 10^{-6}$ s$^{-1}$ to $5 \times 10^{-4}$ s$^{-1}$, preferably in the range from $1 \times 10^{-6}$ s$^{-1}$ to $3 \times 10^{-4}$ s$^{-1}$, more preferably in the range from $1 \times 10^{-5}$ s$^{-1}$ to $1.5 \times 10^{-4}$ s$^{-1}$.

The GARP-TGF-β1 antibodies of the invention may exhibit a $K_D$ value less than $5 \times 10^{-9}$ M, less than $2 \times 10^{-9}$ M. In preferred embodiments, the GARP-TGF-431 antibodies of the invention exhibit a $K_D$ value less than $1.7 \times 10^{-9}$ M.

In certain embodiments, the antibodies or antigen binding fragments described herein that bind to the complex of GARP and TGF-β1 may cross-react with one or more species homologs of GARP and TGF-β, for example GARP and TGF-β homologs of non-human primate origin.

In certain embodiments, the antibodies or antigen binding fragments of the present invention do not cross-react with the complex of GARP and TGF-β of murine origin. Alternatively or in addition, the antibodies or antigen binding fragments may bind to the GARP-TGF-β complex of non-human primate origin, particularly the GARP-TGF-β complex of *cynomolgus* origin. The cross-reactivity with other species homologs can be particularly advantageous in the development and testing of therapeutic antibodies. For example, pre-clinical toxicology testing of therapeutic antibodies is frequently carried out in primate species including but not limited to *cynomolgus* monkeys. Cross-reactivity with these species homologs can therefore be particularly advantageous for the development of antibodies as clinical candidates.

Improved Stability

The GARP-TGF-β1 antibodies of the invention are improved as compared with GARP-TGF-β1 antibodies described previously, for the reason that they display improved stability. In particular, the stability of the GARP-TGF-β1 antibodies is improved as compared with antibodies having the heavy chain and light chain CDR sequences of the GARP-TGF-β1 reference antibody LHG10.6, described in WO2015/015003 and WO2016/125017.

The GARP-TGF-β antibody LHG10.6 possesses the following combination of heavy chain variable domain and light chain variable domain CDR sequences:

```
heavy chain CDR3 consisting of
NEWETVVVGDLMYEYEY,        (SEQ ID NO: 6)

heavy chain CDR2 consisting of
RIDPEDGGTKYAQKFQG,        (SEQ ID NO: 5)

heavy chain CDR1 consisting of
SYYID,                    (SEQ ID NO: 4)

light chain CDR3 consisting of
QQYASVPVT,                (SEQ ID NO: 11)

light chain CDR2 consisting of
GASRLKT,                  (SEQ ID NO: 10)
and light chain CDR1 consisting of
QASQSISSYLA.              (SEQ ID NO: 9)
```

As reported elsewhere herein, it has been found that GARP-TGF-β1 antibodies having the heavy chain and light chain CDR sequences of LHG10.6 lack stability. In particular, germlined monoclonal antibody variants of LHG10.6 (referred to elsewhere herein as mAb 3966 IgG4 and 39B6 IgG1) were found to exhibit a trend towards lower target binding activity when stored at 37° C. in both PBS and PBS/Tween (see for example, FIG. 2). This instability was attributed at least in part to the isomerization and deamidation at position N95 of HCDR3, i.e. the first residue of heavy chain CDR3.

The GARP-TGF-β1 antibodies and antigen binding fragments of the present invention differ with respect to their CDR sequences, particularly their heavy chain CDR sequences, such that their stability is improved. In particular, the heavy chain CDR2 (HCDR2 or VH CDR2) sequence is modified to include a G55A substitution, such that the HCDR2 sequence of the antibodies of the invention comprises the HCDR2 represented by RIDPEDAGTKYAQKFQG (SEQ ID NO: 12). In addition, the heavy chain CDR3 (HCDR3 or VH CDR3) sequence is modified to include a N95Y substitution, such that the HCDR3 sequence of the antibodies of the invention comprises HCDR3 represented by YEWETWVGDLMYEYEY (SEQ ID NO: 13). The antibodies of the present invention do not undergo deamidation or isomerization. In addition, it has surprisingly been found that the GARP-TGF-β1 antibodies of the present invention are relatively resistant to oxidation. This resistance to deamidation, isomerization and oxidation correlates with improved stability of the antibodies of the invention, particularly improved stability as measured at a temperature of 37° C.

Furthermore, the antibodies and antigen binding fragments of the invention are surprisingly advantageous because the modifications to the heavy chain CDR2 and CDR3 sequences, as compared with the reference antibody LHG10.6, do not significantly decrease target binding activity. As exemplified herein, the GARP-TGF-β1 antibodies of the present invention are relatively stable at 37° C. and do not exhibit a significant reduction in binding affinity for the GARP-TGF-β1 complex as compared with the reference antibody LHG10.6 or a germlined variant thereof (3966). As described elsewhere, in preferred embodiments, the GARP-TGF-β1 antibodies of the invention exhibit a $K_D$ value less than $1.7 \times 10^{-9}$ M.

As reported herein, not all substitutions at position N95 of HCDR3 that remove the Asn (N) residue are capable of improving antibody stability whilst also retaining binding affinity for the GARP-TGF-β1 complex. A germlined monoclonal antibody variant having an N95V substitution (referred to herein as 39B6-AVE) was found to be resistant to deamidation and isomerization, but underwent significant oxidation upon storage for 28 days at 37° C. The binding activity of this N95V antibody variant was also found to decrease significantly over a 56-day period of storage at 37° C. The inventors also found that bulky substitutions at adjacent position 96 in the heavy chain (i.e. the second residue of HCDR3) were incapable of improving stability and retaining high affinity antigen binding activity. As exemplified herein, the inventors tested two germlined monoclonal antibody variants including the substitutions E96K and E96R in the HCDR3 domain. The E96K variant (referred to herein as 39B6-ANK) did not undergo oxidation, but was subject to deamidation and isomerization over a 28-day period at 37° C. and underwent a significant decrease in binding activity over a 56-day period. The E96R variant (referred to herein as 39B6-ANR) underwent significant oxidation and deamidation over a 28-day period at 37° C. and underwent a decrease in binding activity over a 56-day period.

In preferred embodiments of the invention, the antibodies which specifically bind the GARP-TGF-β1 complex and exhibit improved stability comprise at least one heavy chain variable domain (VH) and at least one light chain variable domain (VL), wherein
the VH CDR3 comprises or consists of the amino acid sequence YEWETVVVGDLMYEYEY (SEQ ID NO: 13),
the VH CDR2 comprises or consists of the amino sequence RIDPEDAGTKYAQKFQG (SEQ ID NO: 12),
the VH CDR1 comprises or consists of the amino acid sequence SYYID (SEQ ID NO: 4),
the VL CDR3 comprises or consists of the amino acid sequence QQYASVPVT (SEQ ID NO: 11),
the VL CDR2 comprises or consists of the amino sequence GASRLKT (SEQ ID NO: 10), and
the VL CDR1 comprises or consists of the amino acid sequence QASQSISSYLA (SEQ ID NO: 9).

In certain preferred embodiments of the invention, the antibodies which specifically bind the GARP-TGFβ1 complex and exhibit improved stability comprise at least one heavy chain variable domain (VH) and at least one light chain variable domain (VL), wherein
the VH CDR3 comprises the amino acid sequence YEWETVVVGDLMYEYEY (SEQ ID NO: 13),
the VH CDR2 comprises the amino sequence RIDPEDAGTKYAQKFQG (SEQ ID NO: 12),
the VH CDR1 comprises the amino acid sequence SYYID (SEQ ID NO: 4),
the VL CDR3 comprises the amino acid sequence QQYASVPVT (SEQ ID NO: 11),
the VL CDR2 comprises the amino sequence GASRLKT (SEQ ID NO: 10), and
the VL CDR1 comprises the amino acid sequence QASQSISSYLA (SEQ ID NO: 9).

In certain preferred embodiments of the invention, the antibodies which specifically bind the GARP-TGF-β1 complex and exhibit improved stability comprise at least one heavy chain variable domain (VH) and at least one light chain variable domain (VL), wherein the VH CDR3 consists of the amino acid sequence YEWETVVVGDLMYEYEY (SEQ ID NO: 13),
the VH CDR2 consists of the amino sequence RIDPEDAGTKYAQKFQG (SEQ ID NO: 12),
the VH CDR1 consists of the amino acid sequence SYYID (SEQ ID NO: 4),
the VL CDR3 consists of the amino acid sequence QQYASVPVT (SEQ ID NO: 11),
the VL CDR2 consists of the amino sequence GASRLKT (SEQ ID NO: 10), and
the VL CDR1 consists of the amino acid sequence QASQSISSYLA (SEQ ID NO: 9).

These antibodies preferably exhibit a $K_D$ value less than $1.7 \times 10^{-9}$ M.

In particularly preferred embodiments of the invention, the antibodies which specifically bind the GARP-TGF-β1 complex and exhibit improved stability comprise a heavy chain variable domain (VH) comprising or consisting of the amino acid sequence of SEQ ID NO: 14 and optionally a light chain variable domain (VL) comprising or consisting of the amino acid sequence of SEQ ID NO: 15.

In particularly preferred embodiments of the invention, the antibodies which specifically bind the GARP-TGF-β1 complex and exhibit improved stability comprise a heavy chain variable domain (VH) comprising the amino acid sequence of SEQ ID NO: 14 and a light chain variable domain (VL) comprising the amino acid sequence of SEQ ID NO: 15.

In particularly preferred embodiments of the invention, the antibodies which specifically bind the GARP-TGF-β1 complex and exhibit improved stability comprise a heavy chain variable domain (VH) consisting of the amino acid sequence of SEQ ID NO: 14 and a light chain variable domain (VL) consisting of the amino acid sequence of SEQ ID NO: 15.

In further preferred embodiments of the invention, the antibodies which specifically bind the GARP-TGF-β1 complex and exhibit improved stability comprise a heavy chain comprising or consisting of the amino acid sequence of SEQ ID NO: 16 and optionally a light chain comprising or consisting of the amino acid sequence of SEQ ID NO: 17.

In further preferred embodiments of the invention, the antibodies which specifically bind the GARP-TGF-β1 complex and exhibit improved stability comprise a heavy chain comprising the amino acid sequence of SEQ ID NO: 16 and a light chain comprising the amino acid sequence of SEQ ID NO: 17.

In further preferred embodiments of the invention, the antibodies which specifically bind the GARP-TGF-β1 complex and exhibit improved stability comprise a heavy chain consisting of the amino acid sequence of SEQ ID NO: 16 and a light chain consisting of the amino acid sequence of SEQ ID NO: 17.

Polynucleotides Encoding GARP-TGF-β Antibodies

The invention also provides polynucleotide molecules comprising one or more nucleotide sequences encoding the GARP-TGF-β1 antibodies or antigen binding fragments of the invention, expression vectors containing said nucleotide sequences of the invention operably linked to regulatory sequences which permit expression of the antibodies or fragments thereof in a host cell or cell-free expression system, and host cells or cell-free expression systems containing said expression vectors.

In certain embodiments, the heavy chain variable domain and/or the light chain variable domain of the GARP-TGF-β1 antibodies or antigen-binding fragments according to the present invention are encoded by first and second polynucleotide sequences, wherein the first and second polynucleotide sequences comprise the amino acid sequences of SEQ ID NOs: 18 and 19, respectively. In certain embodiments, the polynucleotides encoding the GARP-TGF-β1 antibodies of the invention may comprise variant sequences which encode functional VH or VL domains of a GARP-TGF-β1 antibody. The variant sequences encoding VH domains may exhibit at least 80%, 85%, 90%, 95%, 97% or 99% sequence identity when optimally aligned to SEQ ID NO: 18, and the variant sequences encoding VL domains may exhibit at least 80%, 85%, 90%, 95%, 97% or 99% sequence identity when optimally aligned to SEQ ID NO: 19.

In certain embodiments, the heavy chain and/or the light chain of the GARP-TGF-β1 antibodies or antigen-binding fragments according to the present invention are encoded by first and second polynucleotide sequences, wherein the first and second polynucleotide sequences comprise the amino acid sequences of SEQ ID NOs: 20 and 21, respectively. In certain embodiments, the polynucleotides encoding the GARP-TGF-β1 antibodies of the invention may comprise variant sequences which encode heavy chains or light chains of a GARP-TGF-β1 antibody. The variant sequences encoding heavy chains may exhibit at least 80%, 85%, 90%, 95%, 97% or 99% sequence identity when optimally aligned to SEQ ID NO: 20, and the variant sequences encoding light chains may exhibit at least 80%, 85%, 90%, 95%, 97% or 99% sequence identity when optimally aligned to SEQ ID NO: 21.

In this context, % sequence identity between two polynucleotide sequences may be determined by comparing these two sequences aligned in an optimum manner and in which the polynucleotide sequence to be compared can comprise additions or deletions with respect to the reference sequence for an optimum alignment between these two sequences. The percentage of identity is calculated by determining the number of identical positions for which the nucleotide residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available at ncbi.nlm-.nih.gov/gorf/bl2, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

Polynucleotide molecules encoding the antibodies of the invention include, for example, recombinant DNA molecules. The terms "nucleic acid", "polynucleotide" or "polynucleotide molecule" as used interchangeably herein refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of an antibody according to the invention, a recombinant polynucleotide encoding it may be prepared (using standard molecular biology techniques) and inserted into a replicable vector for expression in a chosen host cell or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antibody or antigen binding fragment according to the invention has been introduced are explicitly excluded from the definition of a "host cell".

Antibody Production

In a further aspect, the invention also provides a method of producing antibodies of the invention which comprises culturing a host cell (or cell-free expression system) containing one or more polynucleotides (e.g., an expression vector) encoding the antibody under conditions which permit expression of the antibody, and recovering the expressed antibody. This recombinant expression process can be used for large scale production of antibodies, including GARP-TGF-β1 antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Pharmaceutical Compositions

The scope of the invention includes pharmaceutical compositions containing one or a combination of GARP-TGF-β1 antibodies of the invention, or antigen-binding fragments thereof, formulated with one or more pharmaceutically acceptable carriers or excipients. Such compositions may include one or a combination of (e.g., two or more different) GARP-TGF-β1 antibodies. Techniques for formulating monoclonal antibodies for human therapeutic use are well known in the art and are reviewed, for example, in Wang et al., Journal of Pharmaceutical Sciences, Vol. 96, pp 1-26, 2007, the contents of which are incorporated herein in their entirety.

In certain embodiments, the pharmaceutical compositions are formulated for administration to a subject via any suitable route of administration including but not limited to intravenous, intramuscular, intradermal, intraperitoneal, subcutaneous, epidural, nasal, oral, rectal, topical, inhalational, buccal (e.g., sublingual), and transdermal administration.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Therapeutic Utility of GARP-TGF-β1 Antibodies

The antibodies and antigen binding fragments of the present invention may be used in methods of treatment, wherein a subject in need thereof is administered a therapeutically effective amount of a GARP-TGF-β1 antibody or antigen binding fragment thereof. In certain embodiments, the antibodies and antigen binding fragments of the present invention may be used in methods of treatment, wherein a human subject in need thereof is administered a therapeutically effective amount of a GARP-TGF-β1 antibody or antigen binding fragment thereof. Provided herein are antibodies or antigen binding fragments thereof, which bind to the complex of human GARP and TGF-β1, for use as medicaments.

The antibodies and antigen binding fragments of the invention bind to the GARP-TGF-β complex on regulatory T cells and can block active TGF-β production or release. Therefore, in a further aspect of the invention, provided herein are methods for treating subjects having or suspected of having TGF-β-related disorders. Such methods involve administering to a subject in need thereof a therapeutically effective amount of a GARP-TGF-β1 antibody of the invention.

Exemplary TGF-β-related disorders include, but are not limited to, inflammatory diseases, chronic infection, cancer, fibrosis, cardiovascular diseases, cerebrovascular disease (e.g. ischemic stroke), and neurodegenerative diseases. In certain embodiments, a TGF-β-related disorder is chronic infection. In certain embodiments, a TGF-β-related disorder is cancer.

For use in administration to a subject, the antibodies and antigen binding fragments of the invention may be formulated as pharmaceutical compositions. The compositions may be administered orally, parenterally, by inhalation spray, topically, rectally, nasally, buccally, vaginally or via an implanted reservoir. The term "administration" as used herein includes without limitation subcutaneous, intravenous, intraperitoneal, intramuscular, intra-articular, intra-synovial, intrasternal, intrathecal, intrahepatic, intralesional, intratumoral, and intracranial injection or infusion techniques.

Sterile injectable forms of the compositions may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Schedules and dosages for administration of the antibody or antigen binding fragment thereof in the pharmaceutical compositions can be determined in accordance with known methods for these types of products. For example, an antibody present in a pharmaceutical composition of this invention can be supplied at a concentration of 10 mg/mL in either 100 mg (10 mL) or 500 mg (50 mL) single-use vials. The product is formulated for intravenous (IV) administration in 9.0 mg/mL sodium chloride, 7.35 mg/mL sodium citrate dihydrate, 0.7 in g/mL polysorbate 80, and Sterile Water for Injection. The pH is adjusted to 6.5.

For clinical use, the antibody or antigen binding fragment can be administered to a subject in one or more doses. For parenteral routes of administration, a single dose of the antibody or antigen binding fragment can be, for example, about 0.01 to about 100 mg/kg body weight. In an embodiment, a single dose of the antibody or antigen binding fragment can be, for example, about 0.1 to about 50 mg/kg body weight. In an embodiment, a single dose of the antibody or antigen binding fragment can be, for example, about 1 to about 20 mg/kg body weight. For repeated dosing, individual doses can be administered by the same or different routes of administration. Also for repeated dosing, individual doses can be the same or different. For example, a first or loading dose may be more than a subsequent dose. Also for repeated dosing, individual doses can be administered on a fixed schedule or on an adjustable or variable schedule based, for example, on a subject's clinical condition or clinical response. Also for repeated dosing, individual doses typically can be administered once daily, once every other day, once every 3, 4, 5, 6, or 7 days, once weekly, once biweekly, once every three or four weeks, or once every other month. Other schedules are also contemplated by the invention.

It will be appreciated that these doses and schedules are exemplary and that an optimal schedule and regimen can be determined by taking into account such factors as the particular antibody or antigen binding fragment to be administered, the disease or disorder to be treated, the size, age and condition of the subject to be treated, the route of administration, other therapies being administered to the subject, and the affinity and tolerability of the particular antibody. Such factors and dosing considerations can be determined in one or more clinical trials.

The present invention also provides methods for boosting the immune system in a subject in need thereof, comprising administering to a subject a therapeutically effective amount of an antibody or antigen binding fragment of the invention. The present invention also provides methods for inhibiting the immune suppressive function of human Tregs in a subject in need thereof, comprising administering to the subject a therapeutically effective amount of an antibody or antigen binding fragment of the invention.

The present invention also provides methods for the treatment of cancer using GARP-TGF-β1 antibodies and antigen binding fragments of the invention. Such methods may involve reducing immunosuppression in the tumor environment in a subject in need thereof.

For embodiments wherein the GARP-TGF-β1 antibodies or antigen binding fragments thereof are for use in methods of treating cancer, the antibodies or antigen binding fragments thereof may be administered in combination with one or more additional treatments for cancer, for example one or more immunotherapeutic agent(s).

For embodiments wherein the GARP-TGF-β1 antibodies are administered in combination with an immunotherapeutic agent, said immunotherapeutic agent may be a tumor vaccine. Alternatively, the immunotherapeutic agent may be an immunostimulatory antibody. Without wishing to be bound by theory, the antibodies of the invention will likely improve the efficacy of the immunotherapeutic agent by preventing or alleviating any immunosuppression. In certain embodiments, the combination with an immunotherapeutic agent may exhibit a synergistic effect.

Various cancers can be treated in accordance with the methods described herein including but not limited to adrenocortical carcinoma, anal cancer, bladder cancer, brain tumor, glioma, breast carcinoma, carcinoid tumor, cervical cancer, colon carcinoma, endometrial cancer, esophageal cancer, extrahepatic bile duct cancer, Ewing's tumor, extracranial germ cell tumor, eye cancer, gall bladder cancer, gastric cancer, germ cell tumor, gestational trophoblastic tumor, head and neck cancer, hypopharyngeal cancer, islet cell carcinoma, kidney cancer, laryngeal cancer, leukemia, lip and oral cavity cancer, liver cancer, lung cancer, lymphoma, melanoma, mesothelioma, Merkel cell carcinoma, metastatic squamous head and neck cancer, myeloma, neoplasm, nasopharyngeal cancer, neuroblastoma, oral cancer, oropharyngeal cancer, osteosarcoma, ovarian cancer, pancreatic cancer, sinus and nasal cancer, parathyroid cancer, penile cancer, pheochromocytoma, pituitary cancer, plasma cell neoplasm, prostate cancer, rhabdomyosarcoma, rectal cancer, renal cell carcinoma, salivary gland cancer, skin cancer, Kaposi's sarcoma, T-cell lymphoma, soft tissue sarcoma, stomach cancer, testicular cancer, thymoma, thyroid cancer, urethral cancer, uterine cancer, vaginal cancer, vulvar cancer, or Wilms' tumor.

Suitable tumor antigens for use as tumor vaccines known in the art include for example: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, IA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-I/Melan A, gp100, MC1R, melanocyte-stimulating hormone receptor, tyrosinase, tyrosinase related protein-1/TRPI and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le<x> (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH). Other tumor antigens include pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl80erbB-3, c-met, mn-23H I, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein/cyclophilin C-associated protein), TAAL6, TAG72, TLP, TPS, and the like. Suitable immunostimulatory antibodies include, but are not limited to: anti-CTLA-4, anti-PD1, anti-PDL1 and anti-KIR antibodies.

In certain embodiments, the methods for treating cancer described herein, comprise administering to the subject the antibody or antigen binding fragment of the invention prior to, concurrent to and/or after the administration of another anti-cancer agent or cancer treatment, such as chemotherapy treatment.

The present invention also includes methods for preventing infectious diseases by administering antibodies or antigen binding fragments of the invention so as to improve the efficacy of vaccination strategies. For example, the methods of the invention may include the prevention of infectious diseases such as HIV, malaria, or Ebola by combined administration of antibodies or antigen binding fragments as described herein together with vaccines particular to these diseases.

Kits

In a further aspect, the present invention provides a kit comprising at least one GARP-TGF-β1 antibody or antigen binding fragment of the invention.

The term "kit" is intended to mean any manufacture (e.g., a package or a container) comprising at least one reagent, e.g., an antibody or antigen binding fragment of the invention, for specifically binding the GARP-TGF-β1 complex. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

EXAMPLES

The invention will be further understood with reference to the following non-limiting examples.

Example 1: Germlining Antibody LHG-10.6

The production and characterisation of antibody "LHG-10" is described in International patent applications WO2015/015003 and WO2016/125017, the contents of which are incorporated herein in their entirety. Antibody LHG-10 was raised by immunising llamas with HEK293E cells overexpressing the human GARP-TGF-β1 complex, and was identified by selecting and screening for GARP-TGF-β1 Fabs. A light chain shuffling approach (as described for example, in International patent application WO2014/033252) was used to improve the affinity of the monoclonal antibody LHG-10, and a variant "LHG-10.6" (also referred to herein as 17H5) was identified as having improved binding characteristics. The VH and VL sequences of LHG-10 and the Vκ shuffled variant LHG-10.6 are shown in Table 3.

TABLE 3

| | | SEQ ID NO: |
|---|---|---|
| VH domain of LHG-10 and LHG10.6 | EVQLVQPGAELRNSGASVKVSCKASGYRFTSYYIDWVRQ APGQGLEWMGRIDPEDGGTKYAQKFQGRVTFTADTSTST AYVELSSLRSEDTAVYYCARNEWETVVVGDLMYEYEYWG QGTQVTVSS | 1 |
| VL domain of LHG-10 | DIQMTQSPSSLSASLGDRVTITCQASQSISSYLAWYQQK PGQAPKLLIYGASRLQTGVPSRFSGSGSGTSFTLTISGL EAEDAGTYYCQQYDSLPVTFGQGTKVELK | 2 |
| VL domain of LHG10.6 | DIQMTQSPSSLSASLGDRVTITCQASQSISSYLAWYQQK PGQAPNLIYGASRLKTGVPSRFSGSGSGTSFTLTISGL EAEDAGTYYCQQYASVPVTFGQGTKVELK | 3 |

The 17H5 antibody was found to have 88.5% identity with the closest human germline sequence (X92343|IGHV1-46*01) across the VH domain and 86.2% identity with the closest human germline sequence (X59315|IGKV1-39*01) across the VL domain. This antibody was subjected to germlining according to a 3-step method:

1—Assembly of a gene library by using overlapping oligonucleotides to synthetically generate the variable light (VL) and variable heavy (VH) chain encoding genes via PCR.
2—Cloning of this gene library into a vector (pCB13) containing the human constant heavy (CH1) and constant light kappa (CK) chain encoding genes (library construction).
3—Selection of the functional Fabs using phage display and affinity selection.

1. Library Construction

The VH of 17H5 was compared with the closest human germline sequence and framework residues deviating from the human germline were identified. These framework residues were allowed to mutate to the residue present in the human V-region, whilst also maintaining in the library the original residue. The 12 VH residues that were allowed to mutate to their human counterparts are shown in the table below. In addition to these germlining mutations, an isomerization site within CDR2 (D54;D55) and an oxidation site in CDR3 (M100f) were allowed to mutate. These sites are also shown in the table below.

TABLE 4

| Targeted residues in the 17H5 VH domain | | | | |
|---|---|---|---|---|
| Position | Camelid aa | Mutated aa | Probability | Clones |
| 1 | E | Q | 0.5 | 2 |
| 7 | P | S | 0.5 | 2 |
| 11 | L | V | 0.5 | 2 |
| 12 | R | K | 0.5 | 2 |
| 13 | N | K | 0.5 | 2 |
| 14 | S | P | 0.5 | 2 |
| 28 | R | T | 0.5 | 2 |
| 54 (HCDR2) | D | E | 0.5 | 2 |
| 55 (HCDR2) | G | A | 0.5 | 2 |

TABLE 4-continued

Targeted residues in the 17H5 VH domain

| Position | Camelid aa | Mutated aa | Probability | Clones |
|---|---|---|---|---|
| 69 | F | M | 0.5 | 2 |
| 71 | A | R | 0.5 | 2 |
| 78 | A | V | 0.5 | 2 |
| 80 | V | M | 0.5 | 2 |
| 100f (HCDR3) | M | L/T | 0.33 | 3 |
| 108 | Q | L | 0.5 | 2 |

For the Vk of 17H5, a comparison between the closest human germline sequence and the framework sequences led to the identification of 11 residues to be targeted. These sites are shown in the table below.

TABLE 5

Targeted residues in the 17H5 VL domain

| Position | Camelid aa | Mutated aa | Probability | Clones |
|---|---|---|---|---|
| 11 | L | V | 0.5 | 2 |
| 42 | Q | K | 0.5 | 2 |
| 45 | N | K | 0.5 | 2 |
| 46 | I | L | 0.5 | 2 |
| 70 | S | D | 0.5 | 2 |
| 77 | G | S | 0.5 | 2 |
| 79 | E | Q | 0.5 | 2 |
| 80 | A | P | 0.5 | 2 |
| 83 | A | F | 0.5 | 2 |
| 84 | G | A | 0.5 | 2 |
| 106 | L | I | 0.5 | 2 |

The theoretical sizes of the 17H5 germlined library are shown in Table 6.

TABLE 6

|  | 17H5 |
|---|---|
| size of the VH library | $5 \times 10^4$ |
| size of the VL library | $2 \times 10^3$ |
| size of the final library | $1 \times 10^8$ |

2. Construction of the Gene Library

The germlined libraries were created by gene assembly. Synthetic genes for VH and VL (two sets) based on this design were generated by PCR based assembly (Stemmer et al., Gene (1995) 164: 49-530). Overlapping oligonucleotides with specific mutations on certain positions were assembled by PCR. The nucleotides were degenerated to encode the human and the llama amino acid. This was done to prevent complete loss of binding in case the llama residues were critical for stability, folding or high affinity binding.

The synthetic genes of the 17H5 Vκ and VH libraries were first cloned in pCB13-CK1, a phagemid vector with the human Ck and CH1 domains, respectively. After construction of these VkCk and VHCH1 sub-libraries, the final libraries were made by ligation of the heavy chain insert into the light chain library. A colony PCR was carried out to determine the insert percentage and clones were sent for sequencing to ensure that all desired mutations were present in the library. The characteristics of the different libraries are described in the table below.

TABLE 7

Characteristics of the 17H5 germlined libraries

|  | 17H5 |
|---|---|
| size of the VH library | 1E5 |
| size of the VL library | 1E3 |
| size of the final library | 1E8 |
| % insert | 85% |

The germlining libraries were found to be of good quality and could be used for selections.

3. Selection of Fabs with High Human Identity

Phage display was used to select for Fabs with high affinity for the human GARP-TGF-β1 complex, as described previously in WO2015/015003, the contents of which are incorporated herein in their entirety. In short, a microtiter plate was coated O/N at 4° C. with the GARP-TGF-β1 complex and the day after, Fab expressing phages were incubated for 2 hours in wells coated with different concentrations of complex. Plates were washed and specific phage were eluted with trypsin and used for infection of TG1 cells. Details of the selection conditions are listed in Table 8.

TABLE 8

Details of the selection rounds for the germlined library of 17H5

| Round | Phage input (µl) | huGARP-TGF-β1 [ng/well] | Washing time | Washing antigen |
|---|---|---|---|---|
| 1 | 10 | 1000-100-10 | — | — |
| 2 | 1 | 1000-100-10 | — | — |
| 3 | 1 | 1000-100-10 | 2 hours | 20 × huGT |
| 4 | 1 | 1000-100-10 | 24 hours | 20 × huGT |
| 5 | 1 | 1000-100-10 | 72 hours | 20 × huGT |
| 6 | 1 | 1000-100-10 | 1 week | 100 × huGT |

After the first round of selection, enrichment was only observed over a coating of an irrelevant protein at 10 µg/ml. In round 2, the enrichment was 10-fold higher, while the amount of input phage was 10-fold lower. Starting from round 3, the stringency was increased by increasing the duration of the washing and by adding an excess of target in solution. A large excess of soluble target is solution was added to prevent rebinding of the dissociated phage. Even after the 6th round, with a 1-week off-rate washing and a 100-fold excess of soluble target, enrichment was still observed.

4. Screening of Fabs with High Human Identity

Masterplates were picked from selection round 2, 3, 4, 5 and 6 (48 clones for each round). Periplasmic extracts were prepared and off-rates were determined by SPR. All clones were DNA-sequenced and amino acid sequences were deduced thereof. Clones with an identity to human germline Ig V-region above 92% are summarized in Table 9. The off-rates of these clones were measured as periplasmic extracts on SPR, and compared to the off-rate of Fab 17H5.

TABLE 9

Binding affinity of clones with more than 92% total human identity

| Fab | Off-rate ($10^{-4}$ $s^{-1}$) | % Identity VH | % Identity VK | % Overall Identity | Isomerisation site D54; G55 (HCDR2) | Risk oxidation M100f (HCDR3) |
|---|---|---|---|---|---|---|
| 17H5 | 2.01 | 88.5 | 86.2 | 87.4 | wt (D54; G55) | wt (M100f) |
| *39A12 | 6.06 | 95.4 | 96.2 | 95.8 | E54; G55 | T100f |
| *39A5 | 1.9 | 94.2 | 96.2 | 95.2 | wt | wt |
| 39H6 | 4.4 | 93.1 | 96.2 | 94.7 | wt | wt |
| 40H3 | 2.47 | 94.2 | 95.0 | 94.6 | wt | wt |
| 39A10 | 1.77 | 94.2 | 95.0 | 94.6 | wt | wt |
| *39B6 | 1.05 | 95.4 | 93.7 | 94.6 | wt | wt |
| 39E6 | 8.61 | 96.5 | 92.5 | 94.5 | wt | wt |
| 40G4 | 2.07 | 93.1 | 95.0 | 94.1 | wt | wt |
| 38C3 | 2.32 | 95.4 | 92.5 | 94.0 | wt | wt |
| 39G3 | 6.62 | 95.4 | 92.5 | 94.0 | E54; G55 | T100f |
| 39G9 | 9.47 | 95.4 | 92.5 | 94.0 | E54; G55 | T100f |
| 38F3 | 2.03 | 91.9 | 95.0 | 93.5 | D54; A55 | wt |
| *38F2 | 4.08 | 94.2 | 92.5 | 93.4 | D54; A55 | T100f |
| *39B10 | 2.36 | 95.4 | 91.2 | 93.3 | E54; G55 | wt |
| 39C6 | 7.89 | 95.4 | 91.2 | 93.3 | E54; G55 | T100f |
| 39G6 | 7.79 | 94.2 | 91.2 | 92.7 | wt | L100f |
| 38C5 | 1.69 | 90.8 | 93.7 | 92.3 | E54; G55 | wt |
| 38B2 | 2.86 | 93.1 | 91.2 | 92.2 | wt | T100f |

*5 Fabs that were reformatted as full IgG1

The 5 clones showing an overall human identity of >93% and an off-rate comparable to that of the parental 17H5 Fab were recloned as full human IgG1 antibodies. The CDR, VH and VL sequences of these antibodies are shown in Tables 10, 11 and 12.

TABLE 10

VH CDR sequences for GARP-TGF-β1 Abs

| | CDR1 | SEQ ID NO: | CDR2 | SEQ ID NO: | CDR3 | SEQ ID NO: |
|---|---|---|---|---|---|---|
| 39B6 | SYYID | 4 | RIDPEDGGTKYAQKFQG | 5 | NEWETVVVGDLMYEYEY | 6 |
| 39A12 | SYYID | 4 | RIDPEEGGTKYAQKFQG | 7 | NEWETVVVGDLTYEYEY | 32 |
| 39A5 | SYYID | 4 | RIDPEDGGTKYAQKFQG | 5 | NEWETVVVGDLMYEYEY | 6 |
| 38F2 | SYYID | 4 | RIDPEDAGTKYACKFQG | 8 | NEWETVVVGDLTYEYEY | 32 |
| 39B10 | SYYID | 4 | RIDPEEGGTKYAQKFQG | 5 | NEWETVVVGDLMYEYEY | 6 |

TABLE 11

VL CDR sequences for GARP-TGF-β1 Abs

| | CDR1 | SEQ ID NO: | CDR2 | SEQ ID NO: | CDR3 | SEQ ID NO: |
|---|---|---|---|---|---|---|
| 39B6 | QASQSISSYLA | 9 | GASRLKT | 10 | QQYASVPVT | 11 |
| 39A12 | QASQSISSYLA | 9 | GASRLKT | 10 | QQYASVPVT | 11 |
| 39A5 | QASQSISSYLA | 9 | GASRLKT | 10 | QQYASVPVT | 11 |
| 38F2 | QASQSISSYLA | 9 | GASRLKT | 10 | QQYASVPVT | 11 |
| 39B10 | QASQSISSYLA | 9 | GASRLKT | 10 | QQYASVPVT | 11 |

TABLE 12

Variable domain sequences for GARP-TGF-β1 Abs

| Clone | VH | SEQ ID NO: | VL | SEQ ID NO: |
|---|---|---|---|---|
| 39B6 | QVQLVQPGAEVRKPGASVKVSCKASGYRFTSYYIDWVRQAPGQGLEWMGRIDPEDGGTKYAQKFQGRVTMTADTSTSTVYVELSSLRSEDTAVYYCARNEWETVVVGDLMYEYEYWGQGTLVTVSS | 22 | DIQMTQSPSSLSASVGDRVTITCQASQSISSYLAWYQQKPGQAPKILIYGASRLKTGVPSRFSGSGSGTSFTLTISSLEPEDAATYYCQQYASVPVTFGQGTKVEIK | 23 |
| 39A12 | EVQLVQPGAEVKKPGASVKVSCKASGYRFTSYYIDWVRQAPGQGLEWMGRIDPEEGGTKYAQKFQGRVTFTADTSTSTVYVELSSLRSEDTAVYYCARNEWETVVVGDLTYEYEYWGQGTLVTVSS | 24 | DIQMTQSPSSLSASVGDRVTITCQASQSISSYLAWYQQKPGQAPKILIYGASRLKTGVPSRFSGSGSGTDFTLTISSLQAEDFATYYCQQYASVPVTFGQGTKVEIK | 25 |
| 39A5 | QVQLVQPGAELRNPGASVKVSCKASGYRFTSYYIDWVRQAPGQGLEWMGRIDPEDGGTKYAQKFQGRVTFTRDTSTSTVYMELSSLRSEDTAVYYCARNEWETVVVGDLMYEYEYWGQGTLVTVSS | 26 | DIQMTQSPSSLSASLGDRVTITCQASQSISSYLAWYQQKPGQAPKLLIYGASRLKTGVPSRFSGSGSGTDFTLTISSLQPEDAATYYCQQYASVPVTFGQGTKVEIK | 27 |
| 38F2 | QVQLVQPGAELKKPGASVKVSCKASGYRFTSYYIDWVRQAPGQGLEWMGRIDPEDAGTKYAQKFQGRVTFTADTSTSTVYVELSSLRSEDTAVYYCARNEWETVVVGDLTYEYEYWGQGTLVTVSS | 28 | DIQMTQSPSSLSASVGDRVTITCQASQSISSYLAWYQQKPGKAPNLLIYGASRLKTEVPSRFSGSGSGTDFTLISGLEPEDAGTYYCQQYASVPVTFGQGTKVEIK | 29 |
| 39B10 | EVQLVQSGAELKKPGASVKVSCKASGYRFTSYYIDWVRQAPGQGLEWMGRIDPEEGGTKYAQKFQGRVTMTADTSTSTAYMELSSLRSEDTAVYYCARNEWE | 30 | DIQMTQSPSSLSASLGDRVTITCQASQSISSYLAWYQQKPGQAPNILIYGASRLKTGVPSRFSGSGSGTDFTLTISGLEAEDFAT | 31 |

TABLE 12-continued

Variable domain sequences for GARP-TGF-β1 Abs

| Clone | VH | SEQ ID NO: | VL | SEQ ID NO: |
|---|---|---|---|---|
| | LRSEDTAVYYCARNEWE TVVVGDLMYEYEYWGQG TLVTVSS | | YYCQQYASVPVTFGQGT KVEIK | |

5. In Vitro Characterisation of mAbs with High Human Framework Residue Identity The five germlined clones reformatted to human IgG1 were produced by transient transfection in HEK 293E cells. All the antibodies were tested for binding to the human GARP-TGF-β1 complex by SPR and showed binding affinity similar to the non-germlined parental clone (KD 2-5 times lower than 17H5). Changing residue M100f in the CDR3 to a threonine decreased the $K_D \approx$ 5-fold. Binding properties and characteristics of the germlined 17H5 Abs are listed in Table 13.

TABLE 13

Binding properties and characteristics of the germlined 17H5 Abs

| mAb | Kd(M) | fold difference | isomerisation site D54; G55 | risk oxidation M100f | % Identity VH | % Identity VK | % Identity overall |
|---|---|---|---|---|---|---|---|
| 17H5 | 1.00E−10 | 1.0 | wt (DG) | wt (M) | 88.5 | 86.2 | 87.3 |
| 39B6 | 1.67E−10 | 1.7 | wt (DG) | wt (M) | 95.4 | 93.7 | 94.5 |
| 39B10 | 2.62E−10 | 2.6 | EG | wt (M) | 95.4 | 91.2 | 93.3 |
| 39A5 | 2.98E−10 | 3.0 | wt (DG) | wt (M) | 94.2 | 96.2 | 95.2 |
| 38F2 | 4.80E−10 | 4.8 | DA | T | 94.2 | 92.5 | 93.3 |
| 39A12_T | 5.05E−10 | 5.1 | EG | T | 95.4 | 96.2 | 95.8 |

6. Stability of Germlined mAb 3966

Clone 39B6 was selected as the lead germlined clone based on its binding characteristics. This antibody was produced in two effector function deficient formats, hIgG1$^{N297Q}$ and hIgG4$^{S228P}$, and stability tests were carried out. Prior to the stability testing, the affinity of the effector deficient 39B6 antibodies for GARP-TGF-β1 was tested by BiacoreT200 using a CM5 chip coated with GARP-TGF-β1 complex at 750 RU (Table 14) or coated with the antibodies at 1000 RU (Table 15).

TABLE 14

| mAb | Format | $K_D$ (M) | Fold-difference |
|---|---|---|---|
| LHG10.6 | IgG1-N297Q | 8.19E−10 | 1 |
| 39B6 | IgG1-N297Q | 8.63E−11 | 0.1 |
| 39B6 | IgG1-N297Q | 3.13E−10 | 0.4 |

TABLE 15

| mAb | Format | $K_D$ (M) | Fold-difference |
|---|---|---|---|
| LHG10.6 | IgG1-N297Q | 5.34E−10 | 1 |
| 39B6 | IgG1-N297Q | 1.23E−09 | 2.3 |
| 39B6 | IgG1-N297Q | 1.02E−09 | 1.9 |

The thermo-tolerance of the 3966 antibodies was tested using the following set-up.

mAb sample preparation: 1 ml of the mAbs (39B6-IgG1 and 39B6-IgG4), fresh prepared stock solution (5 mg/ml), were put in 2 ml glass screw cap glass vials and stored at 5° C. and 37° C. Vials were checked immediately for absence of particles.

PBS negative control: aliquots of 1 ml filtered Dulbecco's PBS were prepared in 2 ml glass vials as the PBST negative control. Vials were checked immediately for absence of particles.

PBSTw negative control: aliquots of 1 ml filtered Dulbecco's PBS containing 0.02% Tween80 (Sigma) were prepared in 2 ml glass vials as the PBSTw negative control. Vials were checked immediately for absence of particles.

High-aggregation control: 1 ml aliquots of an in-house antibody were prepared with abundant visible aggregation in 2 ml glass vials.

Reference sample: for each antibody, 60 µl mAb aliquots were prepared in 500 µl sterile, PCR tubes, labeled and stored at −20° C.

Figure 2:
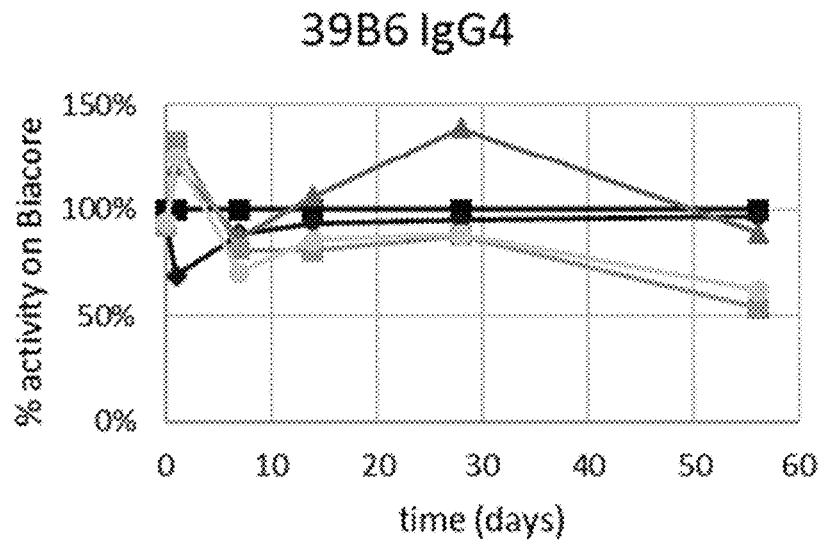
FIG. 2 shows target binding activity as measured by surface plasmon resonance (SPR) for antibodies 39B6 IgG1$^{N297Q}$ and 39Bb 6 IgG4$^{S228P}$ over a 56-day period for samples stored at −20° C., 5° C. and 37° C. in PBS or PBSTween (PBSTw). The reference sample (−20° C.) was set as 100% binding activity at each time point.
Figure 2:
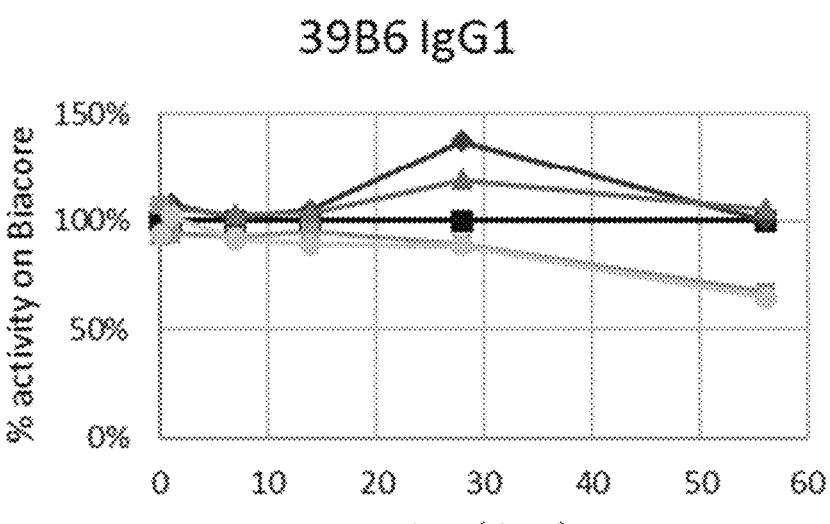

The stability of the antibodies stored at different temperatures and under different conditions (PBS versus PBSTw) was monitored over a 56-day time course. The effect of storage on target binding activity as measured by SPR (Biacore™) is shown in FIG. 2. As can be seen from the results presented, the 3966 antibody (in both effector deficient formats) exhibited a trend towards lower target binding activity in both PBS and PBS/Tween when stored at 37° C. In contrast, the samples stored at 5° C. did not display a significant loss in target binding activity over the time-course.

Example 2: Development of GARP-TGF-β1 Antibodies with Improved Stability

2.1 Production of 39B6 Variants

The decrease in target binding activity noted above for antibody 39B6 was found to be linked to deamidation occurring at positions 95-96 of VH CDR3. As such, further work was carried out to improve the stability of 39B6.

First, this clone was subjected to modification of the VH chain in the CDR2 region to introduce a G55A substitution (39B6-A). The VH and VL regions of 39B6-A were recloned into the human IgG4s$^{228P}$ backbone i.e. the effector function deficient human antibody format.

In an attempt to improve the stability of antibody 39B6-A IgG4s$^{228P}$, five variants were generated having mutations at positions 95 or 96 of CDR3 of the VH domain. These variants are shown below. All variants were produced in the effector function deficient format IgG4$^{S228P}$.

TABLE 16

39B6-A Variants

| Variant | Position 95 | Position 96 |
|---|---|---|
| 39B6-AVE | V | E* |
| 39B6-AYE | Y | E* |
| 39B6-ANK | N* | K |
| 39B6-ANR | N* | R |
| 39B6-AEE | E | E* |

*residue already present in 39B6-A

The antibodies were filtered and concentrated to 5 mg/ml and stored in Dulbecco's PBS with 0.02% Tween80 (Sigma). The Tween80 was needed to stabilize the antibody formulations.

The affinity of all antibodies (including 39B6-A) for GARP-TGF-$\beta$1 was tested by BiacoreT200 using a CM5 chip coated with GARP-TGF-$\beta$1 complex at 150 RU (Table 17) or coated with the antibodies at 200 RU (Table 17)

TABLE 17

| mAb | $K_D$ (M) | Fold-difference |
|---|---|---|
| 39B6-A | 9.91E−10 | 1.0 |
| 39B6-AVE | 8.94E−10 | 0.9 |
| 39B6-AYE | 7.63E−10 | 0.8 |
| 39B6-AEE | 5.79E−09 | 5.8 |
| 39B6-ANK | 8.80E−10 | 0.9 |
| 39B6-ANR | 8.84E−10 | 0.9 |
| LHG10.6 | 5.17E−10 | 0.5 |

TABLE 18

| mAb | $K_D$ (M) | Fold-difference |
|---|---|---|
| 39B6-A | 1.33E−09 | 1.0 |
| 39B6-AVE | 1.29E−09 | 1.0 |
| 39B6-AYE | 1.62E−09 | 1.2 |
| 39B6-AEE | 1.02E−07 | 76.7 |
| 39B6-ANK | 2.02E−09 | 1.5 |
| 39B6-ANR | 1.94E−09 | 1.5 |

Figure 3A:
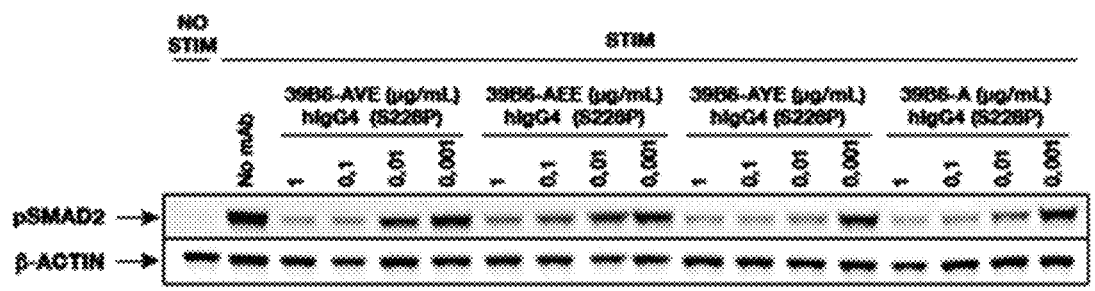
FIGS. 3A and 3B show the results of testing the 39B6-A antibody variants in an assay designed to monitor SMAD2 phosphorylation downstream of TGF-β receptor activation. SMAD2 phosphorylation serves as a marker of activation of the TGF-β signalling pathway, following TGF-β binding to its receptor. If SMAD2 phosphorylation is reduced, TGF-β activity is inhibited.
Figure 3A:
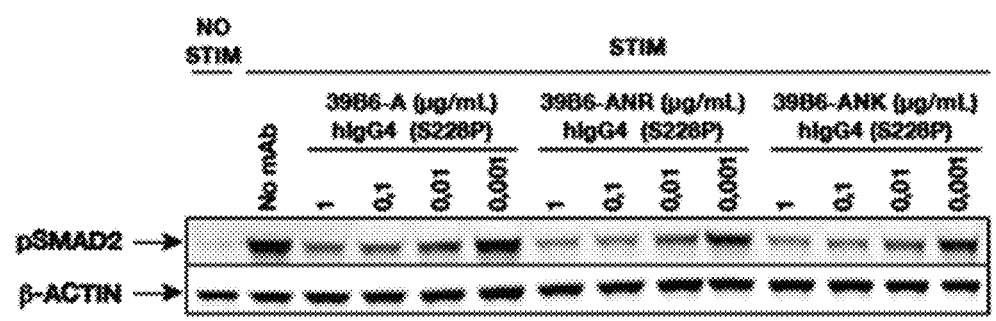
Figure 3B:
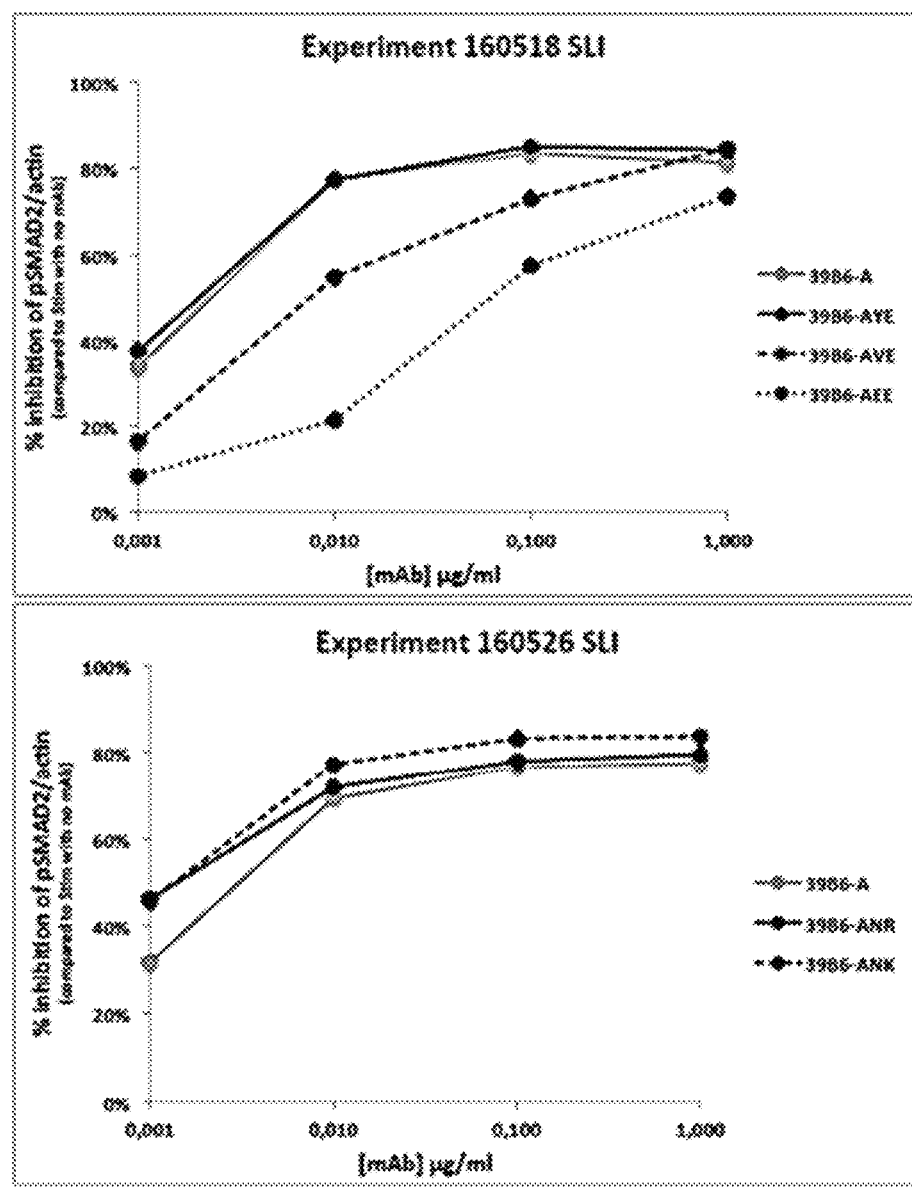

The potency to block the release of active TGF-$\beta$ by human Tregs was analyzed with all variants by determining the level of SMAD2 phosphorylation of CD3/CD28 stimulated human Tregs in the presence of the mAbs. As shown in FIG. 3, antibodies 39B6-AYE, 39B6-ANK and 39B6-ANR had a similar potency in the SMAD2 phosphorylation assay compared to the original 39B6-A. The variants 39B6-AEE and 39B6-AVE showed a clear loss in potency.

Figure 4:
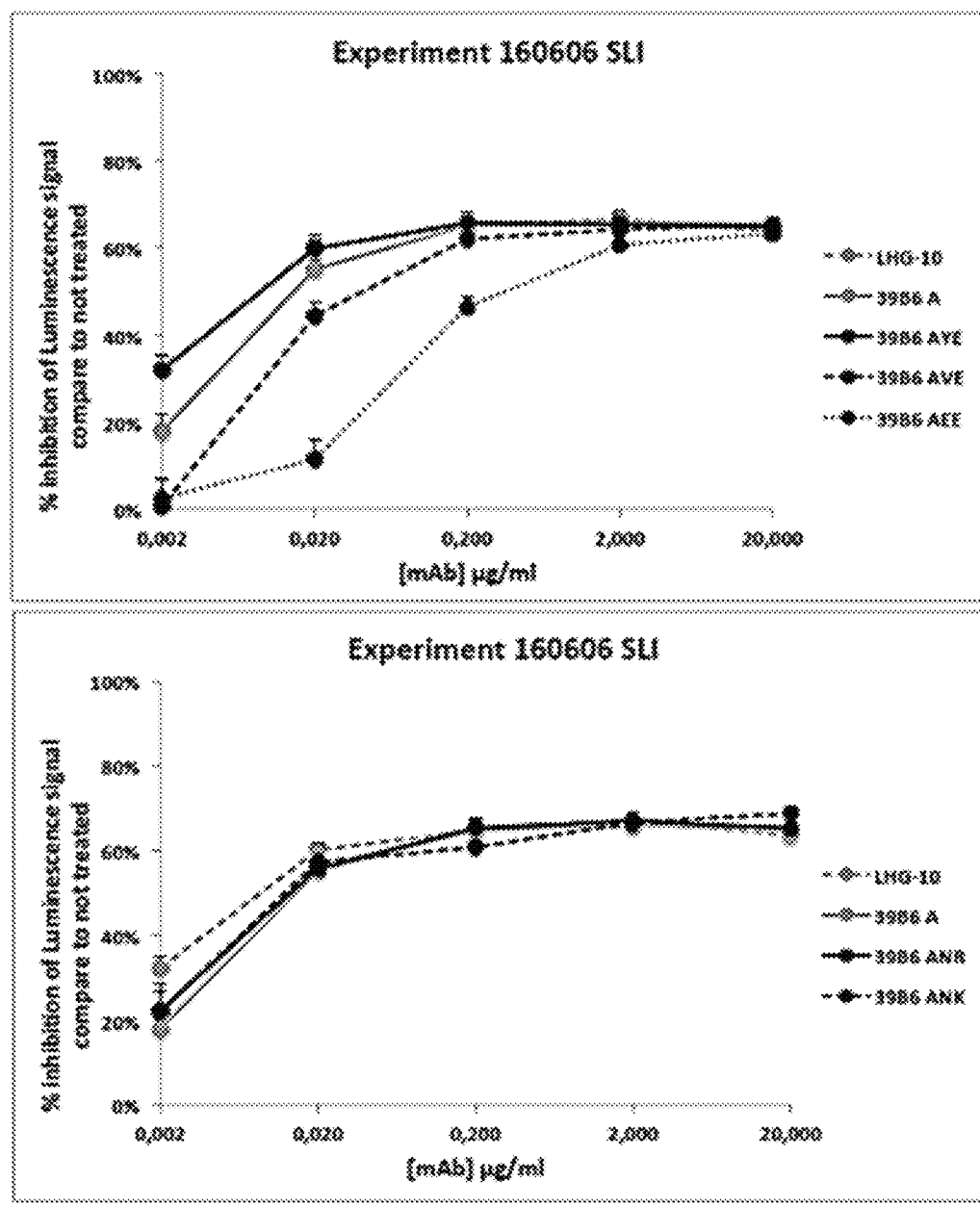
FIG. 4 shows the results of testing the 39B6-A antibody variants in an assay designed to measure TGF-β activity via a luciferase reporter gene conjugated to a SMAD promoter. Graphs show percentage inhibition of luminescence signal in the presence of different concentrations of the GARP-TGF-β antibodies LHG-10, 3966-A, 39B6-AVE, 39B6-AEE, 39B6-AYE, 39B6-ANR and 39B6-ANK.

Similar results were obtained using the GAGA-luc assay where 293T-hGARP cells were transiently transfected with a reporter plasmid in which Firefly luciferase is under the control of a SMAD responding promotor (GAGA-luc). Antibodies 39B6-AYE, 39B6-ANK and 39B6-ANR had a similar potency in the luciferase assay compared to the original 39B6-A. The variants 39B6-AEE and 39B6-AVE showed a clear loss in potency (see FIG. 4).

2.2 Stability Studies

With the exception of 39B6-AEE, the variants were tested for stability using different approaches as described below.

For each of the different stability studies, the antibodies were tested using one or more of the following techniques:
Visual inspection
Size Exclusion-HPLC
SDS-PAGE (reducing and non-reducing)
Target binding affinity on SPR
Protein concentration
The protocols for these techniques are described below.
Protocol for Visual Inspection Samples were blinded and scored for the presence of visible particles by visual inspection of the vials by three analysts. Samples were allowed to reach room temperature for 30 minutes before inspection. The following scoring system was used for the assessment:
A: sample is clear, no particles visible
B: very few particles
C: moderate presence of particles
D: abundant particles observed
f: fibers
Protocol for Size-Exclusion Chromatography (SE-HPLC)
System, Column and Sample Preparation The column used throughout the study was an Xbridge Protein BEH SEC 200A (3.5 µm, 7.8*30 mm, Waters) which is routinely stored in 20% EtOH. An Xbridge Protein BEH 200A pre-guard column was coupled to the analytical column (3.5 µm, 7.8*3 mm; Waters). Before each utilization, the column was equilibrated with Dulbecco's PBS for 5CV at least, and before being removed from the system, it was cleaned with 5CV of LC-grade water. All solvents were filtered and degassed before utilization.

The chromatographic system used was an Agilent 1260 Infinity, equipped with a quaternary pump, automatic injector, on-line degasser and a DAD detector. The column was not kept in a thermostated compartment and samples were analyzed at room temperature. The detector was set to wavelengths 280 and 214 nm simultaneously (reference wavelength at 360 nm with a cut-off of 100 nm). Aggregation monitoring was followed on channel 214 nm. Data acquisition was done with the Chemstation software (Agilent).

Sample analysis was done by transferring 25 µl of all original samples directly from the 5 mg/ml concentration under aseptic conditions. They were spun down at 2000 rcf for 1 min and 20 µl was carefully transferred into screw-cap, amber, glass vials. The injection volume for each condition was 5 µl (25 µg), at a flow rate of 0.7 ml PBS/min for 25 min. Each injection was accompanied with a needle wash with LC-grade water and seal washing took place at the end of each sample.

Every time point sequence was initiated with 2×PBS injections (blank; 5 µl injection volume), followed by 2 µl BEH 200 Standard Protein mixture injection (Waters) and a known-aggregation mAb sample. Every twelve samples analyzed, a blank injection was done. Each analytical sequence was terminated as initiated but in the reverse order (known-aggregation control mAb, BEH standard protein mixture and 2× blank).
Method Used for Determination of % Aggregation and % Monomer Area The following protocol was used:
Integrate all chromatograms with the method ARGX-115 (basic technical parameters: tangent skim standard mode, slope sensitivity 2.0, height reject 1.7, area reject 1.0, peak width: 0.02)
Verify that all peaks are integrated in a way that coincides with the previous analyses obtained
Export the integration results in a PDF and Excel file
Calculate the % total aggregation as the summary of areas of all peaks eluting before the monomer peak divided by the total area of the injection and multiply by 100
Also calculate the % monomer area by dividing the monomer area by the total area and multiply by 100.

This % monomer area reflects if there are insoluble aggregates present in the sample Keep detailed records to monitor the performance, efficiency and resolution of the analytical column (i.e. peak symmetry, monomer area, total area, reproducibility of retention times etc.)

Protocol for SDS-PAGE

Sample Preparation

Sample analysis was done by transferring 25 µl of all original samples at 5 mg/ml in 100 µl PBS/0.02% Tween80 (abbreviated as PBSTw throughout this study) under aseptic conditions in order to generate an intermediate concentration at 1 mg/ml, for SDS-PAGE (reducing and non-reducing), binding affinity on SPR and protein concentration assessment. 4-20% tris glycine, mini-protean, stain-free, pre-cast gels were used for SDS-PAGE analysis of the samples (Biorad). A batch of 4×-concentrated loading dye, with or without reducing agent DTT, was prepared and aliquoted to −20° C. Routinely, 5 µl was taken from the intermediate dilution at 1 mg/ml and then, 5 µl of 4× concentrated loading dye (+/− DDT) was added together with 10 µl of mQ. The final quantity for each condition was 5 µg. Samples were boiled for 10 min at 95° C. and then loaded (20 µl) in the pre-cast gels. Electrophoresis took place for 35 min in a tris-glycine buffer system under a constant voltage of 200 V. Blue staining (Gentaur) followed for 1 h. All gels were de-stained with mQ water for at least 1 h.

Determination of % Full Length Ab

The intensity of the different bands was determined on the Odyssey v3.0 Li-Cor system by scanning the protein gels to one-channel detection (700 nm) under the settings: focus offset 0.5 mm and "high" quality. The brightness and contrast for each analysis were set to 50% with a linear manual parameter of 5.

The method was as follows:

Scan the gel and verify that all bands on gel are surrounded by tight rectangles Choose "export" in the settings in order to obtain the raw intensity of all bands in an Excel format Calculate the % raw intensity of each band present in a lane as the raw intensity of the band divided by the total raw intensity of the lane and multiply by 100

For the non-reducing conditions, the % full length Ab is defined as the % raw intensity of the band which corresponds to the ~100 kD band For the reducing conditions, the % full length Ab is defined as the summary of the raw intensity of the bands which correspond to the ~25-35 kD and ~55 kD bands Protocol for Target Binding Activity Measurement in Biacore 3000

Sample Preparation From the intermediate concentration of all samples at 1 mg/ml described above, an extra 1/250 dilution was done for SPR analysis to yield a final concentration of 4 µg/ml. This 1/250 dilution took place for all conditions in two steps: a) 5 µl (1 mg/ml)+120 µl HBS-EP (SPR buffer) and b) an extra 10× dilution (15 µl+135 µl HBS-EP). For each antibody and each time point, a separate standard curve was prepared, starting from a −80° C. frozen sample. This was analyzed together with the stability samples to determine the slope of each curve after general fitting of the standards. These slopes were used to calculate the percent activity of the stability samples by setting the reference sample at 100%.

Determination of % Activity on Biacore

To determine the target binding activity in Biacore, a CM5 chip was coated with ~4000 RU human GARP-TGF-β complex. Flow was set to 30 µl/min with a "kinject" injection mode and two regeneration injections (1 mM NaCl, 2.5 mM glycine pH 1.5) with a 5 min interval.

The method was carried out as follows:

Open the curves in the BIAEVAL program and select value '2-1' (1: blank, 2 hGARP-TGF-β1)

Select one curve at the time for plot overlay

Delete the regeneration part of the curve

Select the baseline just before the injection and transform the Y-axis for 'zero at median of selection'

Select 'General Fit', starting from 120 sec after injecting and ending at 155 sec Plot the standards in Excel and determine the slope of the curve for each antibody These values are converted to a percent activity by setting the reference (sample stored at −20° C.) at 100%

Protocol for Protein Concentration

For the determination of the protein content of each condition, the NanoDrop system was used by measuring the absorbance at 280 nm of each sample (2 µl). The system was blanked with PBS and the protein determination was done by measuring in triplicates the absorbance at 280 nm of each sample (intermediate dilution at 1 mg/ml). All values obtained at 280 nm were divided by the factor 1.51. A PBS blank measurement was done after each different condition. All data were reported as average value of the three measurements for each condition.

2.1 Temperature Stability Study

To monitor the stability of the antibodies under different temperature storage conditions, the following set-up was followed:

mAb sample preparation: 1 ml of the mAbs (39B6-AVE, 39B6-AYE, 39B6-ANK and 39B6-ANR), fresh prepared stock solution (5 mg/ml), were put in 2 ml glass screw cap glass vials and stored at 5° C. and 37° C. Vials were checked immediately for absence of particles.

PBSTw negative control: aliquots of 1 ml filtered Dulbecco's PBS containing 0.02% Tween80 (Sigma) were prepared in 2 ml glass vials as the PBSTw negative control. Vials were checked immediately for absence of particles.

High-aggregation control: 1 ml aliquots of an in-house antibody were prepared with abundant visible aggregation in 2 ml glass vials.

Reference sample: for each antibody, 60 µl mAb aliquots were prepared in 500 µl sterile, PCR tubes, labeled and stored at −20° C.

At different time points, samples of the mAbs were taken from the storage conditions and tested for:

Visual inspection

SE-HPLC

SDS-PAGE (reducing and non-reducing)

target binding affinity on SPR protein concentration

Visual Inspection

The results for visual inspection are shown in Table 19 below. All mAbs were in PBSTw, which should give a stabilizing effect.

TABLE 19

Results of visual inspection of mAb samples of 39B6-AVE, 39B6-AYE, 39B6-ANK and 39B6-ANR over a 56-day period under storage conditions of 5° C. and 37° C.

| Sample | 0 d | 1 d | 7 d | 14 d | 28 d | 56 d |
|---|---|---|---|---|---|---|
| Storing conditions: 5° C. | | | | | | |
| 39B6-AVE | A-B-B | A-B-B | Af-B-B | Af-B-B | Af-B-A | B-Bf-Af |
| 39B6-AYE | A-A-A | A-A-A | A-A-B | Af-A-B | Af-Af-B | Af-Bf-A |
| 39B6-ANK | A-A-A | A-A-B | Af-B-B | Af-A-B | B-A-C | B-A-B |
| 39B6-ANR | B-A-A | B-B-B | B-Bf-Bf | C-Bf-Bf | C-Bf-Cf | C-Bf-C |
| High aggregation control | C-C-C | C-C-C | C-D-D | D-D-D | D-D-D | D-D-D |
| PBSTw | Af-A-A | Af-A-A | A-B-B | Af-A-B | Af-A-A | Af-A-A |
| Storing conditions: 37° C. | | | | | | |
| 39B6-AVE | A-A-A | A-B-B | Af-Bf-B | Af-Bf-B | Af-Bf-B | Af-Bf-Af |
| 39B6-AYE | A-A-A | A-B-B | Af-A-B | Af-B-B | B-B-B | B-Af-Bf |
| 39B6-ANK | A-A-A | A-A-B | A-B-B | B-A-B | C-B-B | D-Bf-Bf |
| 39B6-ANR | B-A-A | B-A-B | Af-Af-Bf | Af-Af-Bf | B-Af-Bf | C-Af-Bf |
| High aggregation control | C-C-C | C-C-C | C-D-C | D-D-C | D-D-D | D-D-D |
| PBSTw | Af-B-B | Af-Bf-B | Af-Af-Bf | Af-Bf-B | Af-Bf-Bf | Af-A-Af |

For the 5° C. condition, the average scores for the mAbs after 56 days were as follows:
39B6-AYE: 'sample is clear, no particles visible'
39B6-AVE and 39B6-ANK: 'very few particles'
39B6-ANR: 'moderate presence of particles'.

The PBSTw buffer is scored 'sample is clear, no particles visible' at 5° C. so this indicates that the observed particles are protein-related.

For the 37° C. storage condition, the average scores for the mAbs after 56 days were as follows:
39B6-AYE, 39B6-ANK and 39B6-ANR: 'very few particles'
39B6-AVE: 'sample is clear, no particles visible'.

The PBSTw buffer is scored 'sample is clear, no particles visible' at 37° C. so this indicates that the observed particles are protein-related.

Analysis by SE-HPLC

Protein aggregation and fragmentation were measured by SE-HPLC.

Figure 5:
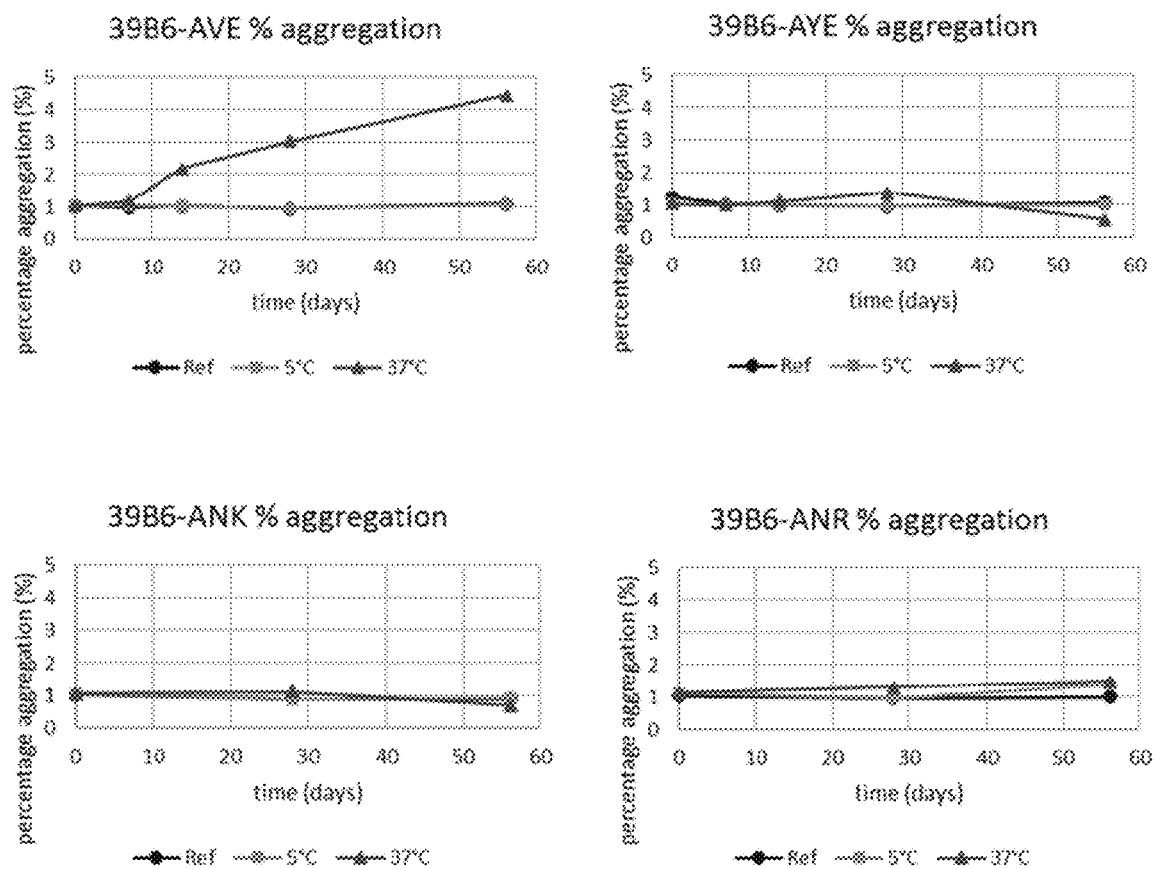
FIG. 5 shows the percentage aggregate formation over a 56-day period with antibodies 39B6-AVE, 39B6-AYE, 39B6-ANK and 39B6-ANR stored at 5° C. and 37° C. Aggregate formation was monitored by size exclusion chromatography (SE-HPLC).

The protein aggregation results for the mAbs 39B6-AVE, 39B6-AYE, 39B6-ANK and 39B6-ANR, as measured by SE-HPLC, are summarized in Table 20 below and shown in FIG. 5.

TABLE 20

% Aggregate formation monitored by SE-HPLC for mAbs 39B6-AVE, 39B6-AYE, 39B6-ANK and 39B6-ANR

| t (days) | Ref | 5° C. | 37° C. |
|---|---|---|---|
| 39B6-AVE - Percent aggregation (%) upon SE-HPLC analysis | | | |
| 0 | 1.0 | 1.0 | 1.0 |
| 7 | 1.0 | 1.1 | 1.2 |
| 14 | 1.0 | 1.0 | 2.2 |
| 28 | 0.9 | 0.9 | 3.0 |
| 56 | 1.1 | 1.1 | 4.4 |
| 39B6-AYE - Percent aggregation (%) upon SE-HPLC analysis | | | |
| 0 | 1.2 | 1.0 | 1.0 |
| 7 | 1.0 | 1.0 | 1.0 |
| 14 | 1.0 | 1.0 | 1.1 |
| 28 | 0.9 | 0.9 | 1.4 |
| 56 | 1.1 | 1.0 | 0.5 |
| 39B6-ANK - Percent aggregation (%) upon SE-HPLC analysis | | | |
| 0 | 1.0 | 1.0 | 1.0 |
| 28 | 0.9 | 0.9 | 1.1 |
| 56 | 0.9 | 0.9 | 0.7 |

TABLE 20-continued

% Aggregate formation monitored by SE-HPLC for mAbs 39B6-AVE, 39B6-AYE, 39B6-ANK and 39B6-ANR

| t (days) | Ref | 5° C. | 37° C. |
|---|---|---|---|
| 39B6-ANR - Percent aggregation (%) upon SE-HPLC analysis | | | |
| 0 | 1.0 | 1.1 | 1.1 |
| 28 | 1.0 | 1.0 | 1.3 |
| 56 | 1.0 | 1.4 | 1.5 |

When stored at 5° C., no change in % aggregate levels was observed for mAbs 39B6-AYE, 39B6-AVE and 39B6-ANK over the 56 d time period. Observed % aggregate levels were low—between 0.9% and 1.1%. A minor increase in aggregate levels was observed for mAb 39B6-ANR from 1.1% to 1.4%.

At 37° C., no change in % aggregate levels was observed for mAbs 39B6-AYE and 39B6-ANK. For 39B6-ANR a minor increase from 1.1% at 0 d to 1.5% at 56 d was observed. For 39B6-AVE an increase in % aggregate was observed from 1.0% at 0 d to 4.4% at 56 d.

Figure 6:
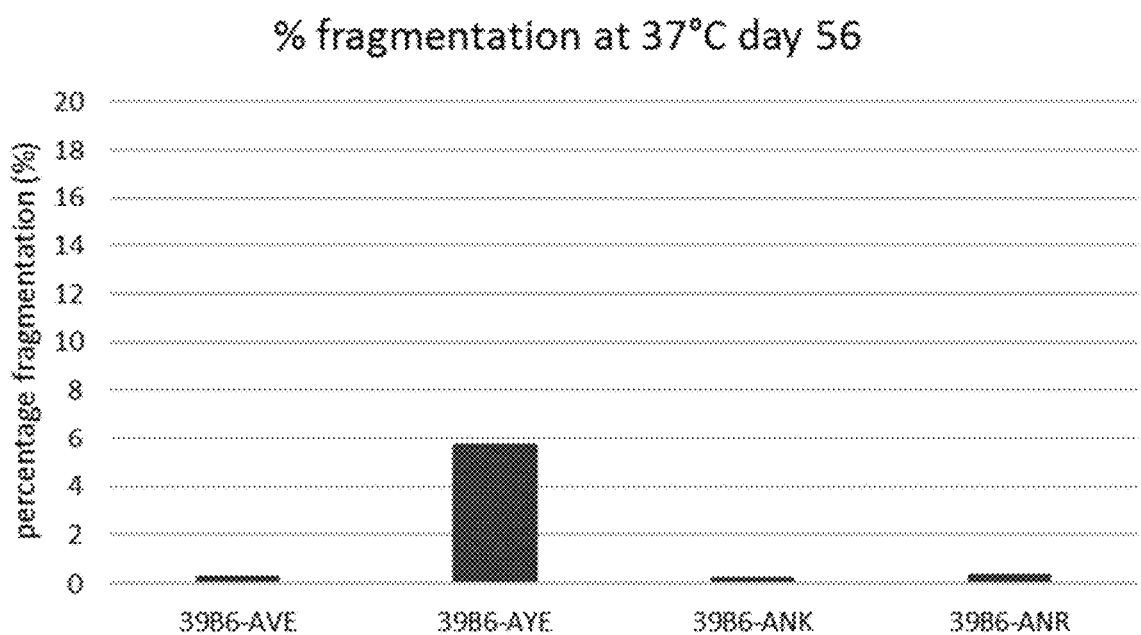
FIG. 6 shows the percentage fragment formation over a 56-day period with antibodies 39B6-AVE, 39B6-AYE, 39B6-ANK and 39B6-ANR stored at 37° C. Fragment formation was monitored by size exclusion chromatography (SE-HPLC).
Figure 7:
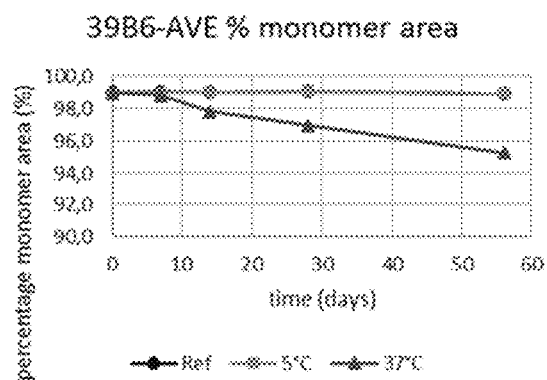
FIG. 7 shows the percentage monomer area over a 56-day period with antibodies 39B6-AVE, 39B6-AYE, 39B6-ANK and 39B6-ANR stored at 5° C. and 37° C. Monomer area was monitored by size exclusion chromatography (SE-HPLC).
Figure 7:
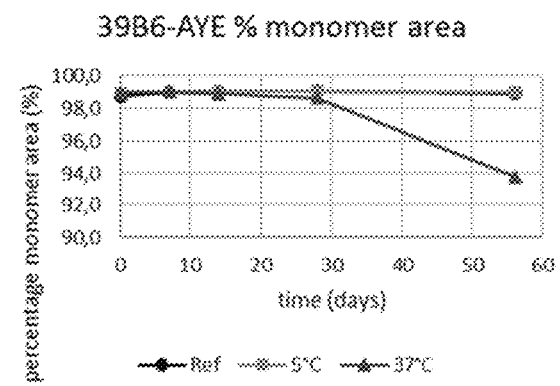
Figure 7:
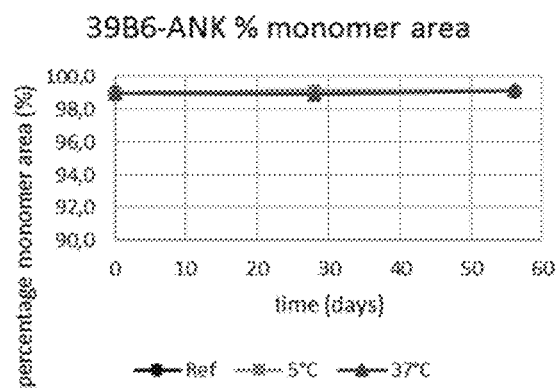
Figure 7:
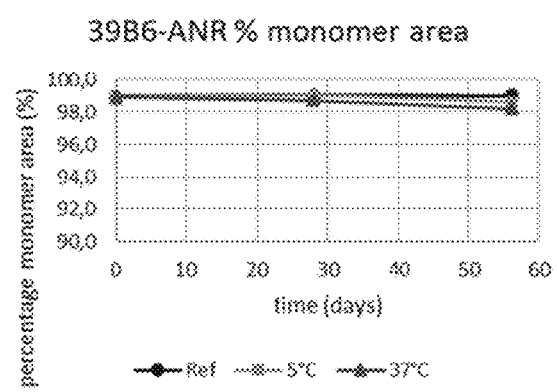
Figure 8A:
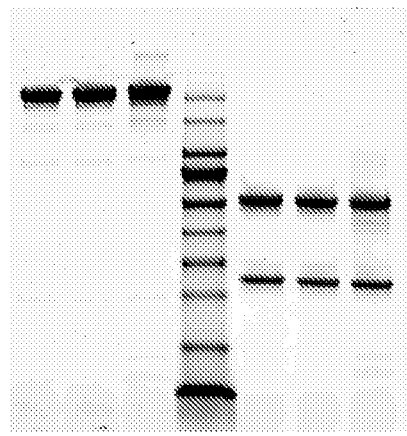
FIGS. 8A-8D show the results of SDS-PAGE analysis of antibody samples stored for 56 days at a reference temperature (−20° C.), at 5° C. and at 37° C.
Figure 8B:
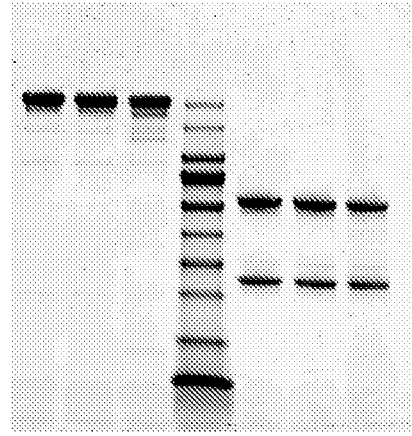
Figure 8C:
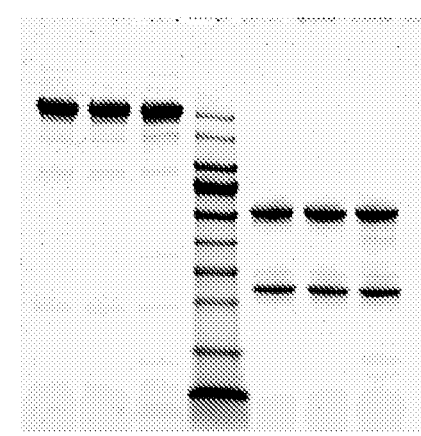
Figure 8D:
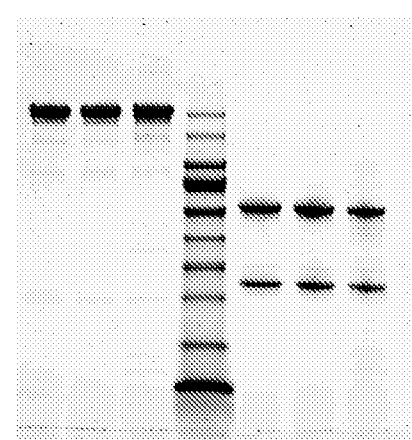

The presence of fragment peaks for the mAbs 39B6-AVE, 39B6-AYE, 39B6-ANK and 39B6-ANR, as measured by SE-HPLC, is shown in Table 21 and FIG. 6. As fragmentation peaks were only observed at 37° C. after 56 days, only these results are presented.

TABLE 21

% Fragment formation monitored by size-exclusion chromatography for mAbs 39B6-AVE, 39B6-AYE, 39B6-ANK and 39B6-ANR at 56 days

| t (days) | Ref | 5° C. | 37° C. |
|---|---|---|---|
| 39B6-AVE - Percent fragmentation (%) upon SE-HPLC analysis | | | |
| 56 | 0 | 0 | 0.3 |
| 39B6-AYE - Percent fragmentation (%) upon SE-HPLC analysis | | | |
| 56 | 0 | 0 | 5.7 |

TABLE 21-continued

% Fragment formation monitored by size-exclusion chromatography for mAbs 39B6-AVE, 39B6-AYE, 39B6-ANK and 39B6-ANR at 56 days

| t (days) | Ref | 5° C. | 37° C. |
|---|---|---|---|
| 39B6-ANK - Percent fragmentation (%) upon SE-HPLC analysis | | | |
| 56 | 0 | 0 | 0.2 |
| 39B6-ANR - Percent fragmentation (%) upon SE-HPLC analysis | | | |
| 56 | 0 | 0 | 0.3 |

For mAbs 39B6-AVE, 39B6-ANK and 39B6-ANR the percentage of fragment peaks is between 0.2% and 0.3% after 56 days whilst for mAb 39B6-AYE the percentage of fragment peaks is 5.7%.

The results of the % monomer peak for all mAbs are summarized in Table 22.

TABLE 22

Monomer area (%) monitored by size-exclusion chromatography for mAbs 39B6-AVE, 39B6-AYE, 39B6-ANK and 39B6-ANR

| t (days) | Ref | 5° C. | 37° C. |
|---|---|---|---|
| 39B6-AVE - Percent monomer area (%) upon SE-HPLC analysis | | | |
| 0 | 99.0 | 99.0 | 99.0 |
| 7 | 99.0 | 98.9 | 98.8 |
| 14 | 99.0 | 99.0 | 97.8 |
| 28 | 99.1 | 99.1 | 97.0 |
| 56 | 98.9 | 98.9 | 95.3 |
| 39B6-AYE - Percent monomer area (%) upon SE-HPLC analysis | | | |
| 0 | 98.8 | 99.0 | 99.0 |
| 7 | 99.0 | 99.0 | 99.0 |
| 14 | 99.0 | 99.0 | 98.9 |
| 28 | 99.1 | 99.1 | 98.6 |
| 56 | 98.9 | 99.0 | 93.8 |
| 39B6-ANK - Percent monomer area (%) upon SE-HPLC analysis | | | |
| 0 | 99.0 | 99.0 | 99.0 |
| 28 | 99.1 | 99.0 | 98.9 |
| 56 | 99.1 | 99.1 | 99.1 |
| 39B6-ANR - Percent monomer area (%) upon SE-HPLC analysis | | | |
| 0 | 99.0 | 98.9 | 98.9 |
| 28 | 99.0 | 99.0 | 98.7 |
| 56 | 99.0 | 98.6 | 98.2 |

SDS-PAGE

The SDS-PAGE results for analysis of all antibodies are shown in Table 23 and FIG. 8.

TABLE 23

Total percentage of full length Ab/heavy chain estimated by SDS-PAGE analysis and Odyssey scanning for mAbs 39B6-AVE, 39B6-AYE, 39B6-ANK and 39B6-ANR

| | Non-reducing conditions | | | Reducing conditions | | |
|---|---|---|---|---|---|---|
| t (days) | Ref | 5° C. | 37° C. | Ref | 5° C. | 37° C. |
| % full-length 39B6-AVE | | | | | | |
| 0 | 77.2 | | 74.4 | 96.7 | | 96.6 |
| 7 | 76.0 | 78.0 | 79.8 | 97.9 | 98.0 | 97.8 |
| 14 | 80.3 | 81.9 | 79.8 | 98.4 | 97.5 | 97.1 |
| 28 | 82.8 | 81.9 | 74.5 | 96.2 | 96.1 | 85.6 |
| 56 | 79.2 | 80.7 | 70.7 | 95.1 | 94.8 | 78.6 |
| % full-length 39B6-AYE | | | | | | |
| 0 | 74.2 | | 74.6 | 96.4 | | 97.2 |
| 7 | 76.5 | 79.6 | 77.8 | 98.4 | 97.8 | 98.0 |
| 14 | 77.1 | 77.9 | 76.9 | 97.1 | 96.5 | 90.8 |
| 28 | 75.6 | 77.3 | 73.6 | 97.0 | 98.3 | 90.3 |
| 56 | 73.4 | 73.4 | 59.8 | 96.4 | 94.7 | 88.0 |
| % full-length 39B6-ANK | | | | | | |
| 0 | 74.7 | | 71.3 | 96.7 | | 96.6 |
| 28 | 70.8 | 70.7 | 74.2 | 97.0 | 96.9 | 89.5 |
| 56 | 79.3 | 78.5 | 73.6 | 96.8 | 96.7 | 88.1 |
| % full-length 39B6-ANR | | | | | | |
| 0 | 76.2 | | 76.5 | 97.1 | | 96.9 |
| 28 | 78.1 | 78.7 | 73.5 | 96.9 | 96.1 | 84.9 |
| 56 | 74.1 | 75.7 | 70.6 | 95.5 | 95.6 | 79.0 |

No trend towards degradation was observed for any of the mAbs for the 5° C. temperature condition for both the reducing and non-reducing conditions.

At 37° C., all mAbs showed a similar rate of degradation for the non-reducing condition except for mAb 39B6-AYE. This mAb shows a similar degradation rate up to 28 days but demonstrates a faster degradation rate between day 28 and day 56 compared to the other mAbs. For the reducing condition, all mAbs show a similar rate of degradation.

Target Binding Affinity on Biacore

Figure 9:
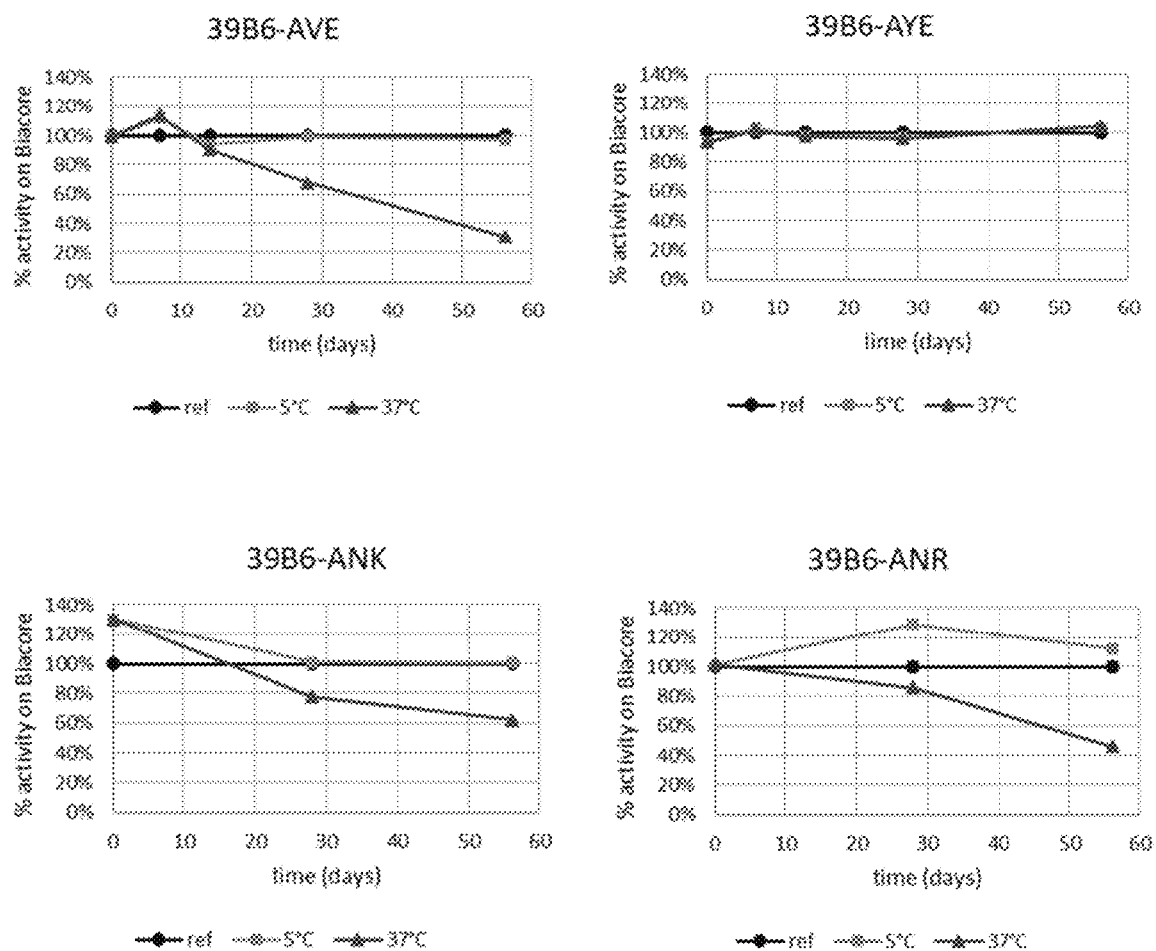
FIG. 9 shows target binding activity as measured by SPR for antibodies 39B6-AVE, 39B6-AYE, 39B6-ANK and 39B6-ANR over a 56-day period for samples stored at −20° C., 5° C. and 37° C. The reference sample (−20° C.) was set as 100% binding activity at each time point.

Samples were tested for their target binding activity in Biacore by measuring the slope at each time point. The reference sample was set as 100% of the activity. The results for all mAbs are summarized in Table 24 and FIG. 9.

TABLE 24

Percentage activity on Biacore for mAbs 39B6-AVE, 39B6-AYE, 39B6-ANK and 39B6-ANR

| t (days) | Ref | 5° C. | 37° C. |
|---|---|---|---|
| 39B6-AVE - Activity on Biacore (%) | | | |
| 0 | 100.0% | 99.5% | 99.5% |
| 7 | 100.0% | 111.7% | 113.9% |
| 14 | 100.0% | 93.8% | 90.2% |
| 28 | 100.0% | 99.0% | 68.0% |
| 56 | 100.0% | 96.9% | 31.3% |
| 39B6-AYE - Activity on Biacore (%) | | | |
| 0 | 100.0% | 93.5% | 93.5% |
| 7 | 100.0% | 103.1% | 101.5% |
| 14 | 100.0% | 97.5% | 97.5% |
| 28 | 100.0% | 96.7% | 96.1% |
| 56 | 100.0% | 103.5% | 104.2% |
| 39B6-ANK - Activity on Biacore (%) | | | |
| 0 | 100.0% | 130.1% | 130.1% |
| 28 | 100.0% | 101.1% | 77.8% |
| 56 | 100.0% | 100.6% | 62.4% |
| 39B6-ANR - Activity on Biacore (%) | | | |
| 0 | 100.0% | 100.9% | 100.9% |
| 28 | 100.0% | 129.1% | 85.4% |
| 56 | 100.0% | 85.4% | 46.3% |

For the mAb samples stored at 37° C., only antibody 39B6-AYE retained target binding activity over the full 56-day period. All of the other antibodies displayed a significant decrease in target binding activity over the 56-day period when stored at 37° C.

Protein Concentration

Figure 10:
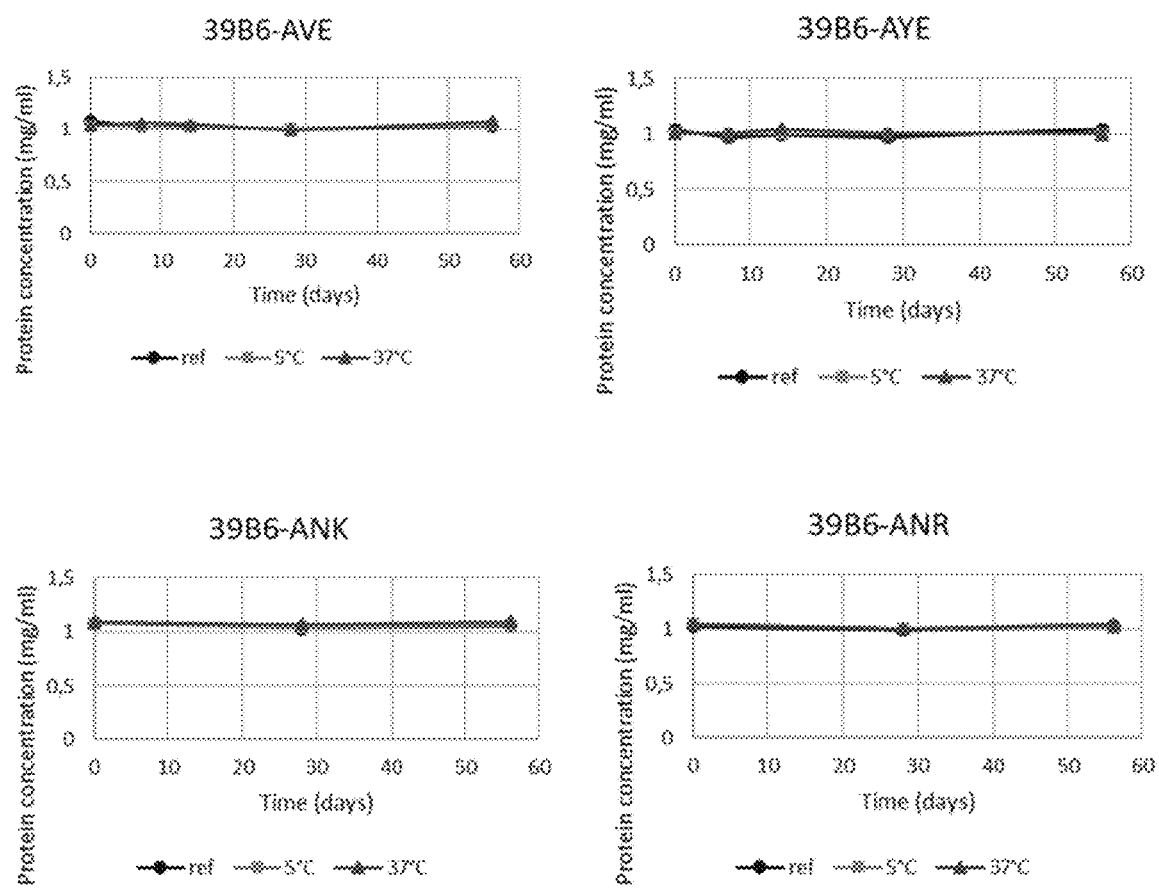
FIG. 10 shows the protein concentration (mg/ml) for samples of antibodies 39B6-AVE, 39B6-AYE, 39B6-ANK and 39B6-ANR over a 56-day period for samples stored at −20° C. (ref), 5° C. and 37° C.

The protein concentration of all samples was measured for each condition on NanoDrop. In Table 25 and FIG. 10, the measured protein concentration for all mAbs is shown.

TABLE 25

Protein concentration (mg/ml) for mAbs 39B6-AVE, 39B6-AYE, 39B6-ANK and 39B6-ANR

| t (days) | Ref | 5° C. | 37° C. |
|---|---|---|---|
| 39B6-AVE - Protein concentration (mg/ml) | | | |
| 0 | 1.1 | 1.0 | 1.0 |
| 7 | 1.0 | 1.0 | 1.1 |
| 14 | 1.0 | 1.0 | 1.1 |
| 28 | 1.0 | 1.0 | 1.0 |
| 56 | 1.0 | 1.0 | 1.1 |
| 39B6-AYE - Protein concentration (mg/ml) | | | |
| 0 | 1.0 | 1.0 | 1.0 |
| 7 | 1.0 | 1.0 | 1.0 |
| 14 | 1.0 | 1.0 | 1.0 |
| 28 | 1.0 | 1.0 | 1.0 |
| 56 | 1.0 | 1.0 | 1.0 |

TABLE 25-continued

Protein concentration (mg/ml) for mAbs 39B6-AVE, 39B6-AYE, 39B6-ANK and 39B6-ANR

| t (days) | Ref | 5° C. | 37° C. |
|---|---|---|---|
| 39B6-ANK - Protein concentration (mg/ml) | | | |
| 0 | 1.1 | 1.1 | 1.1 |
| 28 | 1.0 | 1.0 | 1.1 |
| 56 | 1.1 | 1.1 | 1.1 |
| 39B6-ANR - Protein concentration (mg/ml) | | | |
| 0 | 1.0 | 1.0 | 1.0 |
| 28 | 1.0 | 1.0 | 1.0 |
| 56 | 1.0 | 1.0 | 1.0 |

Summary and Conclusion for the Temperature Stability Study

The temperature stability study revealed some significant differences between the four mAbs tested: an aggregation of 4.4% was observed on SE-HPLC for mAb 39B6-AVE after 56 days at 37° C. and a fragmentation of 5.7% for mAb 39B6-AYE. However, this fragmentation for mAb 39B6-AYE did not affect the target binding activity at 37° C. on Biacore; after 56 days this was still as good as the reference sample. Meanwhile, lower target binding activity for mAbs 39B6-AVE, 39B6-ANK and 39B6-ANR was clearly seen at 37° C. after 56 days.

2.2.2 Freeze-Thaw Stability Study

To monitor the stability of the antibodies under freeze-thaw conditions, the set-up was as follows. A 1 ml aliquot of the mAbs (at 5 mg/ml) was frozen for at least 6 hours at −20° C. and thawed for 1 hour at RT. This cycle was repeated 9× (10 freeze-thaw cycles in total). Samples were analyzed by visual inspection, SE-HPLC, SDS-PAGE, target binding activity on Biacore and protein concentration. Reference samples stored at −20° C. were used for all analyses in parallel. As the mAbs 39B6-ANR and 39B6-ANK have a possible deamidation site, they were only subjected to analysis by visual inspection.

Visual Inspection

The results for visual inspection in the freeze-thaw stability study are shown in Table 26. All mAbs were in PBSTw, which should give a stabilizing effect.

TABLE 26

Visual Inspection freeze-thaw stability for mAbs 39B6-AVE, 39B6-AYE, 39B6-ANK and 39B6-ANR

| Sample | 10x FT |
|---|---|
| 39B6-AVE | B-B-B |
| 39B6-AYE | B-Af-B |
| 39B6-ANK | A-Bf-Bf |
| 39B6-ANR | A-A-B |
| High aggregation control | C-D-D |
| PBSTw | B-Af-Bf |

The average scores for the mAbs were as follows: 39B6-AVE, 39B6-AYE and 39B-ANK: 'very few particles'; and
39B6-ANR: 'sample is clear, no particles visible'.

The PBSTw buffer was scored by two people as 'very few particles' and therefore, the particles seen in the 39B6-AVE, 39B6-AYE and 39B-ANK samples may not be protein-related. It can be concluded that all mAbs remain unchanged after 10 freeze-thaw cycles.

Analysis by SE-HPLC

Protein aggregation and fragmentation were measured by SE-HPLC.

The protein aggregation results for the freeze-thaw stability study for the mAbs 39B6-AVE and 39B6-AYE are summarized in Table 27.

TABLE 27

% Aggregate formation monitored by size-exclusion chromatography in freeze-thaw stability for mAbs 39B6-AVE and 39B6-AYE

| 39B6-AVE | | 39B6-AYE | |
|---|---|---|---|
| Ref | 10x FT | Ref | 10x FT |
| 1.0 | 1.0 | 1.0 | 0.9 |

No change in percentage aggregate levels was observed for either mAb following 10 freeze-thaw cycles as compared to the reference samples.

The areas of the monomeric peak for all different injections were also examined. The % monomer area results for the mAbs 39B6-AVE and 39B6-AYE are summarized in Table 28.

TABLE 28

% Monomer area monitored by size-exclusion chromatography in freeze-thaw stability for mAbs 39B6-AVE and 39B6-AYE.

| 39B6-AVE | | 39B6-AYE | |
|---|---|---|---|
| Ref | 10x FT | Ref | 10x FT |
| 99.0 | 99.0 | 99.0 | 99.1 |

No change in % monomer area was observed for both mAbs following 10 freeze-thaw cycles compared to the reference samples.

Figure 11:
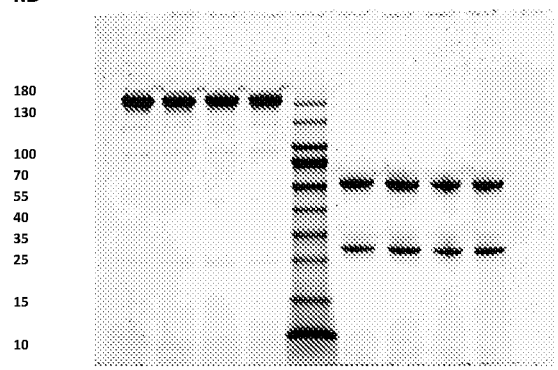
FIG. 11 shows the results of SDS-PAGE analysis of antibody samples after 10 freeze-thaw cycles. Markers appear at the centre of the gel. To the left of the markers, the 4 samples are the samples analysed under non-reducing conditions: (i) Ref for 39B6-AVE; (ii) Freeze-thaw sample for 39B6-AVE; (iii) Ref for 39B6-AYE; and (iv) Freeze-thaw sample for 39B6-AYE. To the right of the markers, the 4 samples are the samples analysed under reducing conditions: (i) Ref for 39B6-AVE; (ii) Freeze-thaw sample for 39B6-AVE; (iii) Ref for 39B6-AYE; and (iv) Freeze-thaw sample for 39B6-AYE.

Analysis by SDS-PAGE Freeze-thaw samples were analyzed for their integrity by SDS-PAGE under non-reducing and reducing conditions. The results are shown in Table 29 and FIG. 11 for mAbs 39B6-AVE and 39B6-AYE.

TABLE 29

Total percentage of full length Ab/heavy chain estimated by SDS-PAGE analysis and Odyssey scanning in freeze-thaw stability study for mAbs 39B6-AVE and 39B6-AYE

| Non-reducing conditions | | Reducing conditions | |
|---|---|---|---|
| Ref | 10x FT | Ref | 10x FT |
| % full-length 39B6-AVE | | | |
| 78.1 | 79.3 | 95.9 | 96.1 |
| % full-length 39B6-AYE | | | |
| 78.8 | 78.7 | 96.3 | 97.0 |

No changes were observed for both mAbs after 10 freeze-thaw cycles.

Analysis of Target Binding by Biacore

Figure 12:
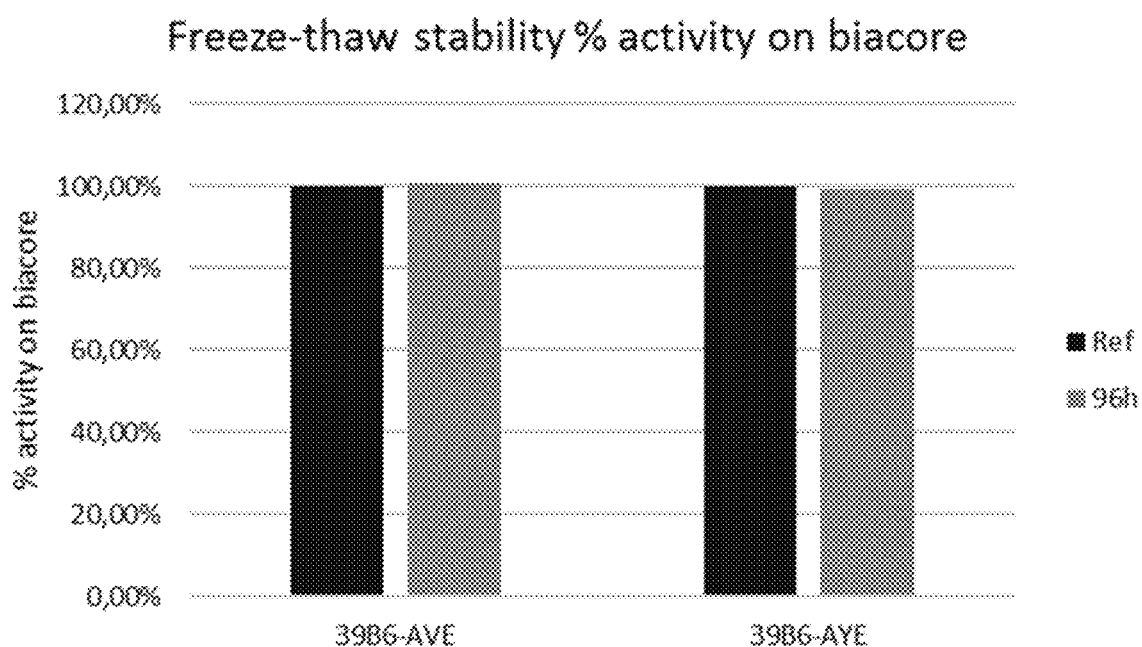
FIG. 12 shows target binding activity as measured by SPR following 10 freeze-thaw cycles for antibodies 39B6-AVE and 39B6-AYE. The reference sample (−20° C.) was set as 100% binding activity at each time point.

Samples were tested for their target binding activity in Biacore by measuring the slope after 10 freeze-thaw cycles. The reference sample was set as 100% of the activity. The results for both mAbs 39B6-AVE and 39B6-AYE are shown in FIG. 12.

The results demonstrate that after 10 freeze-thaw cycles no change in target binding activity is observed.

Analysis of Protein Concentration

Figure 13:
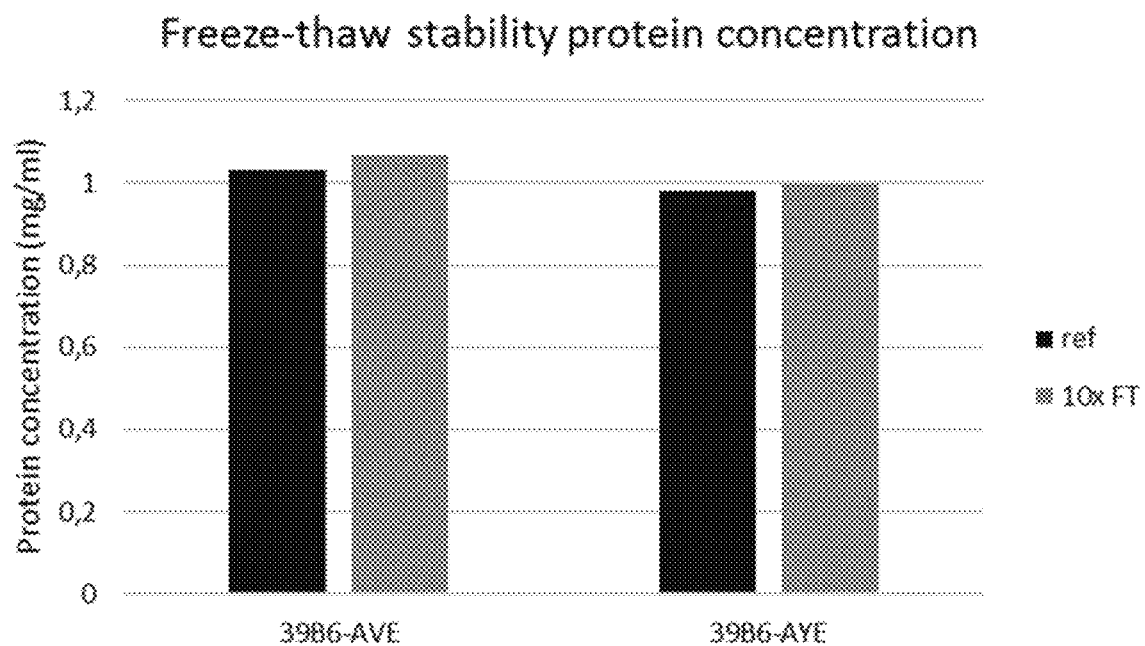
FIG. 13 shows the protein concentration (mg/ml) for samples of antibodies 39B6-AVE and 39B6-AYE following 10 freeze-thaw cycles.

The protein concentration of the freeze-thaw samples was measured on NanoDrop. In Table 30, the measured protein concentration for mAbs 39B6-AVE and 39B6-AYE after 10 freeze-thaw cycles is shown. Also, FIG. 13 shows these results for both mAbs.

TABLE 30

Protein concentration (mg/ml) in freeze-thaw stability for mAbs 39B6-AVE and 39B6-AYE

| 39B6-AVE | | 39B6-AYE | |
|---|---|---|---|
| Ref | 10x FT | Ref | 10x FT |
| 1.0 | 1.1 | 1.0 | 1.0 |

Conclusion

The freeze-thaw stability study did not reveal any significant differences for the tested mAbs 39B6-AVE and 39B6-AYE.

2.2.3 Thermal stability study

To analyse the melting curves, mAbs were heated according to the scheme below. Following completion of the thermal cycle in the PCR device, samples were tested for affinity on Biacore.

The protocol used was as follows:
1) Aliquots of 1 ml for each mAb were stored in glass vials at −20° C. in the beginning of the study
2) After one week of storage, they were defrosted once
3) The mAbs were diluted at 1 mg/ml as usual and then further diluted at 100 μg/ml (10× dilution: 200 μl+1800 μl PBSTw)
4) The diluted mAbs were aliquoted in a PCR plate (50 μl/well)
5) Keep sufficient sample and also sample at 5° C. as reference to be analyzed in parallel
6) 1 h in PCR device exposed at the temperatures given below
7) 2 h in PCR device at 25° C.
8) At 4° C. in PCR device
9) Prepare the samples and the references for analysis at 4 μg/ml (25× dilution: 168 μl Biacore buffer+7 μl sample)

Run the program as shown in FIG. 21 in a gradient PCR device.

Figure 14:
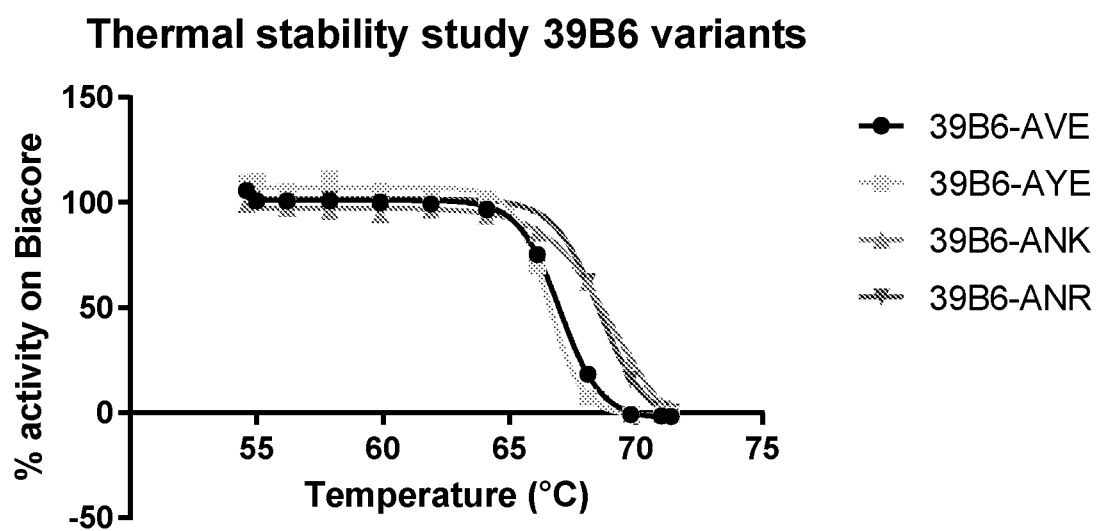
FIG. 14 shows target binding activity as measured by SPR following thermal stability testing at temperatures ranging from 54.6° C. through 71.4° C. for antibodies 39B6-AVE, 39B6-AYE, 39B6-ANK and 39B6-ANR. The reference sample was set as 100% binding activity.

Protocol for Biacore analysis:
The same CM5 chip, coated with ~4000 RU human GARP-TGF-β complex was used
Open the curves in the BIAEvaluation program and select value '2-1' (1: blank, 2 hGARP-TGF-β)
Select one curve at the time for plot overlay
Delete the regeneration part of the curve
Select the baseline just before the injection and transform the Y-axis for 'zero at median of selection'
Select 'General Fit', starting from 120 sec after injecting and ending at 155 sec
For calculation of the IC50: The slope for 5° C. references is leveled at 100%. The percentage (Y-axis) of the other temperatures (X-axis) can be calculated Thermo-tolerance of the four mAbs was measured and the results are summarized in FIG. 14. The melting temperature was calculated as the temperature at which 50% of the antibody is still functional. The reference samples which were kept at 5° C. were set as 100% of the activity. The melting temperatures are shown in Table 31.

TABLE 31

Melting temperatures in thermal stability study

| mAb | Melting temperature |
|---|---|
| 39B6-AVE | 67.0° C. |
| 39B6-AYE | 66.5° C. |
| 39B6-ANK | 69.1° C. |
| 39B6-ANR | 68.6° C. |

The mAbs 39B6-ANK and 39B6-ANR displayed the highest melting temperatures: 69.13° C. and 68.55° C., respectively. The mAbs 39B6-AVE and 39B6-AYE also gave good melting temperatures, 66.99° C. and 66.53° C., respectively. All melting temperatures for all mAbs can be considered high.

Conclusion of the Thermal Stability Study

The four mAbs demonstrated good thermo-tolerance. The melting temperatures were comparable to the original 39B6-A mAb in the previous stability study, 66.8° C.

2.2.4 Rotational Stability Study

For the rotational stability study, the set-up was as follows. Aliquots of 1 ml for each mAb were stored in glass vials at −20° C. at the beginning of the study. After one week of storage the aliquots were defrosted once and rotated head over head at 15 rpm at room temperature.

Samples were scored for presence of particles at the indicated time points:

Hours: 0, 3, 6, 24, 30, 48, 54, 72 and 96

Samples were also analyzed after 96 hours by SE-HPLC, SDS-PAGE, target binding activity on Biacore and protein concentration. Reference samples stored at −20° C. were used for all analyses in parallel. As the mAbs 39B6-ANR and 39B6-ANK still have a possible deamidation site, they were only assessed by visual inspection.

Visual Inspection

The results for visual inspection in the rotational stability study are shown in Table 32. All mAbs are in PBSTw, which should give a stabilizing effect.

TABLE 32

Visual Inspection rotational stability study for mAbs 39B6-AVE, 39B6-AYE, 39B6-ANK and 39B6-ANR

| Sample | 0 h | 3 h | 6 h | 24 h | 30 h | 48 h | 54 h | 72 h | 96 h |
|---|---|---|---|---|---|---|---|---|---|
| 39B6-AVE | Af-B-Bf | Af-B-Bf | Af-B-Bf | Af-Cf-Cf | Af-Bf-Cf | Af-B-Bf | B-B-Bf | B-B-Bf | B-B-Bf |
| 39B6-AYE | Af-Bf-Bf | Af-Bf-Bf | Af-Bf-Bf | Af-Bf-Bf | Af-Bf-Bf | Af-Bf-Bf | Af-Bf-Bf | B-Bf-Bf | B-Bf-Bf |
| 39B6-ANK | Af-Bf-C | Af-Bf-Bf | Af-Bf-Bf | Af-Bf-Bf | Af-Bf-Bf | Af-Bf-Bf | B-Bf-Cf | B-Bf-Cf | B-Bf-Cf |
| 39B6-ANR | Af-Bf-Bf | Af-Bf-Bf | Af-Bf-Bf | Af-Bf-Bf | Af-Bf-Bf | Af-Bf-Bf | Af-Bf-Bf | Af-Bf-Bf | Af-Bf-Bf |
| High aggregation control | C-B-C | C-Df-D | C-Df-D | C-Df-Df | C-Df-Df | C-Df-Df | C-Df-Df | D-Df-Df | D-Df-Df |
| PBSTw | A-A-A | A-A-A | A-A-A | A-A-A | A-A-A | A-A-A | A-A-A | A-A-A | A-A-A |

All mAbs were found to have an average score of 'very few particles' so they remain relatively unaffected after 96 hours of rotation. The PBSTw buffer did not contain any particles in any experimental condition tested. This indicates that the observed 'very few particles' are protein-related in the antibody samples.

Analysis by SE-HPLC

Protein aggregation and fragmentation were measured by SE-HPLC. The protein aggregation results for the rotational stability study for the mAbs 39B6-AVE and 39B6-AYE are shown in Table 33.

TABLE 33

% Aggregate formation monitored by size-exclusion chromatography in rotational stability study for mAbs 39B6-AVE and 39B6-AYE.

| 39B6-AVE | | 39B6-AYE | |
|---|---|---|---|
| | Sample | | |
| Ref | 96 h | Ref | 96 h |
| 1.1 | 1.0 | 1.0 | 1.0 |

No change in % aggregate levels were observed for the mAbs following rotational stress as compared to the reference samples.

The areas of the monomeric peak for all different injections were also examined. The % monomer area results for the mAbs 39B6-AVE and 39B6-AYE are shown in Table 34.

TABLE 34

% Monomer area monitored by size-exclusion chromatography in rotational stability study for mAbs 39B6-AVE and 39B6-AYE

| 39B6-AVE | | 39B6-AYE | |
|---|---|---|---|
| | Sample | | |
| Ref | 96 h | Ref | 96 h |
| 98.9 | 99.0 | 99.0 | 99.0 |

No change in % monomer area was observed for either mAb after 96 hours of rotation as compared to the reference samples.

For both antibodies, no change in SE-HPLC profile was observed after 96 hours of rotation as compared to the reference samples.

Analysis by SDS-PAGE

Rotation samples were analyzed for their integrity by SDS-PAGE under non-reducing and reducing conditions. The results are summarized in Table 35 for mAbs 39B6-AVE and 39B6-AYE.

TABLE 35

Total percentage of full length Ab/heavy chain estimated by SDS-PAGE analysis and Odyssey scanning in rotational stability study for mAbs 39B6-AVE and 39B6-AYE

| | Non-reducing conditions | | Reducing conditions | |
|---|---|---|---|---|
| | Ref | 96 hours | Ref | 96 hours |
| | % full-length 39B6-AVE | | | |
| Sample | 81.3 | 76.6 | 91.0 | 90.7 |

TABLE 35-continued

Total percentage of full length Ab/heavy chain estimated
by SDS-PAGE analysis and Odyssey scanning in rotational
stability study for mAbs 39B6-AVE and 39B6-AYE

|  | Non-reducing conditions | | Reducing conditions | |
|---|---|---|---|---|
|  | Ref | 96 hours | Ref | 96 hours |
|  | % full-length 39B6-AYE | | | |
| Sample | 76.2 | 79.0 | 91.5 | 92.6 |

Figure 15:
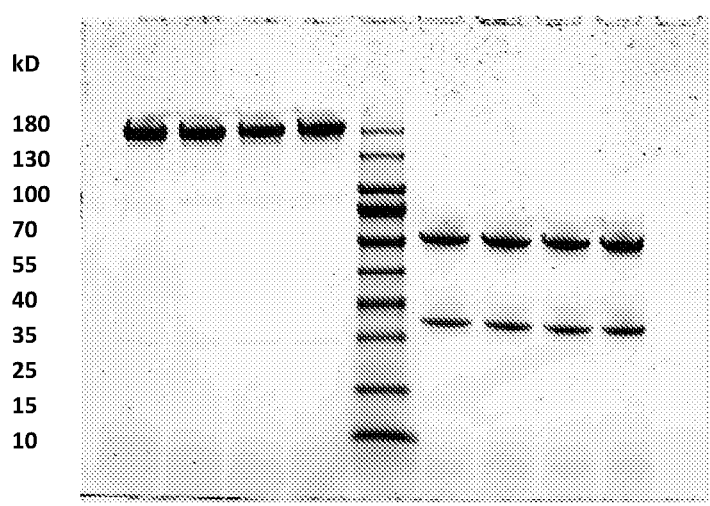
FIG. 15 shows the results of SDS-PAGE analysis of antibody samples after 96 hours of rotation. Markers appear at the centre of the gel. To the left of the markers, the 4 samples are the samples analysed under non-reducing conditions: (i) Ref for 39B6-AVE; (ii) Rotated sample for 39B6-AVE; (iii) Ref for 39B6-AYE; and (iv) Rotated sample for 39B6-AYE. To the right of the markers, the 4 samples are the samples analysed under reducing conditions: (i) Ref for 39B6-AVE; (ii) Rotated sample for 39B6-AVE; (iii) Ref for 39B6-AYE; and (iv) Rotated sample for 39B6-AYE.

The SDS-PAGE gel for both mAbs after 96 hours of rotation can be seen in FIG. 15. No changes were observed for either antibody after 96 hours of rotation.

Analysis for Target Binding in Biacore

Figure 16:
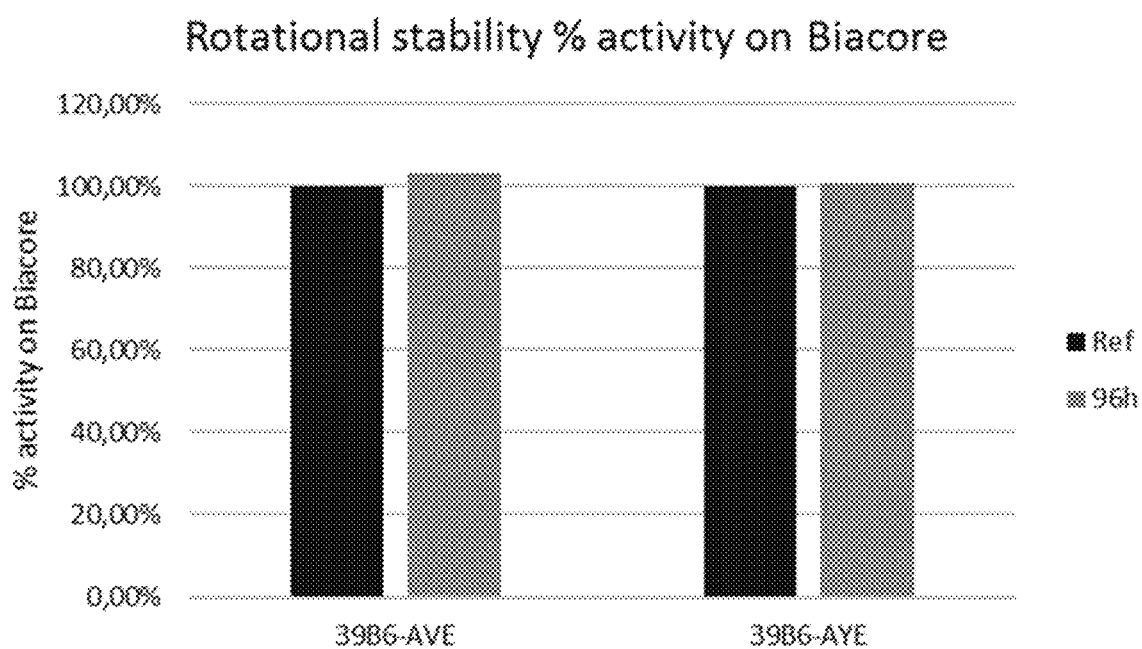
FIG. 16 shows target binding activity as measured by SPR following rotational stability testing for mAbs 39B6-AVE and 39B6-AYE. The reference sample was set as 100% binding activity.

Samples were tested for their target binding activity in Biacore by measuring the slope after 96 hours of rotation. The reference sample was set as 100% of the activity. The results for both mAbs 39B6-AVE and 39B6-AYE are shown in FIG. 16.

Analysis for Protein Concentration

The protein concentration of the rotational samples was measured on NanoDrop.

Figure 17:
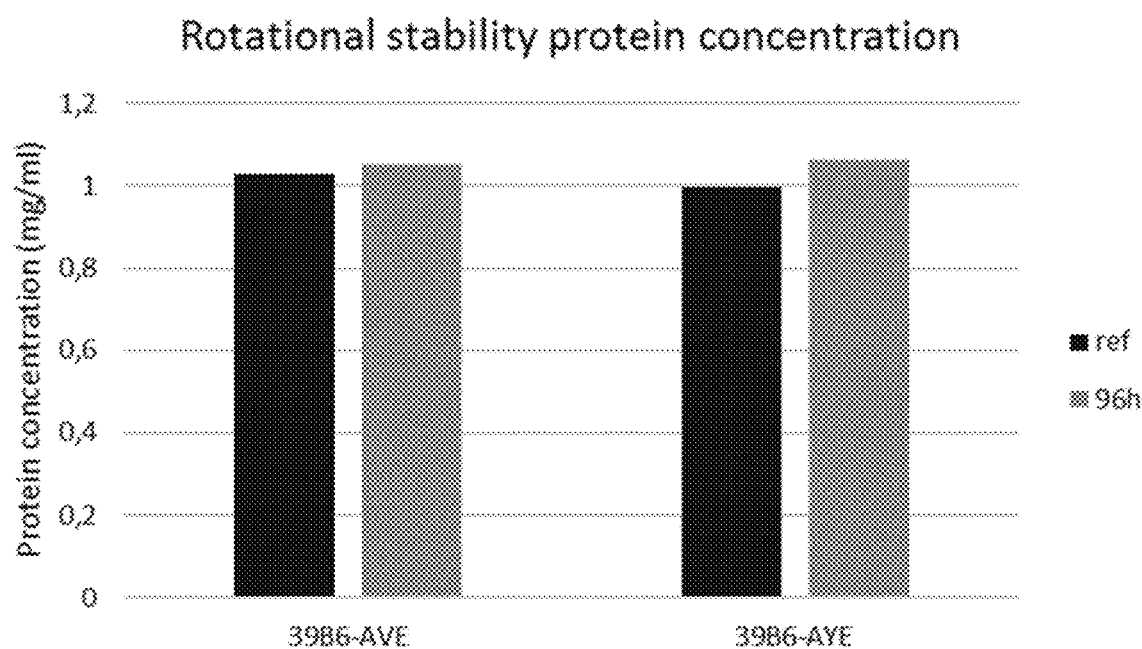
FIG. 17 shows the protein concentration (mg/ml) for samples of mAbs 39B6-AVE and 39B6-AYE following rotational stability testing.

In Table 36, the measured protein concentration for mAbs 39B6-AVE and 39B6-AYE after 96 hours of rotation is shown. Also, FIG. 17 shows these results for both mAbs.

TABLE 36

Protein concentration (mg/ml) in rotational
stability for mAbs 39B6-AVE and 39B6-AYE

| 39B6-AVE | | 39B6-AYE | |
|---|---|---|---|
| Sample | | | |
| Ref | 96 h | Ref | 96 h |
| 1.0 | 1.1 | 1.0 | 1.1 |

No protein loss was observed for both mAbs after 96 hours of rotation.

Conclusion of the Rotational Stability Study

The rotational stability study did not reveal any difference between the tested mAbs 39B6-AVE and 39B6-AYE.

2.2.5 Primary Sequence Analysis by Peptide Mapping

Samples from the temperature, freeze-thaw and rotational stability study were analyzed using Tryptic peptide mapping RP-HPLC-UV-MS methodology to identify modifications (deamidation, isomerization and oxidation) at the protein (peptide) level.

Deamidation in the CDR3 of the heavy chain at the positions 95-96 (amino acids NE) was engineered out in mAbs 39B6-AVE and 39B6-AYE by mutation of position N95. This deamidation site is still present in mAbs 39B6-ANK and 39B6-ANR and significant deamidation/isomerization was detected after 28 days at both 5° C. and 37° C. in the temperature stability study and also in the freeze-thaw and rotational stability study. It was concluded that deamidation could not be prevented by the introduction of bulky positively charged residues downstream of N95.

At position 100f of the CDR3 of the heavy chain there is a methionine that is essential for high binding affinity. Temperature, freeze-thaw and rotational stability studies have demonstrated that oxidation of M100f does not occur in mAbs 39B6-AYE and 39B6-ANK, while oxidation is still observed for mAbs 39B6-AVE and 39B6-ANR. This demonstrates that the amino acids at positions 95 and 96 influence the sensitivity towards oxidation of the downstream methionine. Table 37 shows an overview of the levels of oxidation and deamidation of peptides covering the heavy chain CDR3, which were generated by tryptic digestion.

TABLE 37

Extent of oxidation and deamidation of peptides within the heavy chain CDR3

| | Oxidation (%) | | | | Deamidation (%) | | | |
|---|---|---|---|---|---|---|---|---|
| | 5 °C. day 28 | 37 °C. day 28 | Rotational (96 h) | Freeze thaw (10x) | 5 °C. day 28 | 37 °C. day 28 | Rotational (96 h) | Freeze thaw (10x) |
| 39B6-AVE | 1.08 | 10.51 | 1.58 | 3.47 | 0 | 0 | 0 | 0 |
| 39B6-AYE | Below the limit of quantitation (LOQ) | | | | 0 | 0 | 0 | 0 |
| 39B6-ANK | Below the limit of quantitation (LOQ) | | | | 4.72 | 11.15 | 3.5 | 4.75 |
| 39B6-ANR | 9.20 | 20.98 | 19.37 | 12.47 | 12.85 | 34.38 | 12.79 | 12.77 |

Figure 18:
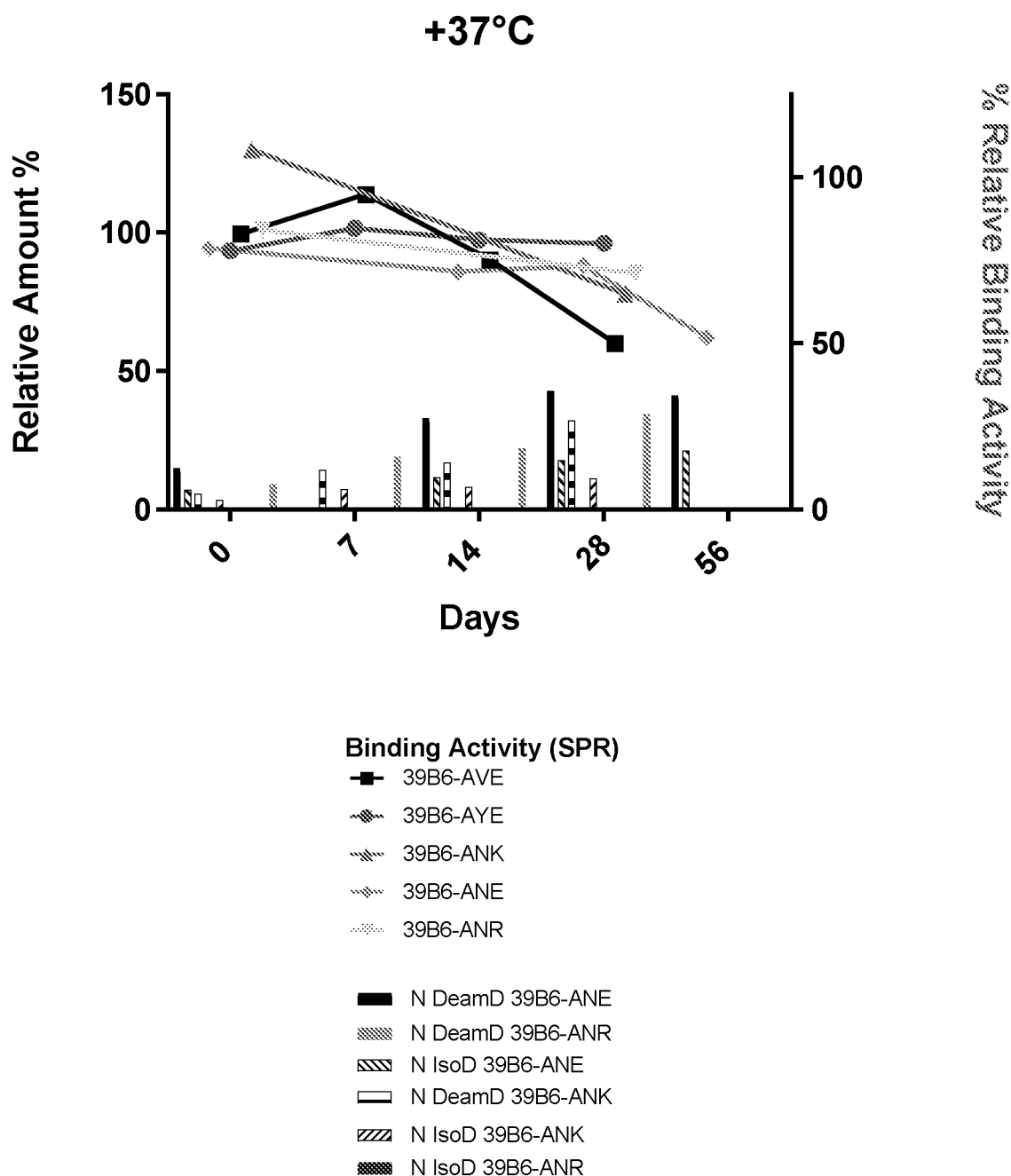
FIG. 18 shows the relative amount of deamidation and isomerization of position N95 in the antibodies 39B6-ANE, 39B6-ANR and 3986-ANK over a 56-day period. Antibodies 39B6-AVE and 39B6-AYE are not included because these antibodies have had residue "N95" removed from CDR3. Also shown is the relative binding activity for mAbs 39B6-ANE, 39B6-AVE, 39B6-AYE, 39B6-ANK and 39B6-ANR over the 56 d time course, for samples stored at 37° C.

* Below the limit of quantitation (LOQ) = intensity of oxidized form is close to background The relative amount of deamidation and isomerization of N95, and the relative binding activity of the variants stored at 37° C. are depicted in FIG. 18. Also the original 39B6-A is displayed in the figure (labelled 39B6-ANE). Because N95 has been mutated in mAbs 39B6-AVE and 39B6-AYE, deamidation and isomerization levels are zero and therefore not included. The correlation between deamidation of N95 and lower target binding activity observed for mAbs 39B6-ANK and 39B6-ANR suggests that N95 deamidation negatively affects the binding of the mAb to its target.

Conclusion

The GARP-TGF-β1 antibody variant 39B6-AYE is a particularly good GARP-TGF-β1 antibody to take forward for clinical development because it:

Retains high affinity binding to its target, the GARP-TGF-β1 complex;

Displays good potency in the SMAD2 phosphorylation assay;

Does not undergo deamidation or isomerization in CDR3

Does not undergo oxidation in CDR3

Displays high human homology (95%)

Displays improved stability as compared with 39B6-A, as measured by different stability assays.

The CDR and variable domain sequences for 39B6-AYE are shown in Tables 38 and 39 below. The full-length heavy chain and light chain sequences are shown in Table 40. The polynucleotide sequences encoding the VH and VL domains and the full-length heavy and light chains are shown in Table 41.

TABLE 38

VH and VL CDR sequences for 39B6-AYE

| 39B6-AYE | | | SEQ ID NO: |
|---|---|---|---|
| VH | CDR1 | SYYID | 4 |
|  | CDR2 | RIDPEDAGTKYAQKFQG | 12 |
|  | CDR3 | YEWETVVVGDLMYEYEY | 13 |
| VL | CDR1 | QASQSISSYLA | 9 |
|  | CDR2 | GASRLKT | 10 |
|  | CDR3 | QQYASVPVT | 11 |

TABLE 39

VH and VL domain sequences for 39B6-AYE

| 39B6-AYE | | SEQ ID NO: |
|---|---|---|
| VH | QVQLVQPGAEVRKPGASVKVSCKASGYRFTSYYIDWV RQAPGQGLEWMGRIDPEDAGTKYAQKFQGRVTMTAD TSTSTVYVELSSLRSEDTAVYYCARYEWETVVVGDLM YEYEYWGQGTLVTVSS | 14 |
| VL | DIQMTQSPSSLSASVGDRVTITCQASQSISSYLAWYQQ KPGQAPKILIYGASRLKTGVPSRFSGSGSGTSFTLTIS SLEPEDAATYYCQQYASVPVTFGQGTKVEIK | 15 |

TABLE 40

Heavy chain and light chain sequences for 39B6-AYE

| 39B6-AYE | | SEQ ID NO: |
|---|---|---|
| Heavy chain | QVQLVQPGAEVRKPGASVKVSCKASGYRFTSYYIDWV RQAPGQGLEWMGRIDPEDAGTKYAQKFQGRVTMTAD TSTSTVYVELSSLRSEDTAVYYCARYEWETVVVGDLM YEYEYWGQGTLVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVDK RVESKYGPPCPPCPAPEFLGGPSVFLFPPKPKDTLMIS RTPEVTCVVVDVSQEDPEVQFNWYVDGVEVHNAKTK PREEQFNSTYRVVSVLTVLHQDWLNGKEYKCKVSNKG LPSSIEKTISKAKGQPREPQVYTLPPSQEEMTKNQVSL TCLVKGFYPSDIAVEWESNGQPENNYKTTPPVLDSDG SFFLYSRLTVDKSRWQEGNVFSCSVMHEALHNHYTQK SLSLSLG | 16 |
| Light chain | DIQMTQSPSSLSASVGDRVTITCQASQSISSYLAWYQQ KPGQAPKILIYGASRLKTGVPSRFSGSGSGTSFTLTISS LEPEDAATYYCQQYASVPVTFGQGTKVEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC | 17 |

TABLE 41

Polynucleotide sequences encoding 39B6-AYE

| | | SEQ ID NO: |
|---|---|---|
| VH | CAAGTCCAACTTGTCCAACCGGGGGCGGAAGTGCG GAAGCCGGGGCGAGCGTGAAAGTCTCGTGCAAGG CATCGGGATACCGATTCACATCATATTACATCGACTG GGTCAGGCAAGCGCCGGGGCAAGGGCTGGAATGG ATGGGGCGGATCGACCCGGAGGATGCCGGGACGAA ATATGCGCAAAAATTCCAAGGGCGCGTCACGATGAC GGCCGACACATCGACGAGCACGGTATACGTGGAGC TGAGCTCGCTGAGGAGCGAGGACACCGCGGTATAC TACTGCGCGCGATACGAATGGGAGACCGTCGTCGT CGGGGACCTGATGTACGAATACGAATACTGGGGGC AAGGGACGCTTGTCACGGTCTCGAGC | 18 |
| VL | GACATCCAGATGACTCAGAGCCCTTCCAGCCTGAGC GCCTCTGTGGGAGATAGAGTCACCATCACATGCCAG GCTAGTCAGTCAATTTCTAGTTACCTGGCATGGTATC AGCAGAAGCCTGGCCAGGCACCTAAAATCCTGATCT ACGGAGCCAGTAGGCTGAAGACAGGGGTGCCATCT CGGTTCTCCGGCAGCGGATCTGGGACATCCTTTACT CTGACCATCTCATCCCTGGAGCCAGAAGACGCCGCT ACATACTATTGTCAGCAGTATGCTTCCGTGCCCGTC ACATTCGGTCAGGGCACTAAGGTCGAGATCAAG | 19 |
| Heavy chain | CAAGTCCAACTTGTCCAACCGGGGGCGGAAGTGCG GAAGCCGGGGCGAGCGTGAAAGTCTCGTGCAAGG CATCGGGATACCGATTCACATCATATTACATCGACTG GGTCAGGCAAGCGCCGGGGCAAGGGCTGGAATGG ATGGGGCGGATCGACCCGGAGGATGCCGGGACGAA ATATGCGCAAAAATTCCAAGGGCGCGTCACGATGAC GGCCGACACATCGACGAGCACGGTATACGTGGAGC TGAGCTCGCTGAGGAGCGAGGACACCGCGGTATAC TACTGCGCGCGATACGAATGGGAGACCGTCGTCGT CGGGGACCTGATGTACGAATACGAATACTGGGGGC AAGGGACGCTTGTCACGGTCTCGAGCGCTAGCACC AAGGGCCCCTCCGTGTTCCCCCTGGCCCCTTGCTC CCGGTCCACCTCCGAGTCTACCGCCGCTCTGGGCT GCCTGGTGAAAGACTACTTCCCCGAGCCTGTGACCG TGAGCTGGAACTCTGGCGCCCTGACCTCCGGCGTG CACACCTTCCTGCCGTGCTGCAATCCTCCGGCCTG TACTCCCTGTCCTCCGTGGTGACAGTGCCCTCCTCC AGCCTGGGCACCAAGACCTACACCTGTAACGTGGAC CACAAGCCCTCCAACACCAAGGTGGACAAGCGGGT GGAATCTAAATACGGCCCTCCCTGCCCCCCCTGCCC TGCCCCTGAATTTCTGGGCGGACCTTCCGTGTTTCT GTTCCCCCCAAAGCCCAAGGACACCCTGATGATCTC CCGGACCCCCGAAGTGACCTGCGTGGTGGTGGACG TGTCCCAGGAAGATCCAGAGGTGCAGTTCAACTGGT ATGTTGACGGCGTGGAAGTGCACAACGCCAAGACC AAGCCCAGAGAGGAACAGTTCAACTCCACCTACCGG GTGGTGTCCGTGCTGACCGTGCTGCACCAGGACTG GCTGAACGGCAAAGAGTACAAGTGCAAGGTGTCCAA CAAGGGCCTGCCCTCCAGCATCGAAAAGACCATCTC CAAGGCCAAGGGCCAGCCCCGCGAGCCCCAGGTGT ACACCCTGCCCCCTAGCCAGGAAGAGATGACCAAG AACCAGGTGTCCCTGACCTGTCTGGTGAAAGGCTTC TACCCCTCCGACATTGCCGTGGAATGGGAGTCCAAC GGCCAGCCCGAGAACAACTACAAGACCACCCCCCC TGTGCTGGACTCCGACGGCTCCTTCTTCCTGTACTC TCGGCTGACAGTGGATAAGTCCCGGTGGCAGGAAG GCAACGTGTTCTCCTGCAGCGTGATGCACGAGGCC CTGCACAACCACTATACCCAGAAGTCCCTGTCCCTG AGCCTGGGC | 20 |
| Light chain | GACATCCAGATGACTCAGAGCCCTTCCAGCCTGAGC GCCTCTGTGGGAGATAGAGTCACCATCACATGCCAG GCTAGTCAGTCAATTTCTAGTTACCTGGCATGGTATC AGCAGAAGCCTGGCCAGGCACCTAAAATCCTGATCT ACGGAGCCAGTAGGCTGAAGACAGGGGTGCCATCT CGGTTCTCCGGCAGCGGATCTGGGACATCCTTTACT CTGACCATCTCATCCCTGGAGCCAGAAGACGCCGCT ACATACTATTGTCAGCAGTATGCTTCCGTGCCCGTC ACATTCGGTCAGGGCACTAAGGTCGAGATCAAGCGT ACGGTCGCGGCGCCTTCTGTGTTCATTTTCCCCCCA TCTGATGAACAGCTGAAATCTGGCACTGCTTCTGTG GTCTGTCTGCTGAACAACTTCTACCCTAGAGAGGCC | 21 |

TABLE 41-continued

Polynucleotide sequences encoding 39B6-AYE

SEQ ID NO:

AAAGTCCAGTGGAAAGTGGACAATGCTCTGCAGAGT
GGGAATTCCCAGGAATCTGTCACTGAGCAGGACTCT
AAGGATAGCACATACTCCCTGTCCTCTACTCTGACA
CTGAGCAAGGCTGATTACGAGAAACACAAAGTGTAC
GCCTGTGAAGTCACACATCAGGGGCTGTCTAGTCCT
GTGACCAAATCCTTCAATAGGGGAGAGTGC

Example 3. Batch Testing of 39B6-AYE (ARGX-115)

The pilot drug substance batch of ARGX-115 was tested for stability over a three-month period. Test samples of the pilot drug substance batch were stored at the intended storage condition of −70° C., at the accelerated storage condition of +5° C. and the stressed storage condition of +25° C. The pilot drug substance was presented in the formulation: 10 mM Histidine/Histidine Hydrochloride, 200 mM Sucrose, 40 mM Arginine, 0.03% (w/v) polysorbate 80 at pH 6.0 and a protein concentration of 20.0±2.0 mg/ml.

ARGX-115 pilot drug substance batch was confirmed to be stable for three months when stored at the intended storage condition of −70° C. The SPR binding activity was also determined as a measure of the stability. The binding activity was expressed as a percentage of the binding activity of the reference sample that was kept at −70° C.

The results are shown in Table 42 below.

TABLE 42

| Method | Samples | Results |
| --- | --- | --- |
| ARGX115 Biacore | T3M +5° C. | 101% |
|  | T3M −70° C. | 106% |
|  | T3M +25° C. | 107% |

These results confirm that ARGX-115 is stable over a prolonged storage period.

Example 4. Characterisation of ARGX-115 Binding to the GARP-TGF-β Complex 4.1 Mature TGF-β is Essential for ARGX-115 Binding In nature, the GARP-TGF-β complex (GARP in complex with latent TGF-β) is formed in the endoplasmic reticulum with covalent cysteine interactions (disulphide bridges) between GARP and latent TGFβ. This complex is then displayed on the cell surface. In vitro, the GARP-TGF-β complex can be formed from recombinant human GARP and recombinant human latent TGF-β (C33S)-3×strep-tag. The C33S mutant form of latent TGF-β does not form the covalent interactions with GARP (or any of the Latent TGF-β Binding Proteins (LTBPs)) like are present in the native complex.

Figure 19:
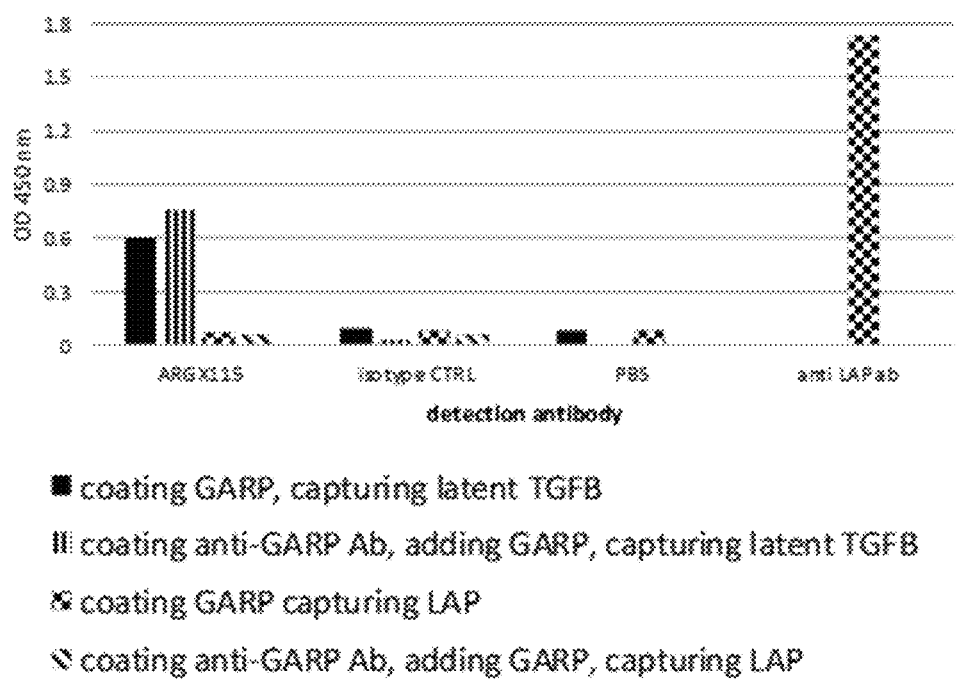
FIG. 19 shows the requirement for mature TGF-β in the binding of 39B6-AYE (ARGX-115) to the GARP-TGF-β complex. ELISA plates were coated with either GARP or the anti-GARP Ab ARGX-115. For ELISA plates coated with GARP, a complex with either full-length latent TGF-β (including both the LAP and mature TGF-β regions) or a complex with recombinant LAP was allowed to form by the addition of the relevant recombinant protein. For ELISA plates coated with ARGX-115, GARP was added and then either full-length latent TGF-β or LAP was added. ARGX-115 was only able to bind GARP in the presence of full-length TGF-β. Binding of ARGX-115 to the GARP-LAP complex did not occur. In contrast, an anti-LAP antibody was able to bind to the GARP-LAP complex. This demonstrates the requirement for mature TGF-β for binding of ARGX-115 to the GARP-TGF-β complex.

To demonstrate ARGX-115 binding to the in vitro-formed complex of recombinant GARP and recombinant latent TGFβ (C33S), recombinant GARP was coated to an ELISA plate (1 μg/mL human GARP O/N at 4° C.), blocked with blocking agent (casein-PBS), and latent TGF-β (5 μg/mL 1 h RT) was captured by the coated GARP. ARGX-115 and an isotype control antibody (1 μg/mL 1 h at RT) were allowed to bind to the complex, and were detected with a HRP-conjugated anti-human IgG. As shown in FIG. 19, ARGX-115 bound to the GARP-latent TGF-β (C33S) complex, whereas the isotype control did not.

The assay was also found to work the other way around. The ELISA plate was coated with ARGX-115, or an isotype control antibody (1 μg/mL ON at 4° C.) and blocked with blocking agent (casein-PBS). Recombinant GARP (5 μg/mL) was captured by the coated ARGX-115 antibody, the plate was washed, and recombinant latent TGF-β (C33S)-3×strep-tag (5 μg/mL) was captured and detected with streptavidin-HRP. HRP activity was detected only in the presence of ARGX-115 and not in wells of the plate coated with the isotype control.

To test the binding of ARGX-115 to a complex of GARP and the latency associated peptide (LAP) of TGF-β, a complex between recombinant GARP and recombinant LAP was formed. An ELISA plate was coated with recombinant GARP (1 μg/mL O/N 4° C.), blocked with blocking agent (casein-PBS), and LAP (5 μg/mL) was captured on the coated recombinant GARP. LAP binding was detected with anti-LAP-HRP. The binding of the anti-LAP-HRP demonstrates that the GARP-LAP complex does form in vitro. ARGX-115, however, did not show any binding to the GARP-LAP complex. Moreover, when the ELISA plate was coated with ARGX-115 (1 μg/mL ON 4° C.), recombinant GARP (5 μg/mL) was added followed by LAP (5 μg/mL), no binding of anti-LAP-HRP was measured. These results confirm that mature TGF-β is required for ARGX-115 binding to the GARP-TGF-β complex.

4.2 Impact of mutations in hTGF-β in complex with GARP on the Neutralizing Activity of ARGX-115

Figure 20:
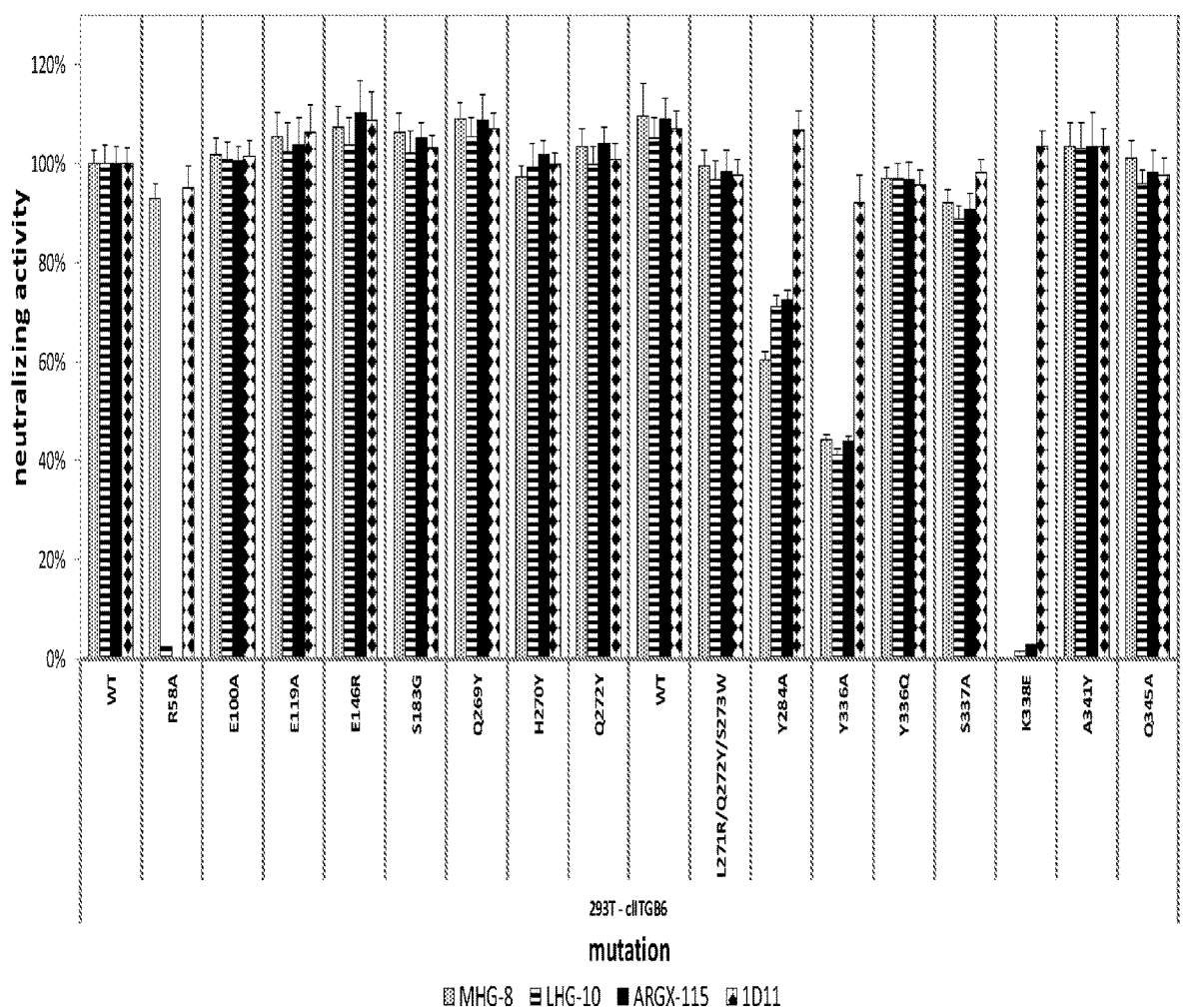
FIG. 20 shows the ability of antibodies to neutralize TGF-β activation by the GARP-TGF-β complex with various mutant forms of TGF-β. Neutralizing activity of ARGX-115 was abrogated by mutation of R58 in LAP and K338 in mature TGF-β.

293T cells stably expressing integrin αvβ6 (293Tcl.ITGB6) were transiently transfected with a mix of 3 plasmids (plasmid mix): (i) CAGA-luc reporter plasmid; (ii) human GARP (pEF-BOS-puro-hGARP); and (iii) either WT human TGF-β or mutant TGF-β (pDisplay). Integrin αvβ6 is one of the two TGF-β-activation integrins. 293Tcl.ITGB6 cells were detached and harvested from semi-confluent 75 cm² flasks, counted and diluted to 1E+06 cells/mL, and distributed 1 mL per eppendorf tube. 250 μl plasmid mix was added to each tube for transfection. Directly after transfection, the transfected cells were distributed in a 96-well optical plate, at 50 μl (4E+04 cells) per well, containing different test mAbs (ARGX-115, LHG10.6, 1D11 and MHG-8 at 100 μl/mL). 1D11 is a mAb against the active from of TGF-β isoform-1, -2 and -3. MHG-8 and LHG10.6 are described in WO2015/015003 and WO2016/125017. After incubation for 24 h at 37° C., the luciferase activity was measured. The value obtained with the transfection of mutant TGF-β was expressed as a percentage of the value obtained for WT-TGF-3. The results are shown in FIG. 20. As can be seen from the figure, the neutralizing activity of ARGX-115 measured against the TGF-β mutant including the R58A substitution and the TGF-β mutant including the K338E substitution was significantly reduced. This indicates that these two residues in the GARP-TGF-β complex are particularly important for the neutralizing activity of ARGX-115.

The invention claimed is:

1. A nucleic acid encoding a recombinant antibody or antigen binding fragment thereof, which binds to a complex of human glycoprotein A repetitions predominant (GARP) and TGF-β1, wherein the antibody or antigen binding fragment thereof comprises
a heavy chain variable domain (VH), wherein:
the VH CDR3 comprises the amino acid sequence YEWETVVVGDLMYEYEY (SEQ ID NO:13),
the VH CDR2 comprises the amino acid sequence RIDPEDAGTKYAQKFQG (SEQ ID NO:12), and
the VH CDR1 comprises the amino acid sequence SYYID (SEQ ID NO:4); and
a light chain variable domain (VL), wherein:
the VL CDR3 comprises the amino acid sequence QQYASVPVT (SEQ ID NO:11),
the VL CDR2 comprises the amino acid sequence GASRLKT (SEQ ID NO:10), and
the VL CDR1 comprises the amino acid sequence QASQSISSYLA (SEQ ID NO:9).

2. The nucleic acid of claim 1, wherein antibody or antigen binding fragment comprises a VH comprising the amino acid sequence of SEQ ID NO:14 and a VL comprising the amino acid sequence of SEQ ID NO:15.

3. The nucleic acid of claim 2, which comprises the sequences of SEQ ID NO:18 and SEQ ID NO:19.

4. The nucleic acid of claim 2, wherein the antibody or antigen binding fragment further comprises a CH1 domain, hinge region, CH2 domain and/or CH3 domain of a human IgG.

5. The nucleic acid of claim 4, wherein the human IgG is IgG1.

6. The nucleic acid of claim 4, wherein the human IgG is IgG4.

7. The nucleic acid of claim 6, wherein the human IgG4 has the substitution S228P in the CH3 domain.

8. The nucleic acid of claim 1, wherein antibody comprises a heavy chain comprising the amino acid sequence of SEQ ID NO:16 and a light chain comprising the amino acid sequence of SEQ ID NO:17.

9. The nucleic acid of claim 8, which comprises the sequences of SEQ ID NO:20 and SEQ ID NO:21.

10. An expression vector comprising the nucleic acid of claim 1 operably linked to regulatory sequences which permit expression of an antibody, antigen binding fragment, heavy chain variable domain, or light chain variable domain in a host cell or cell-free expression system.

11. A host cell or cell-free expression system containing the expression vector of claim 10.

12. A method of producing a recombinant antibody or antigen binding fragment thereof, comprising culturing the host cell or cell-free expression system of claim 11 under conditions which permit expression of the antibody or antigen binding fragment; and recovering the expressed antibody or antigen binding fragment.

13. An expression vector comprising the nucleic acid of claim 2 operably linked to regulatory sequences which permit expression of an antibody, antigen binding fragment, heavy chain variable domain, or light chain variable domain in a host cell or cell-free expression system.

14. A host cell or cell-free expression system containing the expression vector of claim 13.

15. A method of producing a recombinant antibody or antigen binding fragment thereof, comprising culturing the host cell or cell-free expression system of claim 14 under conditions which permit expression of the antibody or antigen binding fragment; and recovering the expressed antibody or antigen binding fragment.

16. An expression vector comprising the nucleic acid of claim 8 operably linked to regulatory sequences which permit expression of an antibody in a host cell or cell-free expression system.

17. A host cell or cell-free expression system containing the expression vector of claim 16.

18. A method of producing a recombinant antibody, comprising culturing the host cell or cell-free expression system of claim 17 under conditions which permit expression of the antibody; and recovering the expressed antibody.

* * * * *

SEQUENCE LISTING

<160> NUMBER OF SEQ ID NOS: 48

<210> SEQ ID NO 1
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 1

Glu Val Gln Leu Val Gln Pro Gly Ala Glu Leu Arg Asn Ser Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Asn Glu Trp Glu Thr Val Val Val Gly Asp Leu Met Tyr Glu
            100                 105                 110

Tyr Glu Tyr Trp Gly Gln Gly Thr Gln Val Thr Val Ser Ser
        115                 120                 125

<210> SEQ ID NO 2
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Asp Ser Leu Pro Val
                85                  90                  95

Thr Phe Gly Gln Gly Thr Lys Val Glu Leu Lys
            100                 105

<210> SEQ ID NO 3
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 3

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Asn Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Ala Ser Val Pro Val
                85                  90                  95

Thr Phe Gly Gln Gly Thr Lys Val Glu Leu Lys
            100                 105

<210> SEQ ID NO 4
<211> LENGTH: 5
<212> TYPE: PRT
<213> ORGANISM: Artificial sequence
<220> FEATURE:
<223> OTHER INFORMATION: Synthetic peptide

<400> SEQUENCE: 4

Ser Tyr Tyr Ile Asp
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Arg Ile Asp Pro Glu Asp Gly Gly Thr Lys Tyr Ala Gln Lys Phe Gln
1               5                   10                  15

Gly

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Asn Glu Trp Glu Thr Val Val Val Gly Asp Leu Met Tyr Glu Tyr Glu
1               5                   10                  15

Tyr

<210> SEQ ID NO 7
<211> LENGTH: 17
<212> TYPE: PRT
<213> ORGANISM: Artificial sequence
<220> FEATURE:
<223> OTHER INFORMATION: Synthetic peptide

<400> SEQUENCE: 7

Arg Ile Asp Pro Glu Glu Gly Gly Thr Lys Tyr Ala Gln Lys Phe Gln
1               5                   10                  15

Gly

<210> SEQ ID NO 8

```
<211> LENGTH: 17
<212> TYPE: PRT
<213> ORGANISM: Artificial sequence
<220> FEATURE:
<223> OTHER INFORMATION: Synthetic peptide

<400> SEQUENCE: 8

Arg Ile Asp Pro Glu Asp Ala Gly Thr Lys Tyr Ala Gln Lys Phe Gln
1               5                   10                  15
Gly

<210> SEQ ID NO 9
<211> LENGTH: 11
<212> TYPE: PRT
<213> ORGANISM: Artificial sequence
<220> FEATURE:
<223> OTHER INFORMATION: Synthetic peptide

<400> SEQUENCE: 9

Gln Ala Ser Gln Ser Ile Ser Ser Tyr Leu Ala
1               5                   10

<210> SEQ ID NO 10
<211> LENGTH: 7
<212> TYPE: PRT
<213> ORGANISM: Artificial sequence
<220> FEATURE:
<223> OTHER INFORMATION: Synthetic peptide

<400> SEQUENCE: 10

Gly Ala Ser Arg Leu Lys Thr
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Gln Gln Tyr Ala Ser Val Pro Val Thr
1               5

<210> SEQ ID NO 12
<211> LENGTH: 17
<212> TYPE: PRT
<213> ORGANISM: Artificial sequence
<220> FEATURE:
<223> OTHER INFORMATION: Synthetic peptide

<400> SEQUENCE: 12

Arg Ile Asp Pro Glu Asp Ala Gly Thr Lys Tyr Ala Gln Lys Phe Gln
1               5                   10                  15
Gly

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Tyr Glu Trp Glu Thr Val Val Val Gly Asp Leu Met Tyr Glu Tyr Glu
1               5                   10                  15
```

Tyr

```
<210> SEQ ID NO 14
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 14
```

Gln Val Gln Leu Val Gln Pro Gly Ala Glu Val Arg Lys Pro Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Ala Gly Thr Lys Tyr Ala Gln Lys Phe
    50                  55                  60

Gln Gly Arg Val Thr Met Thr Ala Asp Thr Ser Ser Thr Val Tyr
65                  70                  75                  80

Val Glu Leu Ser Ser Leu Arg Ser Glu Asp Thr Ala Val Tyr Tyr Cys
                85                  90                  95

Ala Arg Tyr Glu Trp Glu Thr Val Val Val Gly Asp Leu Met Tyr Glu
            100                 105                 110

Tyr Glu Tyr Trp Gly Gln Gly Thr Leu Val Thr Val Ser Ser
        115                 120                 125

```
<210> SEQ ID NO 15
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 15
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Ser Leu Glu Pro
65                  70                  75                  80

Glu Asp Ala Ala Thr Tyr Tyr Cys Gln Gln Tyr Ala Ser Val Pro Val
                85                  90                  95

Thr Phe Gly Gln Gly Thr Lys Val Glu Ile Lys
            100                 105

```
<210> SEQ ID NO 16
<211> LENGTH: 452
<212> TYPE: PRT
<213> ORGANISM: Artificial sequence
<220> FEATURE:
<223> OTHER INFORMATION: Synthetic polypeptide

<400> SEQUENCE: 16
```

Gln Val Gln Leu Val Gln Pro Gly Ala Glu Val Arg Lys Pro Gly Ala

```
1               5                   10                  15
Ser Val Lys Val Ser Cys Lys Ala Ser Gly Tyr Arg Phe Thr Ser Tyr
                20                  25                  30
Tyr Ile Asp Trp Val Arg Gln Ala Pro Gly Gln Gly Leu Glu Trp Met
                35                  40                  45
Gly Arg Ile Asp Pro Glu Asp Ala Gly Thr Lys Tyr Ala Gln Lys Phe
    50                  55                  60
Gln Gly Arg Val Thr Met Thr Ala Asp Thr Ser Thr Ser Thr Val Tyr
65                  70                  75                  80
Val Glu Leu Ser Ser Leu Arg Ser Glu Asp Thr Ala Val Tyr Tyr Cys
                85                  90                  95
Ala Arg Tyr Glu Trp Glu Thr Val Val Val Gly Asp Leu Met Tyr Glu
                100                 105                 110
Tyr Glu Tyr Trp Gly Gln Gly Thr Leu Val Thr Val Ser Ser Ala Ser
                115                 120                 125
Thr Lys Gly Pro Ser Val Phe Pro Leu Ala Pro Cys Ser Arg Ser Thr
    130                 135                 140
Ser Glu Ser Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
                180                 185                 190
Ser Val Val Thr Val Pro Ser Ser Ser Leu Gly Thr Lys Thr Tyr Thr
                195                 200                 205
Cys Asn Val Asp His Lys Pro Ser Asn Thr Lys Val Asp Lys Arg Val
    210                 215                 220
Glu Ser Lys Tyr Gly Pro Pro Cys Pro Pro Cys Pro Ala Pro Glu Phe
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser Gln Glu Asp Pro Glu Val Gln Phe Asn Trp Tyr Val Asp Gly Val
    275                 280                 285
Glu Val His Asn Ala Lys Thr Lys Pro Arg Glu Glu Gln Phe Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Gly Leu Pro Ser
                325                 330                 335
Ser Ile Glu Lys Thr Ile Ser Lys Ala Lys Gly Gln Pro Arg Glu Pro
                340                 345                 350
Gln Val Tyr Thr Leu Pro Pro Ser Gln Glu Glu Met Thr Lys Asn Gln
                355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Arg Leu
                405                 410                 415
Thr Val Asp Lys Ser Arg Trp Gln Glu Gly Asn Val Phe Ser Cys Ser
                420                 425                 430
```

Val Met His Glu Ala Leu His Asn His Tyr Thr Gln Lys Ser Leu Ser
        435                 440                 445

Leu Ser Leu Gly
    450

<210> SEQ ID NO 17
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Ser Leu Glu Pro
65                  70                  75                  80

Glu Asp Ala Ala Thr Tyr Tyr Cys Gln Gln Tyr Ala Ser Val Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 378
<212> TYPE: DNA
<213> ORGANISM: Artificial sequence
<220> FEATURE:
<223> OTHER INFORMATION: Synthetic polynucleotide

<400> SEQUENCE: 18
caagtccaac ttgtccaacc gggggcggaa gtgcggaagc cggggcgag cgtgaaagtc      60 tcgtgcaagg catcgggata ccgattcaca tcatattaca tcgactgggt caggcaagcg    120
ccggggcaag ggctggaatg gatggggcgg atcgacccgg aggatgccgg gacgaaatat    180
gcgcaaaaat tccaagggcg cgtcacgatg acggccgaca catcgacgag cacggtatac    240
gtggagctga gctcgctgag gagcgaggac accgcggtat actactgcgc gcgatacgaa    300

```
tgggagaccg tcgtcgtcgg ggacctgatg tacgaatacg aatactgggg gcaagggacg    360
cttgtcacgg tctcgagc                                                  378

<210> SEQ ID NO 19
<211> LENGTH: 321
<212> TYPE: DNA
<213> ORGANISM: Artificial sequence
<220> FEATURE:
<223> OTHER INFORMATION: Synthetic polynucleotide

<400> SEQUENCE: 19
gacatccaga tgactcagag cccttccagc ctgagcgcct ctgtgggaga tagagtcacc     60
atcacatgcc aggctagtca gtcaatttct agttacctgg catggtatca gcagaagcct    120
ggccaggcac ctaaaatcct gatctacgga gccagtaggc tgaagacagg ggtgccatct    180
cggttctccg gcagcggatc tgggacatcc tttactctga ccatctcatc cctggagcca    240
gaagacgccg ctacatacta ttgtcagcag tatgcttccg tgcccgtcac attcggtcag    300
ggcactaagg tcgagatcaa g                                              321

<210> SEQ ID NO 20
<211> LENGTH: 1356
<212> TYPE: DNA
<213> ORGANISM: Artificial sequence
<220> FEATURE:
<223> OTHER INFORMATION: Synthetic polynucleotide

<400> SEQUENCE: 20
caagtccaac ttgtccaacc gggggcggaa gtgcggaagc gggggcgag cgtgaaagtc       60 tcgtgcaagg catcgggata ccgattcaca tcatattaca tcgactgggt caggcaagcg    120
ccggggcaag ggctggaatg gatggggcgg atcgacccgg aggatgccgg gacgaaatat    180
gcgcaaaaat tccaagggcg cgtcacgatg acggccgaca tcgacgagca cggtatac     240 gtggagctga gctcgctgag gagcgaggac accgcggtat actactgcgc gcgatacgaa    300
tgggagaccg tcgtcgtcgg ggacctgatg tacgaatacg aatactgggg gcaagggacg    360
cttgtcacgg tctcgagcgc tagcaccaag ggcccctccg tgttccccct ggccccttgc    420
tcccggtcca cctccgagtc taccgccgct ctgggctgcc tggtgaaaga ctacttcccc    480
gagcctgtga ccgtgagctg gaactctggc gccctgacct ccggcgtgca caccttccct    540
gccgtgctgc aatcctccgg cctgtactcc ctgtcctccg tggtgacagt gccctcctcc    600
agcctgggca ccaagaccta cacctgtaac gtggaccaca gcccctccaa caccaaggtg    660
gacaagcggg tggaatctaa atacggccct cctgcccccc ctgccctgc cctgaatttt      720 ctgggcggac cttccgtgtt tctgttcccc ccaaagccca aggacaccct gatgatctcc    780
cggacccccg aagtgacctg cgtggtggtg gacgtgtccc aggaagatcc agaggtgcag    840
ttcaactggt atgttgacgg cgtggaagtg cacaacgcca agaccaagcc cagagaggaa    900
cagttcaact ccacctaccg ggtggtgtcc gtgctgaccg tgctgcacca ggactggctg    960
aacggcaaag agtacaagtg caaggtgtcc aacaagggcc tgcctccag catcgaaaag    1020 accatctcca aggccaaggg ccagccccgc gagccccagg tgtacaccct gcccctagc    1080 caggaagaga tgaccaagaa ccaggtgtcc ctgacctgtc tggtgaaagg cttctacccc    1140
tccgacattg ccgtggaatg ggagtccaac ggccagcccg agaacaacta caagaccacc    1200 cccctgtgc tggactccga cggctccttc ttcctgtact ccggctac agtggataag      1260 tcccggtggc aggaaggcaa cgtgttctcc tgcagcgtga tgcacgaggc cctgcacaac    1320
```

```
cactataccc agaagtccct gtccctgagc ctgggc                                    1356
```

<210> SEQ ID NO 21
<211> LENGTH: 642
<212> TYPE: DNA
<213> ORGANISM: Artificial sequence
<220> FEATURE:
<223> OTHER INFORMATION: Synthetic polynucleotide

<400> SEQUENCE: 21

```
gacatccaga tgactcagag cccttccagc ctgagcgcct ctgtgggaga tagagtcacc    60
atcacatgcc aggctagtca gtcaatttct agttacctgg catggtatca gcagaagcct   120
ggccaggcac ctaaaatcct gatctacgga gccagtaggc tgaagacagg ggtgccatct   180
cggttctccg gcagcggatc tgggacatcc tttactctga ccatctcatc cctggagcca   240
gaagacgccg ctacatacta ttgtcagcag tatgcttccg tgcccgtcac attcggtcag   300
ggcactaagg tcgagatcaa gcgtacggtc gcggcgcctt ctgtgttcat tttcccccca   360
tctgatgaac agctgaaatc tggcactgct tctgtggtct gtctgctgaa caacttctac   420
cctagagagg ccaaagtcca gtggaaagtg acaatgctc tgcagagtgg gaattcccag   480
gaatctgtca ctgagcagga ctctaaggat agcacatact ccctgtcctc tactctgaca   540
ctgagcaagg ctgattacga gaaacacaaa gtgtacgcct gtgaagtcac acatcagggg   600
ctgtctagtc ctgtgaccaa atccttcaat aggggagagt gc                       642
```

<210> SEQ ID NO 22
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 22

```
Gln Val Gln Leu Val Gln Pro Gly Ala Glu Val Arg Lys Pro Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Met Thr Ala Asp Thr Ser Thr Ser Thr Val Tyr
65                  70                  75                  80

Val Glu Leu Ser Ser Leu Arg Ser Glu Asp Thr Ala Val Tyr Tyr Cys
                85                  90                  95

Ala Arg Asn Glu Trp Glu Thr Val Val Val Gly Asp Leu Met Tyr Glu
            100                 105                 110

Tyr Glu Tyr Trp Gly Gln Gly Thr Leu Val Thr Val Ser Ser
        115                 120                 125
```

<210> SEQ ID NO 23
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Ser Leu Glu Pro
65                  70                  75                  80

Glu Asp Ala Ala Thr Tyr Tyr Cys Gln Gln Tyr Ala Ser Val Pro Val
                85                  90                  95

Thr Phe Gly Gln Gly Thr Lys Val Glu Ile Lys
            100                 105
```

<210> SEQ ID NO 24
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 24

```
Glu Val Gln Leu Val Gln Pro Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
    50                  55                  60

Gln Gly Arg Val Thr Phe Thr Ala Asp Thr Ser Thr Ser Thr Val Tyr
65                  70                  75                  80

Val Glu Leu Ser Ser Leu Arg Ser Glu Asp Thr Ala Val Tyr Tyr Cys
                85                  90                  95

Ala Arg Asn Glu Trp Glu Thr Val Val Gly Asp Leu Thr Tyr Glu
            100                 105                 110

Tyr Glu Tyr Trp Gly Gln Gly Thr Leu Val Thr Val Ser Ser
        115                 120                 125
```

<210> SEQ ID NO 25
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80
```

Glu Asp Phe Ala Thr Tyr Tyr Cys Gln Gln Tyr Ala Ser Val Pro Val
            85                  90                  95

Thr Phe Gly Gln Gly Thr Lys Val Glu Ile Lys
            100                 105

<210> SEQ ID NO 26
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 26

Gln Val Gln Leu Val Gln Pro Gly Ala Glu Leu Arg Asn Pro Gly Ala
1               5                   10                  15

Ser Val Lys Val Ser Cys Lys Ala Ser Gly Tyr Arg Phe Thr Ser Tyr
                20                  25                  30

Tyr Ile Asp Trp Val Arg Gln Ala Pro Gly Gln Gly Leu Glu Trp Met
            35                  40                  45

Gly Arg Ile Asp Pro Glu Asp Gly Gly Thr Lys Tyr Ala Gln Lys Phe
    50                  55                  60

Gln Gly Arg Val Thr Phe Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Glu Trp Glu Thr Val Val Val Gly Asp Leu Met Tyr Glu
            100                 105                 110

Tyr Glu Tyr Trp Gly Gln Gly Thr Leu Val Thr
        115                 120

<210> SEQ ID NO 27
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 27

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Ala Pro Lys Leu Leu Ile
            35                  40                  45

Tyr Gly Ala Ser Arg Leu Lys Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Tyr Ala Ser Val Pro Val
                85                  90                  95

Thr Phe Gly Gln Gly Thr Lys Val Glu Ile Lys
            100                 105

<210> SEQ ID NO 28
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 28

Gln Val Gln Leu Val Gln Pro Gly Ala Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Ala Gly Thr Lys Tyr Ala Gln Lys Phe
50                  55                  60

Gln Gly Arg Val Thr Phe Thr Ala Asp Thr Ser Thr Ser Thr Val Tyr
65                  70                  75                  80

Val Glu Leu Ser Ser Leu Arg Ser Glu Asp Thr Ala Val Tyr Tyr Cys
                85                  90                  95

Ala Arg Asn Glu Trp Glu Thr Val Val Gly Asp Leu Thr Tyr Glu
            100                 105                 110

Tyr Glu Tyr Trp Gly Gln Gly Thr Leu Val Thr Val Ser Ser
        115                 120                 125

<210> SEQ ID NO 29
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Asn Leu Leu Ile
        35                  40                  45

Tyr Gly Ala Ser Arg Leu Lys Thr Glu Val Pro Ser Arg Phe Ser Gly
50                  55                  60

Ser Gly Ser Gly Thr Asp Phe Thr Leu Ile Ser Gly Leu Glu Pro Glu
65                  70                  75                  80

Asp Ala Gly Thr Tyr Tyr Cys Gln Gln Tyr Ala Ser Val Pro Val Thr
                85                  90                  95

Phe Gly Gln Gly Thr Lys Val Glu Ile Lys
            100                 105

<210> SEQ ID NO 30
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 30

Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
50                  55                  60

```
Gln Gly Arg Val Thr Met Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Glu Trp Glu Thr Val Val Val Gly Asp Leu Met Tyr Glu
            100                 105                 110

Tyr Glu Tyr Trp Gly Gln Gly Thr Leu Val Thr Val Ser Ser
        115                 120                 125
```

<210> SEQ ID NO 31
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 31

```
Asp Ile Gln Met Thr Gln Ser Pro Ser Ser Leu Ser Ala Ser Leu Gly
  1               5                  10                  15

Asp Arg Val Thr Ile Thr Cys Gln Ala Ser Gln Ser Ile Ser Ser Tyr
             20                  25                  30

Leu Ala Trp Tyr Gln Gln Lys Pro Gly Gln Ala Pro Asn Ile Leu Ile
         35                  40                  45

Tyr Gly Ala Ser Arg Leu Lys Thr Gly Val Pro Ser Arg Phe Ser Gly
 50                  55                  60

Ser Gly Ser Gly Thr Asp Phe Thr Leu Thr Ile Ser Gly Leu Glu Ala
 65                  70                  75                  80

Glu Asp Phe Ala Thr Tyr Tyr Cys Gln Gln Tyr Ala Ser Val Pro Val
                 85                  90                  95

Thr Phe Gly Gln Gly Thr Lys Val Glu Ile Lys
            100                 105
```

<210> SEQ ID NO 32
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 32

```
Asn Glu Trp Glu Thr Val Val Val Gly Asp Leu Thr Tyr Glu Tyr Glu
  1               5                  10                  15

Tyr
```

<210> SEQ ID NO 33
<211> LENGTH: 662
<212> TYPE: PRT
<213> ORGANISM: Homo sapiens

<400> SEQUENCE: 33

```
Met Arg Pro Gln Ile Leu Leu Leu Ala Leu Leu Thr Leu Gly Leu
  1               5                  10                  15

Ala Ala Gln His Gln Asp Lys Val Pro Cys Lys Met Val Asp Lys Lys
             20                  25                  30

Val Ser Cys Gln Val Leu Gly Leu Leu Gln Val Pro Ser Val Leu Pro
         35                  40                  45

Pro Asp Thr Glu Thr Leu Asp Leu Ser Gly Asn Gln Leu Arg Ser Ile
 50                  55                  60
```

```
Leu Ala Ser Pro Leu Gly Phe Tyr Thr Ala Leu Arg His Leu Asp Leu
 65                  70                  75                  80

Ser Thr Asn Glu Ile Ser Phe Leu Gln Pro Gly Ala Phe Gln Ala Leu
                 85                  90                  95

Thr His Leu Glu His Leu Ser Leu Ala His Asn Arg Leu Ala Met Ala
            100                 105                 110

Thr Ala Leu Ser Ala Gly Gly Leu Gly Pro Leu Pro Arg Val Thr Ser
            115                 120                 125

Leu Asp Leu Ser Gly Asn Ser Leu Tyr Ser Gly Leu Leu Glu Arg Leu
        130                 135                 140

Leu Gly Glu Ala Pro Ser Leu His Thr Leu Ser Leu Ala Glu Asn Ser
145                 150                 155                 160

Leu Thr Arg Leu Thr Arg His Thr Phe Arg Asp Met Pro Ala Leu Glu
            165                 170                 175

Gln Leu Asp Leu His Ser Asn Val Leu Met Asp Ile Glu Asp Gly Ala
            180                 185                 190

Phe Glu Gly Leu Pro Arg Leu Thr His Leu Asn Leu Ser Arg Asn Ser
        195                 200                 205

Leu Thr Cys Ile Ser Asp Phe Ser Leu Gln Gln Leu Arg Val Leu Asp
    210                 215                 220

Leu Ser Cys Asn Ser Ile Glu Ala Phe Gln Thr Ala Ser Gln Pro Gln
225                 230                 235                 240

Ala Glu Phe Gln Leu Thr Trp Leu Asp Leu Arg Glu Asn Lys Leu Leu
            245                 250                 255

His Phe Pro Asp Leu Ala Ala Leu Pro Arg Leu Ile Tyr Leu Asn Leu
            260                 265                 270

Ser Asn Asn Leu Ile Arg Leu Pro Thr Gly Pro Pro Gln Asp Ser Lys
        275                 280                 285

Gly Ile His Ala Pro Ser Glu Gly Trp Ser Ala Leu Pro Leu Ser Ala
    290                 295                 300

Pro Ser Gly Asn Ala Ser Gly Arg Pro Leu Ser Gln Leu Leu Asn Leu
305                 310                 315                 320

Asp Leu Ser Tyr Asn Glu Ile Glu Leu Ile Pro Asp Ser Phe Leu Glu
            325                 330                 335

His Leu Thr Ser Leu Cys Phe Leu Asn Leu Ser Arg Asn Cys Leu Arg
            340                 345                 350

Thr Phe Glu Ala Arg Arg Leu Gly Ser Leu Pro Cys Leu Met Leu Leu
        355                 360                 365

Asp Leu Ser His Asn Ala Leu Glu Thr Leu Glu Leu Gly Ala Arg Ala
    370                 375                 380

Leu Gly Ser Leu Arg Thr Leu Leu Leu Gln Gly Asn Ala Leu Arg Asp
385                 390                 395                 400

Leu Pro Pro Tyr Thr Phe Ala Asn Leu Ala Ser Leu Gln Arg Leu Asn
            405                 410                 415

Leu Gln Gly Asn Arg Val Ser Pro Cys Gly Gly Pro Asp Glu Pro Gly
            420                 425                 430

Pro Ser Gly Cys Val Ala Phe Ser Gly Ile Thr Ser Leu Arg Ser Leu
        435                 440                 445

Ser Leu Val Asp Asn Glu Ile Glu Leu Leu Arg Ala Gly Ala Phe Leu
    450                 455                 460

His Thr Pro Leu Thr Glu Leu Asp Leu Ser Ser Asn Pro Gly Leu Glu
465                 470                 475                 480

Val Ala Thr Gly Ala Leu Gly Gly Leu Glu Ala Ser Leu Glu Val Leu
```

```
                      485                 490                 495
Ala Leu Gln Gly Asn Gly Leu Met Val Leu Gln Val Asp Leu Pro Cys
                500                 505                 510

Phe Ile Cys Leu Lys Arg Leu Asn Leu Ala Glu Asn Arg Leu Ser His
            515                 520                 525

Leu Pro Ala Trp Thr Gln Ala Val Ser Leu Glu Val Leu Asp Leu Arg
        530                 535                 540

Asn Asn Ser Phe Ser Leu Leu Pro Gly Ser Ala Met Gly Gly Leu Glu
545                 550                 555                 560

Thr Ser Leu Arg Arg Leu Tyr Leu Gln Gly Asn Pro Leu Ser Cys Cys
                565                 570                 575

Gly Asn Gly Trp Leu Ala Ala Gln Leu His Gln Gly Arg Val Asp Val
            580                 585                 590

Asp Ala Thr Gln Asp Leu Ile Cys Arg Phe Ser Ser Gln Glu Glu Val
        595                 600                 605

Ser Leu Ser His Val Arg Pro Glu Asp Cys Glu Lys Gly Gly Leu Lys
    610                 615                 620

Asn Ile Asn Leu Ile Ile Ile Leu Thr Phe Ile Leu Val Ser Ala Ile
625                 630                 635                 640

Leu Leu Thr Thr Leu Ala Ala Cys Cys Cys Val Arg Arg Gln Lys Phe
                645                 650                 655

Asn Gln Gln Tyr Lys Ala
            660

<210> SEQ ID NO 34
<211> LENGTH: 390
<212> TYPE: PRT
<213> ORGANISM: Homo sapiens

<400> SEQUENCE: 34

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190
```

```
Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
        210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
                    260                 265                 270

Ser Ser Arg His Arg Arg Ala Leu Asp Thr Asn Tyr Cys Phe Ser Ser
                275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
                340                 345                 350

Ala Pro Cys Cys Val Pro Gln Ala Leu Glu Pro Leu Pro Ile Val Tyr
                355                 360                 365

Tyr Val Gly Arg Lys Pro Lys Val Glu Gln Leu Ser Asn Met Ile Val
                370                 375                 380

Arg Ser Cys Lys Cys Ser
385                 390

<210> SEQ ID NO 35
<211> LENGTH: 249
<212> TYPE: PRT
<213> ORGANISM: Homo sapiens

<400> SEQUENCE: 35

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
        130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175
```

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 36
<211> LENGTH: 112
<212> TYPE: PRT
<213> ORGANISM: Homo sapiens

<400> SEQUENCE: 36

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 37
<211> LENGTH: 10
<212> TYPE: PRT
<213> ORGANISM: Homo sapiens

<400> SEQUENCE: 37

Glu Pro Lys Ser Cys Asp Lys Thr His Thr
1               5                   10

<210> SEQ ID NO 38
<211> LENGTH: 5
<212> TYPE: PRT
<213> ORGANISM: Homo sapiens

<400> SEQUENCE: 38

Cys Pro Pro Cys Pro
1               5

<210> SEQ ID NO 39
<211> LENGTH: 8
<212> TYPE: PRT
<213> ORGANISM: Homo sapiens

<400> SEQUENCE: 39

Ala Pro Glu Leu Leu Gly Gly Pro
1               5

```
<210> SEQ ID NO 40
<211> LENGTH: 12
<212> TYPE: PRT
<213> ORGANISM: Homo sapiens

<400> SEQUENCE: 40

Glu Leu Lys Thr Pro Leu Gly Asp Thr Thr His Thr
1               5                   10

<210> SEQ ID NO 41
<211> LENGTH: 50
<212> TYPE: PRT
<213> ORGANISM: Homo sapiens

<400> SEQUENCE: 41

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50

<210> SEQ ID NO 42
<211> LENGTH: 8
<212> TYPE: PRT
<213> ORGANISM: Homo sapiens

<400> SEQUENCE: 42

Ala Pro Glu Leu Leu Gly Gly Pro
1               5

<210> SEQ ID NO 43
<211> LENGTH: 7
<212> TYPE: PRT
<213> ORGANISM: Homo sapiens

<400> SEQUENCE: 43

Glu Ser Lys Tyr Gly Pro Pro
1               5

<210> SEQ ID NO 44
<211> LENGTH: 5
<212> TYPE: PRT
<213> ORGANISM: Homo sapiens

<400> SEQUENCE: 44

Cys Pro Ser Cys Pro
1               5

<210> SEQ ID NO 45
<211> LENGTH: 8
<212> TYPE: PRT
<213> ORGANISM: Homo sapiens

<400> SEQUENCE: 45

Ala Pro Glu Phe Leu Gly Gly Pro
1               5

<210> SEQ ID NO 46
<211> LENGTH: 3
<212> TYPE: PRT
<213> ORGANISM: Homo sapiens
```

```
<400> SEQUENCE: 46

Glu Arg Lys
1

<210> SEQ ID NO 47
<211> LENGTH: 10
<212> TYPE: PRT
<213> ORGANISM: Homo sapiens

<400> SEQUENCE: 47

Cys Cys Val Glu Cys Pro Pro Cys Pro
1               5                   10

<210> SEQ ID NO 48
<211> LENGTH: 7
<212> TYPE: PRT
<213> ORGANISM: Homo sapiens

<400> SEQUENCE: 48

Ala Pro Pro Val Ala Gly Pro
1               5
```